(12) United States Patent
Reiter et al.

(10) Patent No.: US 7,638,124 B2
(45) Date of Patent: *Dec. 29, 2009

(54) ANTIGEN-PRESENTING COMPLEX-BINDING COMPOSITIONS AND USES THEREOF

(75) Inventors: Yoram Reiter, Haifa (IL); Cyril Cohen, Nesher (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/510,229

(22) PCT Filed: Mar. 25, 2004

(86) PCT No.: PCT/IL2004/000275

§ 371 (c)(1), (2), (4) Date: Oct. 13, 2004

(87) PCT Pub. No.: WO2004/084798

PCT Pub. Date: Oct. 7, 2004

(65) Prior Publication Data

US 2006/0083735 A1  Apr. 20, 2006

Related U.S. Application Data

(63) Continuation-in-part of application No. 10/396,578, filed on Mar. 26, 2003, now abandoned.

(51) Int. Cl.
*A61K 39/00* (2006.01)
*A61K 39/395* (2006.01)
*C12P 21/00* (2006.01)

(52) U.S. Cl. .............. 424/130.1; 424/134.1; 424/178.1; 424/183.1; 530/387.1; 530/387.3

(58) Field of Classification Search .......................... None
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 5,591,829 A | 1/1997 | Matsushita | |
| 5,695,928 A | 12/1997 | Stewart et al. | |
| 5,952,471 A | 9/1999 | Griffiths Lawson | |
| 6,054,297 A * | 4/2000 | Carter et al. ............... | 435/69.6 |
| 6,291,160 B1 | 9/2001 | Lerner et al. | |
| 6,342,221 B1 | 1/2002 | Thorpe et al. | |
| 6,416,738 B1 | 7/2002 | Theodore et al. | |
| 6,992,176 B2 | 1/2006 | Reiter et al. | |

| | | |
|---|---|---|
| 2003/0129191 A1 | 7/2003 | Theodore et al. |
| 2003/0165993 A1 | 9/2003 | Buechler et al. |
| 2003/0223994 A1 | 12/2003 | Hoogenboom et al. |
| 2005/0152912 A1 | 7/2005 | Reiter et al. |
| 2005/0250833 A1 | 11/2005 | Attali et al. |
| 2005/0255101 A1 | 11/2005 | Reiter et al. |
| 2005/0287141 A1 | 12/2005 | Reiter |
| 2007/0196369 A1 | 8/2007 | Hoogenboom et al. |

FOREIGN PATENT DOCUMENTS

| | | | |
|---|---|---|---|
| EP | 1178116 | | 2/2002 |
| WO | WO 91/12332 | | 8/1991 |
| WO | WO 95/29193 | | 11/1995 |
| WO | WO 97/02342 | * | 1/1997 |
| WO | WO 99/49893 | | 10/1999 |
| WO | WO 01/96401 | | 12/2001 |
| WO | WO 03/068201 | | 8/2003 |
| WO | WO 03/070752 | | 8/2003 |
| WO | WO 2004/084798 | | 7/2004 |
| WO | WO 2006/103429 | | 10/2006 |

OTHER PUBLICATIONS

Daugherty et al., Polymerase chain reaction facilitates the cloning, CDR-grafting, and rapid expression of a murine monoclonal antibody directed against . . . , Nucleic Acids Research, vol. 19 No. 9, pp. 2471-2476 (May 1991).*
GenPept ABG38407 "immunoglobulin light chain variable region [*Homo sapiens*]," Jul. 2006.*
GenPept AAO45455 "immunoglobulin kappa chain variable region [*Homo sapiens*]," Nov. 2003.*
Poljak et al., Structure and specificity of antibody molecules, Philosophical Transactions of the Royal Society of London, Series B: Biological Sciences, vol. 272, pp. 43-51 (Nov. 1975).*
Shiono et al., "Spontaneous production of anti-IFN-alpha and anti-IL-12 autoantibodies by thymoma cells from *Myasthenia gravis* patients suggests autoimmunization in the tumor," International Immunology, vol. 15 No. 8, pp. 903-913 (Aug. 2003).*
Shriner et al., "Comparison of the human immune response to conjugate and polysaccharide pneumococcal vaccination using a reconstituted SCID mouse model," Vaccine, vol. 24 No. 49-50, pp. 7197-7203 (Nov. 2006).*
Reiter et al. "Peptide-Specific Killing of Antigen-Presenting Cells by A Recombinant Antibody-Toxin Fusion Protein Targeted to Major Histocompatibility Complex/Peptide Class I Complexes With T Cell Receptor-Like Specifity", Proc. Natl. Acad. Sci. USA, 94(9): 4631-4636, 1997.
Andersen et al. "A Recombinant Antibody With the Antigen-Specific, Major Histocompatibility Complex-Restricted Specifity of T Cells", Proceedings of the National Academy of Sciences, 93(5): 1820-1824, 1996.

(Continued)

*Primary Examiner*—Zachariah Lucas

(57) ABSTRACT

A composition-of-matter comprising an antibody or antibody fragment including an antigen-binding region capable of specifically binding an antigen-presenting portion of a complex composed of a human antigen-presenting molecule and an antigen derived from a pathogen is disclosed.

2 Claims, 10 Drawing Sheets
(10 of 10 Drawing Sheet(s) Filed in Color)

OTHER PUBLICATIONS

Rudikoff et al. "Single Amino Acid Substitution Altering Antigen-Binding Specifity", Proceedings of the National Academy of Sciences, USA, 79(6): 1979-1983, 1982.

Stedman Definition "Fab Fragment", Stedman's Online Medical Dictionary, 27th Edition. www.stedmans.com.

??? Definition "Fab", The Online Medical Ddictionary, cancerweb.ncl.ac.uk/omd/.

Engberg et al. "Recombinent Antibodies With the Antigen-Specific, MHC Restricted Specifity of T Cells: Novel Reagents for Basic and Clinical Investigations and Immunotherpy", Immunotechnology, 4(Nos. 3-4): 273-278, 1999.

Saito et al. "In Vivo Selection of T-Cell Receptor Junctional Region Sequences by HLA-A2 Human T-Cell Lymphotropic Virus Type 1 Tax11-19 Peptide Complexes", Journal of Virology, 75(2): 1065-1071, 2001.

Polakova et al. "Antibodies Directed Against the MHC-I Molecule H-2Dd Complexed With An Antigenic Peptide: Similarities to A T Cell Receptor With the Same Specifity", The Journal of Immunology, 165: 5703-5712, 2000.

Chung et al. "Competitive Inhibition In Vivo and Skewing of the T Cell Repertoire of Antigen-Specific CTL Priming by an Anti-Peptide-MHC Monoclonal Antbody", The Journal of Immunology, 167: 699-707, 2001.

Robert et al. "Antibody-Conjugated MHC Class I Tetramers Can Target Tumor Cells For Specific Iysis by T Lumphocytes", European Journal of Immunology, 30: 3165-3170, 2000.

Yoshida et al. "Isolation And Characterization Of Retrovirus From Cell Lines Of Human Adult T-Cell Leukemia And Its Implication In the Disease", PNAS, 79:2031-2035, 1982.

Köhler et al. "Continuous Cultures Of Fused Cells Secreting Antibody Of Predefined Specifity", Nature, 256:495-497, 1975.

Harding et al. "Quantitation Of Antigen-Presenting Cell MHC Class II/ Peptide Complexes Necessary For T-Cell Stimulation", Nature, 346: 574-576, 1990.

Christinck et al. "Peptide Binding To Class I MHC On Living Cels And Quantitation of Compplexes Required For CTL Lysis", Nature, 352: 67-70, 1991.

Aharoni et al. "Immunomodulation Of Experimental Allergic Encephalomyelitis By Antibodies To The Antigen-Ia Complex", Nature, 351: 147-149, 1991.

Haard et al. "A Large Non-Immunized Human Fab Fragment Phage Library That Permits Rabipd Isolation And Kinetic Analysis Of High Affinity Antibodies", The Journal of Biological Chemistry, 274(26): 18218-18230, 1999.

Winter et al. "Man-Made Antibodies", Nature, 349: 293-299, 1991.

Stubbs et al. "Influence Of Core Fucosylation On TheFlexibility Of A Biantennary N-Linked Oligosaccharide", Bichemistry, 35: 937-947, 1996.

Hoogenboom et al. "By-Passing Immunisation—Human Antibodies From Synthetic Repertoires Of Germline VH Gene Segments Rearranged In Vitro", Journal of Molecular Biology, 227: 381-388, 1992.

Grassmann et al. "Transformation To Continuous Growth Of Primary Human T Lymphocytes By Human T-Cell Leukemia Virus Type I X-Region Genes Tranduced By A Herpesvirus Saimiri Vector", PNAS, 86: 3351-3355, 1989.

Poiesz et al. "Detection And Isolation Of Type C Retrovirus Particles From Fresh And Cultured Lymphocytes Of A Patient With Cutaneous T-Cell Lymphoma", PNAS, 77(12): 7415-7419, 1980.

Porter "The Hydrolysis Of Rabbit γ-Globulin And Antibidies With Crystalline Papain", Biochemical Journal, 73: 119-126, 1959.

Pozzatti et al. "The Human T-Lymphotropic Virus Type I "Tax" Gene Can Cooperate With The "Ras" Oncogene To Induce Neoplastic Transformation Of Cells", Molecular and Cellular Biology, 10(1): 413-417, 1990.

Neuberger "Generating High-Avidity Human Mabs InMice", Nature Biotechnology, 14, 1996.

Bird et al. "Single-Chain Antigen-Binding Proteins", Science, 242: 423-426, 1988.

Marks et al. "By-Passing Immunization—Human Antibodies From V-Gene Libraries Displayed On Phage", Journal ofMelcular Biology, 222: 581-597, 1991.

Cote et al. "Generation Of Human Monoclonal Antibodies Reactive With Cellular Antigens", PNAS, 80: 2026-2030, 1983.

Murphy et al. "A Novel MHC Class II Epitope Expressed In Thymic Medulla But Not Cortex", Nature, 338:765-768, 1989.

Riechmann et al. "Reshaping Human Antibodies For Therapy", Nature 332: 323-327, 1988.

Bieganowska et al. "Direct Analysis Of Viral-Specific CD8 T Cells With Soluble HLA-A2/Tax11-19 Tetramer Complexes in Patients With Human T-Cell Lymphotropic Virus-Associated Myelopathy", he Journal of Immunology, 162:1765-1771, 1999.

Anton et al. "MHC Class I-Associated Peptides Produced From Endogenous Gene Products With Vastly Different Efficiencies", The Journal of Immunology, 158: 2535-2542, 1997.

Altman et al. "Phenotypic Analysis Of Antegen-Specific T Lymphocytes", Science, 274:94-96, 1996.

Chames et al. "Direct Selection Of A Human Antibody Fragment Directed Against The Tumor T-Cell Epitope HLA-A1-MAGE-A1 From A Nonimmunized Phage-Fab Library", PNAS, 97(14): 7969-7974, 2000.

Demotz et al. "The Minimal Number Of Class II MHC-Antigen Complexes Needed For T Cell Activation", Science, 249: 1028-1030, 1990.

Boerner et al. "Production Of Antigen-Specific Human Monoclonal Antibodies From In-Vitro-Primed Human Splenocytes", The Journal of Immunology, 147(1): 86-95, 1991.

Morrison "Success In Specification",Nature, 368:812-813,1994.

Jones et al. "Replacing The Complementarity-Determining Regions On A Human Antibody With Those From a Mouse", Nature, 321:522-525,1986.

Verhoeyen et al. "Reshaping Human Antiodies: Grafting an Antilysozyme Activity", Science, 239: 1534-1536, 1988.

Rosenberg Nature, 411: 380-384, 2001.

Lonberg et al. "Antigen-Specific Human Antibodies From Mice Comprising Four Distinct Genetic Modifications", Nature, 368, 856-859, 1994.

Verhoeyen et al. "Reshaping Human Antibodies: Grafting An Antilysozyme Activity", Science, 239, 1534-1536,1988.

International Preliminary Examination Report Dated Mar. 31, 2005 From the International Preliminary Examining Authority Re.: Application No. PCT/IL03/00105.

International Preliminary Report on Patentability Dated Oct. 13, 2005 From the International Bureau of WIPO Re.: Application No. PCT/IL2004/000275.

Invitation to Pay Additional Fees Dated Feb. 16, 2005 From the International Searching Authority Re.: Application No. PCT/IL2004/000275.

Official Action Dated Jan. 26, 2005 From the US Patent and Trademark Office Re.: U.S. Appl. No. 10/073,301.

Translation of Notice of Reason for Rejection Dated Nov. 7, 2008 From the Japanese Patent Office Re.: Application No. 2003-567383.

Translation of Notice of Reason for Rejection Dated Jun. 13, 2008 From the Japanese Patent Office Re.: Application No. 2003-567383.

Anichini et al. "Melanoma Cells and Normal Melanocytes Share Antigens Recognized by HLA-A2-Restricted Cytotoxic T Cell Clones From Melanoma Patients", The Journal of Experimental Medicine, 177: 989-998, 1993.

Arai et al. "Identification of Human Telomerase Reverse Transcriptase-Derived Peptides That Induce HLA-A24-Restricted Antileukemia Cytotoxic T Lymphocytes", Blood, 97(9): 2903-2907, 2001.

Bakker et al. "Melanocyte Lineage-Specific Antigen Gp100 Is Recognized by Melanoma-Derived Tumor-Infiltrating Lymphocytes", The Journal of Experimental Medicine, 179: 1005-1009, 1994.

Biddison et al. "Tax and M1 Peptide/HLA-A2-Specific Fabs and T Cell Receptors Recognize Nonidentical Structural Features on Peptide/HLA-A2 Complexes", Journal of Immunology, 171(6): 3064-3074, 2003.

Boon et al. "Human Tumor Antigens Recognized by T Lymphocytes", The Journal of Experimental Medicine, 183: 725-729, 1996.

Carmon et al. "Novel Breast-Tumor-Associated MUC1-Derived Peptides: Characterization in Db-/-X β2 Microglobulin (β2m) Null Mice Transgenic for A Chimeric HLA-A2.1/Db β2 Microglobulin Single Chain", International Journal of Cancer, 85(3): 391-397, 2000. Abstract.

Chowdhury et al. "Improving Antibody Affinity by Mimicking Somatic Hypermutation In Vitro", Nature Biotechnology, 17(6): 568-572, 1999. Abstract.

Cohen et al. "Direct Detection and Quantitation of A Distinct T-Cell Epitope Derived From Tumor-Specific Epithelial Cell-Associated Mucin Using Human Recombinant Antibodies Endowed With the Antigen-Specific, Major Histocompatibility Complex-Restricted Specificity of T Cells", Cancer Research, 62(20): 5835-5844, 2002. Esp. Abstract.

Cohen et al. "Direct Phenotypic Analysis of Human MHC Class I Antigen Presentation: Visualization, Quantification, and In Situ Detection of Human Viral Epitopes Using Peptide-Specific, MHC-Restricted Human Recombinant Antibodies", Journal of Immunology, 170(8): 4349-4361, 2003.

Cohen et al. "Generation of Recombinant Immunotoxins for Specific Targeting of Tumor-Related Peptides Presented by MHC Molecules", Methods in Molecular Biology, 207: 269-282, 2003. Abstract.

Cohen et al. Recombinant Antibodies With MHC-Restricted, Peptide-Specific, T-Cell Receptor-Like Specificity: New Tools to Study Antigen Presentation and TCR-Peptide-MHC Interactions, Journal of Molecular Recognition, 16(5): 324-332, 2003. Abstract.

Coulie et al. "A New Gene Coding for A Differentiation Antigen Recognized by Autologous Cytolytic T Lymphocytes on HLA-A2 Melanomas", Journal of Experimental Medicine, 180: 35-42, 1994.

Counter et al. "Telomerase Activity in Normal Leukocytes and in Hematologic Malignancies", Blood, 85(9): 2315-2320, 1995.

Dadaglio et al. "Characterization and Quantitation of Peptide-MHC Complexes Produced From Hen Egg Lysozyme Using A Monoclonal Antibody", Immunity, 6(6): 727-738, 1997. Abstract.

Day et al. "Direct Delivery of Exogenous MHC Class I Molecule-Binding Oligopeptides to the Endoplasmic Reticulum of Viable Cells", Proc. Natl. Acad. Sci. USA, 94: 8064-8069, 1997.

Denkberg et al. "Critical Role for CD8 in Binding of MHC Tetramers to TCR: CD8 Antibodies Block Specific Binding of Human Tumor-Specific MHC-Peptide Tetramers to TCR", The Journal of Immunology, 167: 270-276, 2001.

Denkberg et al. "Direct Visualization of Distinct T Cell Epitopes Derived From A Melanoma Tumor-Associated Antigen by Using Human Recombinant Antibodies With MHC-Restricted T Cell Receptor-Like Specificity", Proc. Natl. Acad. Sci. USA, 99(14): 9421-9426, 2002.

Denkberg et al. "Recombinant Human Single-Chain MHC-Peptide Complexes Made From E. coli by In Vitro Refolding: Functional Single-Chain MHC-Peptide Complexes and Tetramers With Tumor Associated Antigens", European Journal of Immunology, 30(12): 3522-3532, 2000. Abstract.

Derby et al. "High Avidity CTL Exploit Two Complementary Mechanisms to Provide Better Protection Against Viral Infection Than Low-Avidity CTL", The Journal of Immunology, 166: 1690-1697, 2001.

Dudley et al. "T-Cell Clones From Melanoma Patients Immunized Against An Anchor-Modified GP100 Peptide Display Discordant Effector Phenotypes", Cancer Journal, 6(2): 69-77, 2000. Abstract.

Dutoit et al. "Heterogenous T-Cell Response to MAGE-A10[254-262]: High Avidity-Specific Cytolytic T Lymphocytes Show Superior Antitumor Activity", Cancer Research, 61: 5850-5856, 2001.

Gennaro "Remington's Pharmaceutical Sciences 18th Edition", Mack Printing Co., p. 1579, 1990.

Harlow et al. "Antibodies, A Laboratory Manual", Cold Spring Harbor Laboratory, USA, p. 287, 1988.

Kawakami et al. "Identification of A Human Melanoma Antigen Recognized by Tumor-Infiltrating Lymphocytes Associated With In Vivo Tumor Rejection", Proc. Natl. Acad, Sci. USA, 91: 6458-6462, 1994.

Kim et al. "Specific Association of Human Telomerase Activity With Immortal Cells and Cancer", Science, 266(5193): 2011-2015, 1994. Abstract.

Kirkin et al. "Generation of Human-Melanoma-Specific T Lymphocyte Clones Defining Novel Cytolytic Targets With Panels of Newly Established Melanoma Cell Lines", Cancer Immunology and Immunotherapy, 41(2): 71-81, 1995. Abstract.

Kondo et al. "Activity of Immunotoxins Constructed With Modified Pseudomonas Exotoxin A Lacking the Cell Recognition Domain", The Journal of Biological Chemistry, 263(19): 9470-9475, 1988.

Krogsgaard et al. "Visualization of Myelin Basic Protein (MBP) T Cell Epitopes in Multiple Sclerosis Lesions Using A Monoclonal Antibody Specific for the Human Histocompatibility Leukocyte Antigen (HLA)-DR2-MBP 85-99 Complex", The Journal of Experimental Medicine, 191(8): 1395-1412, 2000.

Kugler et al. "Regression of Human Metastatic Renal Cell Carcinoma After Vaccination With Tumor Cell-Dendritic Cell Hybrids", Nature Medicine, 6(3): 332-336, 2000. Abstract.

Lee et al. "Characterization of Circulating T Cells Specific for Tumor-Associated Antigens in Melanoma Patients", Nature Medicine, 5(6): 677-685, 1999. Abstract.

Lev et al. "Isolation and Characterization of Human Recombinant Antibosies Endowed With the Antigen-Specific, Major Histocompatibility Complex-Restricted Specificity of T Cells Directed Toward the Widely Expressed Tumor T-Cell Epitopes of the Telomerase Catalytic Subunit", Cancer Research, 62: 3184-3194, 2002.

Lode et al. "Targeted Cytokines for Cancer Immunotherapy", Immunology Research, 21(2-3): 279-288, 2000. Abstract.

McEachern et al. "Telomeres and Their Control", Annual Reviews of Genetics, 34: 331-358, 2000. Abstract.

Minev et al. "Cytotoxic T Cell Immunity Against Telomerase Reverse Transcriptase in Humans", Proc. Natl. Acad. Sci. USA, 97(9): 4796-4801, 2000.

Murphy et al. "A Novel MHC Class II Epitope Expressed in Thymic Medulla But Not Cortex", Nature, 338: 765-768, 1989. Abstract.

Nakamura et al. "Reversing Time: Origin of Telomerase", Cell, 92: 587-590, 1998.

Ngo et al. "Computational Complexity, Protein Structure Prediction, and the Levinthal Paradox", The Protein Folding Problem and Tertiary Structure Prediction, p. 491-495, 1994.

Offringa et al. "Design and Evaluation of Antigen-Specific Vaccination Strategies Against Cancer", Current Opinion in Immunology, 12(5): 576-582, 2000. Abstract.

Ogg et al. "Quantitation of HIV-1-Specific Cytotoxic T Lymphocytes and Plasma Load of Viral RNA", Science, 279(5359): 2103-2106, 1998. Abstract.

Parkhurst et al. "Improved Induction of Melanoma-Reactive CTL With Peptides From the Melanoma Antigen Gp100 Modified at HLA-A*0201-Binding Residues", The Journal of Immunology, 157: 2539-2548, 1996. Tables II, III.

Pascolo et al. "HLA-A2.1-Restricted Education and Cytolytic Activity of CD8+ T Lymphocytes From β2 Microglobulin (β2m) HLA-A2.1 Monochain Transgenic H-2Db β2m Double Knockout Mice", Journal of Experimental Medicine, 185(12): 2043-2051, 1977.

Patamawenu "Generation of Functional HLA-A2 Molecules Covealently Attached to Antigenic Peptides", B.S. (University of Maryland) Thesis, p. 8-9, 1988. Abstract.

Porgador et al. "Localization, Qunatitation, and In Situ Detection of Specific Peptide-HC Class I Complexes Using A Monoclonal Antibody", Immunity, 6(6): 715-726, 1997. Abstract.

Rammensee et al. "MHC Ligands and Peptide Motifs", Molecular Biology Intelligence Unit, Landes Bioscience, p. 235-281, 1997.

Reay et al. "Determinatin of the Relationship Between T Cell Responsiveness and the Number of MHC-Peptide Complexes Using Specific Monoclonal Antibodies", The Journal of Immunology, 164(11): 5626-5634, 2000.

Reiter et al. "An Antibody Single-Domain Phage Display Library of A Native Heavy Chain Variable Region: Isolation of Functional Single-Domain VH Molecules With A Unique Interface", Journal of Molecular Biology, 290(3): 685-698, 1999. Abstract.

Reiter et al. "Antibody Engineering for Targeted Therapy of Cancer: Recombinant Fv-Immunotoxins", Current Pharmaceutical Biotechnology, 2: 19-46, 2001.

Reiter et al. "Recombinant Immunotoxins in Targeted Cancer Cell Therapy", Advances in Cancer Research, 81: 93-124, 2001. Abstract.

Renkvist et al. "A Listing of Human Tumor Antigens Recognized by T Cells", Cancer Immunology and Immunotherapy, 50(1): 3-15, 2001. Abstract.

Restifo et al. "Identification of Human Cancers Deficient in Antigen Processing", The Journal of Experimental Medicine, 177: 265-272, 1993.

Rivoltini et al. "Recognition of Melanoma-Derived Antigens by CTL: Possible Mechanisms Involved in Down-Regulating Anti-Tumor T-Cell Reactivity", Critical Review in Immunology, 18(1-2): 55-63, 1998. Abstract.

Seliger et al. "Antigen-Processing Machinery Breakdown and Tumor Growth", Immunology Today, 21(9): 455-464, 2000. Abstract.

Shay et al. "Telomerase and Cancer", Human Molecular Genetics, 10(7): 677-685, 2001.

Shriner et al. "Comparison of the Human Immune Response to Conjugate and Polysaccharide Pneumococcal Vaccination Using. A Reconstituted SCID Mouse Model", Vaccine, 24(49-50): 7197-7203, 2006. GenPept ABG38407.

Stanislawksi et al. "Circumventing Tolerance to A Human MDM2-Derived Tumor Antigen by TCR Gene Transfer", Nature Immunology, 2(10): 962-970, 2001. Abstract.

Stryhn et al. "Shared Fine Specificity Between T-Cell Receptors and An Antibody Recognizing A Peptide/Major Histocompatibility Class I Complex", Proc. Natl. Acad. Sci. USA, 93: 10338-10342, 1996.

Vonderheide et al. "The Telomerase Catalytic Subunit Is A Widely Expressed Tumor-Associated Antigen Recognized by Cytotoxic T Lymphocytes", Immunity, 10(6): 673-679, 1999. Abstract.

Waterhouse et al. "Combinatorial Infection and In Vivo Recombination: A strategy for Making Large Phage Antibody Repertoires", Nucleic Acids Research, 21(9): 2265-2266, 1993.

Withoff et al. "Bi-Specific Antibody Therapy for the Treatment of Cancer", Current Opinion in Molecular Therapy, 3(1): 53-62, 2001. Abstract.

Wülfing et al. "Correctly Folded T-Cell Receptor Fragments in the Periplasm of *Escherichia coli*", Journal of Molecular Biology, 242(5): 655-669, 1994. Abstract.

Yamano et al. "Detection of HTLV-I Tax11-19 Peptide/HLA-A*201 Complexes Are Overexpressed in HAM/TSP Patients", Aids Research and Human Retroviruses, 19(Suppl.): S-38, 2003. Abstract. & 11th International Conference on Human Retrovirology: HTLV and Related Viruses, San Francisco, USA, 2003. Abstract.

Yamano et al. "Increased Expression of Human T Lymphocyte Virus Type I (HTLV-I) Tax11-19 Peptide-Human Histocompatibility Leukocyte Antigen A*201 Complexes on CD4+ CD25+ T Cells Detected by Peptide-Specific, Major Histocompatibility Complex-Restricted Antibodies in Patients With HTLV-I-Associated Neurological Disease", Journal of Experimental Medicine, 199(10): 1367-1377, 2004.

Zhong et al. "Antigen-Unspecific B Cells and Lymphoid Dendritic Cells Both Show Extensive Surface Expression of Processed Antigen-Major Histocompatibility Complex Class II Complexes After Soluble Protein Exposure In Vivo or In Vitro", The Journal of Experimental Medicine, 186(5): 673-682, 1997.

Zhong et al. "Production, Specificity, and Funtionality of Monoclonal Antibodies to Specific Peptide-Major Histocompatibility Complex Class II Complexes Formed by Processing of Exogenous Protein", Proc. Natl. Acad. Sci. USA, 94: 13856-13861, 1997.

International Search Report Dated Aug. 7, 2009 From the International Searching Authority Re.: Application No. PCT/IL2009/000380.

International Search Report Dated Jul. 31, 2009 From the International Searching Authority Re.: Application No. PCT/IL2009/000379.

Notice of Allowance Dated Aug. 11, 2009 From the US Patent and Trademark Office Re.: U.S. Appl. No. 10/510,229.

Written Opinion Dated Aug. 7, 2009 From the International Searching Authority Re.: Application No. PCT/IL2009/000380.

Written Opinion Dated Jul. 31, 2009 From the International Searching Authority Re.: Application No. PCT/IL2009/000379.

Anikeeva et al. "Soluble HIV-Specific T Cell Receptor: Expression, Purification and Analysis of the Specificity", Journal of Immunological Methods, XP004430548, 277(1-2): 75-86, Jun. 1, 2003.

Denkberg et al. "Recombinant Antibodies With T-Cell Receptor-Like Specificity: Novel Tools to Study MHC Class I Presentation", Autoimmunity Reviews, XP024977451, 5(4): 252-257, Apr. 1, 2006.

Kfir et al. "Specific Association of Human Telomerase Activity With Immortal Cells and Cancer", Science, 266(5193): 2011-2015, 1994. Abstract.

Noy et al. "T-Cell Receptor-Like Antibodies: Novel Reagents for Clinical Cancer Immunology and Immunotherapy", Future Drugs, XP009067037, 5(3): 523-536, Jun. 1, 2005.

* cited by examiner

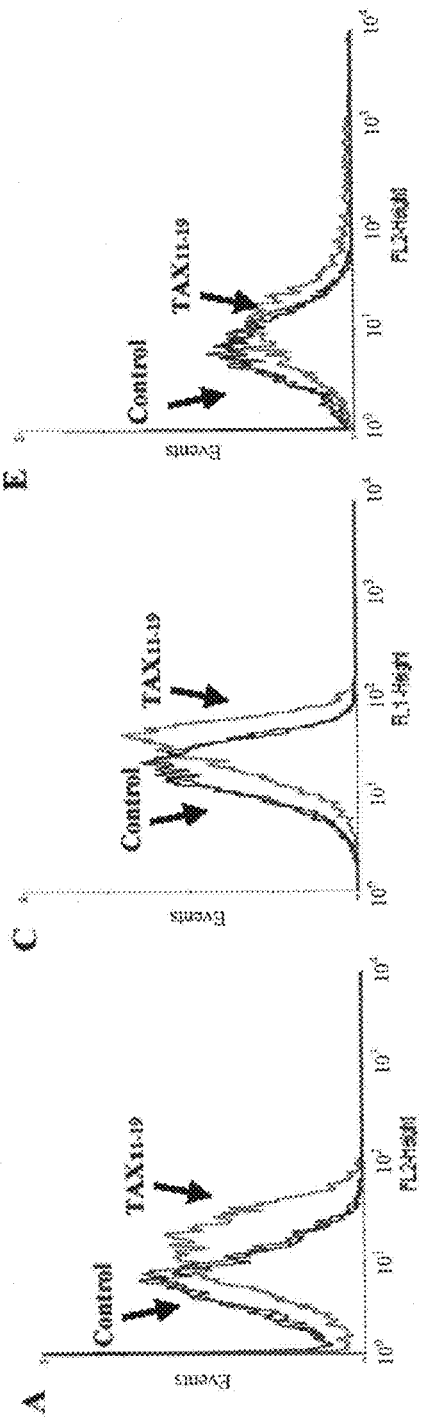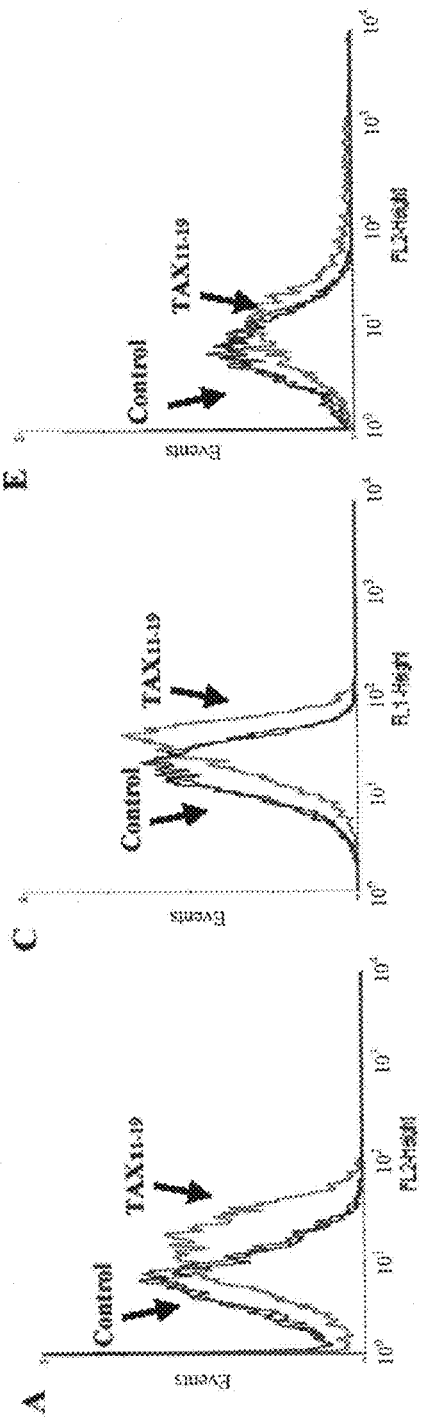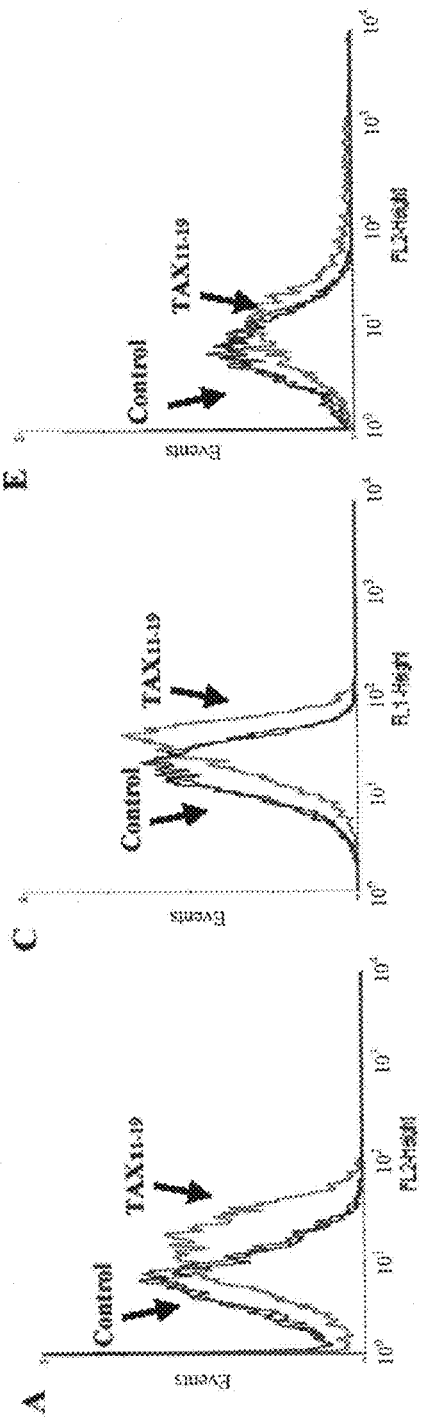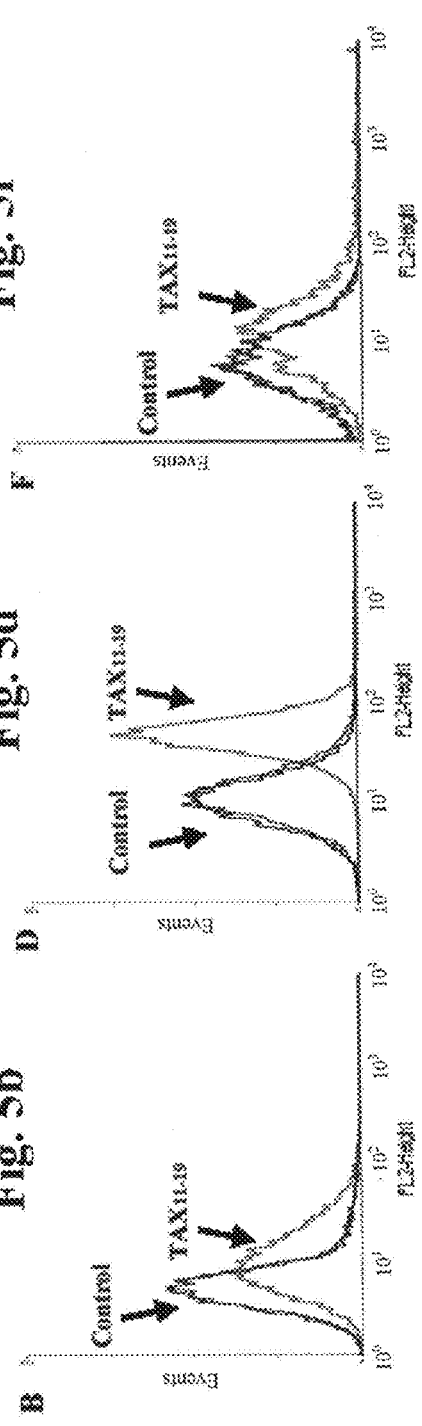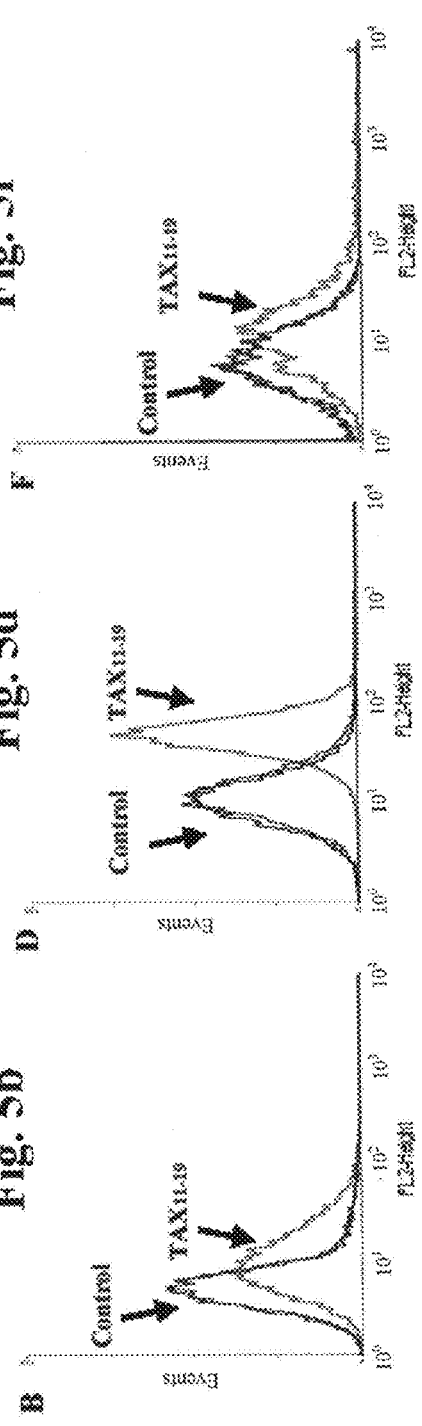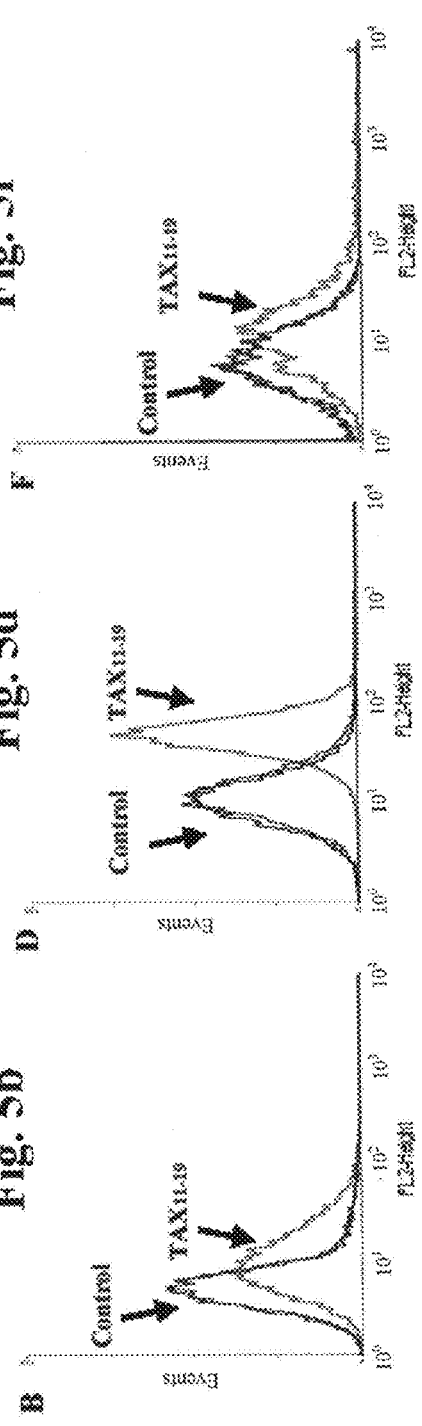

Fig. 8a
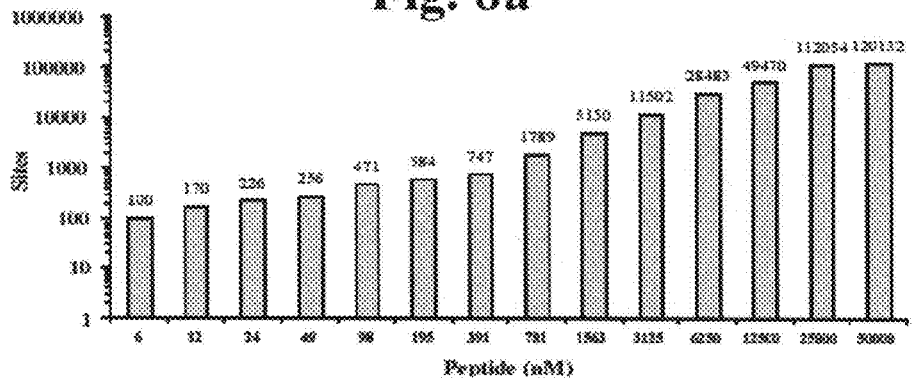
Fig. 8b
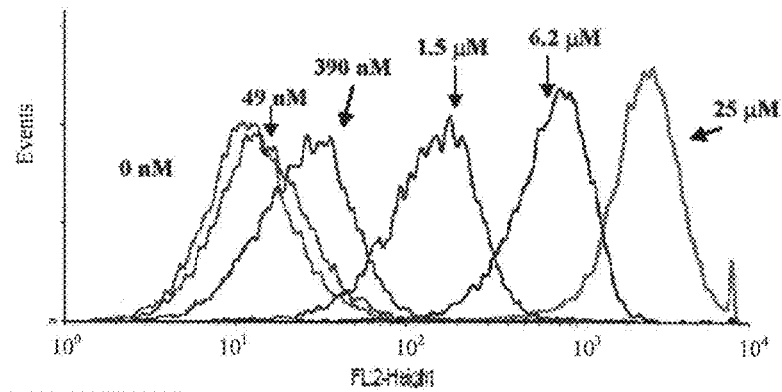
Fig. 8c
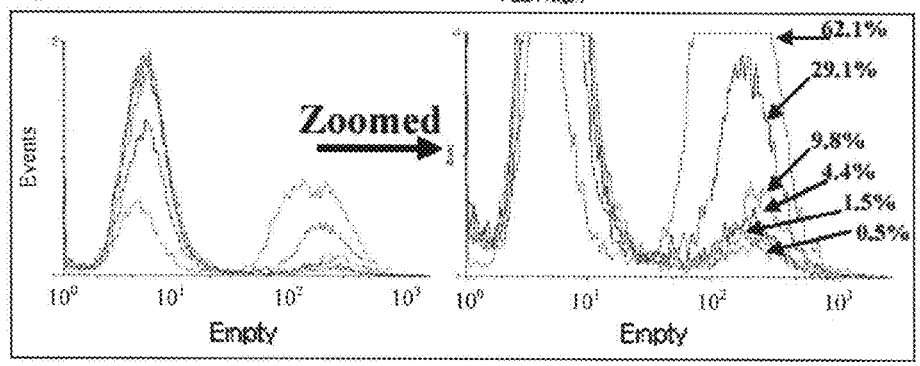
Fig. 8d
| Transfected cells within Heterogeneous population (%) | Positive cells detected within Heterogeneous population (%) | Detection sensitivity (Max=61.2% transfected) |
|---|---|---|
| 100 | 61.2 | 100 |
| 33 | 17.8 | 29.1 |
| 10 | 6.0 | 9.8 |
| 5 | 2.7 | 4.4 |
| 2.5 | 0.9 | 1.5 |
| 1 | 0.3 | 0.5 |

A  x40  JY/pCTAX

B  x60  JY/pCTAX

C  x40  JY/pCDNA

D  x40  JY/pCTAX

E  x40  APD/pCTAX

F  x40  APD/pCDNA

SEQUENCE LISTING

<160> NUMBER OF SEQ ID NOS: 97

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1

-continued agcggataac aatttcacac agg    23

<210> SEQ ID NO 2
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 2
tttgtcgtct ttccagacgt tagt    24

<210> SEQ ID NO 3
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 3

Leu Leu Phe Gly Tyr Pro Val Tyr Val
1               5

<210> SEQ ID NO 4
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 4

Leu Leu Leu Thr Val Leu Thr Val Val
1               5

<210> SEQ ID NO 5
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 5

Asn Leu Thr Ile Ser Asp Val Ser Val
1               5

<210> SEQ ID NO 6
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 6

Asn Leu Val Pro Met Val Ala Thr Val
1               5

<210> SEQ ID NO 7
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 7

Ser Val Arg Asp Arg Leu Ala Arg Leu
1               5

```
<210> SEQ ID NO 8
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 8

Ile Leu Ala Lys Phe Leu His Trp Leu
1               5

<210> SEQ ID NO 9
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 9

Arg Leu Val Asp Asp Phe Leu Leu Val
1               5

<210> SEQ ID NO 10
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 10

Ile Met Asp Gln Val Pro Phe Ser Val
1               5

<210> SEQ ID NO 11
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 11

Tyr Leu Glu Pro Gly Pro Val Thr Val
1               5

<210> SEQ ID NO 12
<211> LENGTH: 9
<212> TYPE: PRT
<213> ORGANISM: Artificial sequence
<220> FEATURE:
<223> OTHER INFORMATION: HLA-A2 restricted peptide

<400> SEQUENCE: 12

Lys Thr Trp Gly Gln Val Trp Gln Val
1               5

<210> SEQ ID NO 13
<211> LENGTH: 10
<212> TYPE: PRT
<213> ORGANISM: Artificial sequence
<220> FEATURE:
<223> OTHER INFORMATION: HLA-A2 restricted peptide

<400> SEQUENCE: 13

Glu Ala Ala Gly Ile Gly Ile Leu Thr Val
1               5                   10
```

```
<210> SEQ ID NO 14
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 14

Ser Tyr Thr Ile Ser
1               5

<210> SEQ ID NO 15
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 15

Gly Ile Ile Pro Ile Phe Gly Thr Ala Asn Tyr Ala Gln Lys Phe Gln
1               5                   10                  15

Gly

<210> SEQ ID NO 16
<211> LENGTH: 13
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 16

Asp Thr Asp Ser Ser Gly Tyr Tyr Gly Ala Val Asp Tyr
1               5                   10

<210> SEQ ID NO 17
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 17

Arg Ala Ser Gln Ser Val Gly Ser Tyr Leu Ala
1               5                   10

<210> SEQ ID NO 18
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 18

Asp Ala Ser His Arg Ala Thr
1               5

<210> SEQ ID NO 19
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.
```

```
<400> SEQUENCE: 19

Gln Gln Arg Ser Asn Trp Pro Pro Met Tyr Thr
1               5                   10

<210> SEQ ID NO 20
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 20

Ser Tyr Gly Met His
1               5

<210> SEQ ID NO 21
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 21

Val Ile Ser Tyr Asp Gly Ser Asn Lys Tyr Tyr Ala Asp Ser Val Lys
1               5                   10                  15

Gly

<210> SEQ ID NO 22
<211> LENGTH: 15
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 22

Asp Phe Asp Tyr Gly Asp Ser Tyr Tyr Tyr Tyr Gly Met Asp Val
1               5                   10                  15

<210> SEQ ID NO 23
<211> LENGTH: 12
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 23

Arg Ser Ser Gln Ser Leu Leu His Ser Asn Gly Tyr
1               5                   10

<210> SEQ ID NO 24
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 24

Leu Gly Ser Asn Arg Ala Ser
1               5
```

<210> SEQ ID NO 25
<211> LENGTH: 9
<212> TYPE: PRT
<213> ORGANISM: Artificial sequence
<220> FEATURE:
<223> OTHER INFORMATION: Sequence of complementarity determining region
    of Fab specifically binding HLA-A2:Tax11-19 complex.

<400> SEQUENCE: 25

Met Gln Ala Leu Gln Thr Pro Arg Thr
1               5

<210> SEQ ID NO 26
<211> LENGTH: 5
<212> TYPE: PRT
<213> ORGANISM: Artificial sequence
<220> FEATURE:
<223> OTHER INFORMATION: Sequence of complementarity determining region
    of Fab specifically binding HLA-A2:Tax11-19 complex.

<400> SEQUENCE: 26

Asn Tyr Gly Ile Asn
1               5

<210> SEQ ID NO 27
<211> LENGTH: 17
<212> TYPE: PRT
<213> ORGANISM: Artificial sequence
<220> FEATURE:
<223> OTHER INFORMATION: Sequence of complementarity determining region
    of Fab specifically binding HLA-A2:Tax11-19 complex.

<400> SEQUENCE: 27

Trp Ile Ser Ala Tyr Asn Gly Asp Thr Lys Tyr Ala Gln Arg Leu Gln
1               5                   10                  15

Asp

<210> SEQ ID NO 28
<211> LENGTH: 12
<212> TYPE: PRT
<213> ORGANISM: Artificial sequence
<220> FEATURE:
<223> OTHER INFORMATION: Sequence of complementarity determining region
    of Fab specifically binding HLA-A2:Tax11-19 complex.

<400> SEQUENCE: 28

Gly Asp Ser Thr Val Gly Tyr Glu Tyr Leu Gln Tyr
1               5                   10

<210> SEQ ID NO 29
<211> LENGTH: 11
<212> TYPE: PRT
<213> ORGANISM: Artificial sequence
<220> FEATURE:
<223> OTHER INFORMATION: Sequence of complementarity determining region
    of Fab specifically binding HLA-A2:Tax11-19 complex.

<400> SEQUENCE: 29

Gln Ala Ser Gln Gly Ile Gly Lys Tyr Leu Asn
1               5                   10

<210> SEQ ID NO 30
<211> LENGTH: 7
<212> TYPE: PRT
<213> ORGANISM: Artificial sequence
<220> FEATURE:
<223> OTHER INFORMATION: Sequence of complementarity determining region
    of Fab specifically binding HLA-A2:Tax11-19 complex.

```
<400> SEQUENCE: 30

Val Ala Ser Ser Leu Gln Ser
1               5

<210> SEQ ID NO 31
<211> LENGTH: 9
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 31

Gln Gln Thr Ser Ser Phe Pro Pro Thr
1               5

<210> SEQ ID NO 32
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 32

Ser Tyr Ala Ile Ser
1               5

<210> SEQ ID NO 33
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 33

Arg Ile Ile Pro Ile Leu Gly Ile Ala Asn Tyr Ala Gln Lys Phe Gln
1               5                   10                  15

Gly

<210> SEQ ID NO 34
<211> LENGTH: 14
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 co

<400> SEQUENCE: 34

Gln Gly Gly Asp Tyr Ser Asn Tyr Tyr Tyr Tyr Met Asp Val
1               5                   10

<210> SEQ ID NO 35
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 35

Arg Ala Ser Gln Ser Val Ser Ser Tyr Leu Ala
1               5                   10
```

```
<210> SEQ ID NO 36
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 36

Asp Ala Ser Asn Arg Ala Thr
1               5

<210> SEQ ID NO 37
<211> LENGTH: 9
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 37

Gln His Arg Phe Asn Trp Pro Val Thr
1               5

<210> SEQ ID NO 38
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 38

Ser Tyr Gly Met His
1               5

<210> SEQ ID NO 39
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 39

Val Ile Ser Tyr Asp Gly Ser Asn Lys Tyr Tyr Ala Asp Ser Val Lys
1               5                   10                  15

Gly

<210> SEQ ID NO 40
<211> LENGTH: 16
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 co

<400> SEQUENCE: 40

Asp Gln Thr Tyr Tyr Gly Ser Gly Ser Pro Arg Gly Gly Leu Asp Tyr
1               5                   10                  15

<210> SEQ ID NO 41
<211> LENGTH: 13
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.
```

```
<400> SEQUENCE: 41

Thr Gly Ser Ser Gly Ser Ile Ala Asn Asn Tyr Val Gln
1               5                   10

<210> SEQ ID NO 42
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 42

Glu Asp Asp Gln Arg Pro Ser
1               5

<210> SEQ ID NO 43
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 43

Gln Ser Tyr Asp Asn Ser Asn Ser Phe Val Val
1               5                   10

<210> SEQ ID NO 44
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 44

Ser Asn Ser Ala Ala Trp Asn
1               5

<210> SEQ ID NO 45
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 45

Arg Thr Tyr Tyr Arg Ser Lys Trp Tyr Asn Asp Tyr Val Ser Val Lys
1               5                   10                  15

Ser

<210> SEQ ID NO 46
<211> LENGTH: 15
<212> TYPE: PRT
<213> ORGANISM: Artificial sequence
<220> FEATURE:
<223> OTHER INFORMATION: Sequence of complementarity determining region of Fab
      specifically binding HLA-A2:Tax11-19 co

<400> SEQUENCE: 46

Gly Pro Tyr Asp Thr Thr Gly Pro Trp Gly Asn Trp Phe Asp Pro
1               5                   10                  15
```

```
<210> SEQ ID NO 47
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 47

Arg Ala Ser Gln Ser Val Ser Ser Asp Leu Ala
1               5                   10

<210> SEQ ID NO 48
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 48

Gly Ala Ser Tyr Arg Ala Thr
1               5

<210> SEQ ID NO 49
<211> LENGTH: 9
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 49

Gln Gln Tyr Gly Ser Ser Pro Arg Thr
1               5

<210> SEQ ID NO 50
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 50

Ser Tyr Gly Met His
1               5

<210> SEQ ID NO 51
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 51

Val Ile Ser Tyr Asp Gly Ser Asn Lys Tyr Tyr Ala Asp Ser Val Lys
1               5                   10                  15

Gly

<210> SEQ ID NO 52
<211> LENGTH: 15
<212> TYPE: PRT
<213> ORGANISM: Artificial sequence
<220> FEATURE:
<223> OTHER INFORMATION: Sequence of complementarity determining region of Fab
      specifically binding HLA-A2:Tax11-19 co
```

<400> SEQUENCE: 52

Asp Phe Asp Tyr Gly Asp Ser Tyr Tyr Tyr Gly Met Asp Val
1               5                   10                  15

<210> SEQ ID NO 53
<211> LENGTH: 16
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 53

Arg Ser Ser Gln Ser Leu Leu His Ser Asn Gly Tyr Asn Tyr Leu Asp
1               5                   10                  15

<210> SEQ ID NO 54
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 54

Leu Gly Ser Asn Arg Ala Ser
1               5

<210> SEQ ID NO 55
<211> LENGTH: 9
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 55

Met Gln Ala Leu Gln Thr Pro Arg Thr
1               5

<210> SEQ ID NO 56
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 56

Ser Tyr Ala Met Ser
1               5

<210> SEQ ID NO 57
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 57

Ala Ile Ser Gly Ser Gly Gly Ser Thr Tyr Tyr Ala Asp Ser Val Lys
1               5                   10                  15
Gly

```
<210> SEQ ID NO 58
<211> LENGTH: 13
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 co

<400> SEQUENCE: 58

Asp Ser Leu Ala Gly Ala Thr Gly Thr Asp Phe Asp Tyr
1               5                   10

<210> SEQ ID NO 59
<211> LENGTH: 12
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 59

Arg Ala Ser Gln Thr Val Thr Ala Asn Tyr Leu Ala
1               5                   10

<210> SEQ ID NO 60
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 60

Asp Ala Ser Val Arg Ala Thr
1               5

<210> SEQ ID NO 61
<211> LENGTH: 9
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 61

Gln Gln Tyr Gly Ser Ser Pro Ile Thr
1               5

<210> SEQ ID NO 62
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 62

Ser Tyr Ala Met Ser
1               5

<210> SEQ ID NO 63
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 63
```

```
Gly Ile Ser Gly Ser Gly Gly Ser Thr Tyr Tyr Ala Asp Ser Val Lys
1               5                   10                  15

Gly

<210> SEQ ID NO 64
<211> LENGTH: 14
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 co

<400> SEQUENCE: 64

Asp Phe Asp Tyr Gly Gly Asn Ser Gly Ser Leu Phe Asp Tyr
1               5                   10

<210> SEQ ID NO 65
<211> LENGTH: 12
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 65

Gly Ala Ser Glu Ser Val Gly Gly Asn Tyr Leu Ala
1               5                   10

<210> SEQ ID NO 66
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 66

Asp Ala Ser Thr Arg Ala Thr
1               5

<210> SEQ ID NO 67
<211> LENGTH: 10
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 67

Gln His Tyr Gly Ser Ser Pro Ser Thr Tyr
1               5                   10

<210> SEQ ID NO 68
<211> LENGTH: 6
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 68

Ser Ser Asn Trp Trp Ser
1               5

<210> SEQ ID NO 69
<211> LENGTH: 16
```

```
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 69

Glu Ile Tyr His Ser Gly Ser Thr Asn Tyr Asn Pro Ser Leu Lys Ser
1               5                   10                  15

<210> SEQ ID NO 70
<211> LENGTH: 14
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 70

His Ser Tyr Asp Tyr Leu Trp Gly Thr Tyr Arg Phe Asp Tyr
1               5                   10

<210> SEQ ID NO 71
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 71

Arg Ala Ser Gln Asp Ile Gly Thr Trp Leu Ala
1               5                   10

<210> SEQ ID NO 72
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 72

Ala Ala Thr Thr Leu Glu Ser
1               5

<210> SEQ ID NO 73
<211> LENGTH: 9
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 73

Gln Gln Ala Arg Ser Leu Pro Tyr Thr
1               5

<210> SEQ ID NO 74
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 74

Asn Tyr Gly Ile Asn
```

```
1               5

<210> SEQ ID NO 75
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 75

Trp Ile Ser Ala Tyr Asn Gly Asp Thr Lys Tyr Ala Gln Arg Leu Gln
1               5                   10                  15
Asp

<210> SEQ ID NO 76
<211> LENGTH: 12
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 76

Gly Asp Ser Thr Val Gly Tyr Glu Tyr Leu Gln Tyr
1               5                   10

<210> SEQ ID NO 77
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 77

Gln Ala Ser Gln Gly Ile Gly Lys Tyr Leu Asn
1               5                   10

<210> SEQ ID NO 78
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 78

Val Ala Ser Ser Leu Gln Ser
1               5

<210> SEQ ID NO 79
<211> LENGTH: 9
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 79

Gln Gln Thr Ser Ser Phe Pro Pro Thr
1               5

<210> SEQ ID NO 80
<211> LENGTH: 5
<212> TYPE: PRT
<213> ORGANISM: Artificial sequence
```

```
<220> FEATURE:
<223> OTHER INFORMATION: Sequence of complementarity determining region
      of Fab specifically binding HLA-A2:Tax11-19 complex.

<400> SEQUENCE: 80

Ser Tyr Gly Met His
1               5

<210> SEQ ID NO 81
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 81

Val Ile Ser Tyr Asp Gly Ser Asn Lys Tyr Tyr Ala Asp Ser Val Lys
1               5                   10                  15

Gly

<210> SEQ ID NO 82
<211> LENGTH: 12
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 82

Asp Tyr Asn Gly Tyr Gly Asp Tyr Val Leu Gly Tyr
1               5                   10

<210> SEQ ID NO 83
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 83

Arg Ala Ser Gln Ser Val Ser Ser Tyr Leu Ala
1               5                   10

<210> SEQ ID NO 84
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 84

Asp Ala Ser Asn Arg Ala Thr
1               5

<210> SEQ ID NO 85
<211> LENGTH: 10
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 85

Gln Gln Arg Ser Asn Trp Ala Ser Tyr Thr
```

```
<210> SEQ ID NO 86
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 86

Ser Tyr Tyr Met His
1               5

<210> SEQ ID NO 87
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 87

Ile Ile Asn Pro Ser Gly Gly Ser Thr Ser Tyr Ala Gln Lys Phe Gln
1               5                   10                  15

Gly

<210> SEQ ID NO 88
<211> LENGTH: 15
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 88

Asp Arg Gly Gly Gly Tyr Asp Val Ser Pro Tyr Gly Met Asp Val
1               5                   10                  15

<210> SEQ ID NO 89
<211> LENGTH: 11
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 89

Arg Ala Ser Gln Ser Ile Ser Ser Tyr Leu Asn
1               5                   10

<210> SEQ ID NO 90
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 90

Ala Ala Ser Asn Leu Gln Thr
1               5

<210> SEQ ID NO 91
<211> LENGTH: 8
<212> TYPE: PRT
<213> ORGANISM: Artificial sequence
```

```
<220> FEATURE:
<223> OTHER INFORMATION: Sequence of complementarity determining region
      of Fab specifically binding HLA-A2:Tax11-19 complex.

<400> SEQUENCE: 91

Gln Gln Thr Tyr Ser Leu Pro Thr
1               5

<210> SEQ ID NO 92
<211> LENGTH: 5
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 92

Ser Tyr Ala Ile Ser
1               5

<210> SEQ ID NO 93
<211> LENGTH: 17
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 93

Gly Ile Ile Pro Ile Pro Gly Ile Thr Asn Tyr Ala Gln Lys Phe Gln
1               5                   10                  15

Gly

<210> SEQ ID NO 94
<211> LENGTH: 10
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 94

Arg Val Gly Tyr Tyr Tyr Gly Met Asp Val
1               5                   10

<210> SEQ ID NO 95
<211> LENGTH: 13
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 95

Ala Gly Ser Gly Gly Asp Ile Ala Ser Asn Phe Val Gln
1               5                   10

<210> SEQ ID NO 96
<211> LENGTH: 7
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 96

Glu Glu Asn Arg Arg Pro Ser
```

```
<210> SEQ ID NO 97
<211> LENGTH: 8
<212> TYPE: PRT
<213> ORGANISM: Artificial sequence
<220> FEATURE:
<223> OTHER INFORMATION: Sequence of complementarity determining region
      of Fab specifically binding HLA-A2:Tax11-19 complex.

<400> SEQUENCE: 97

Gln Ser Tyr Asp Gly Ser Ala Trp
1               5
```

ANTIGEN-PRESENTING COMPLEX-BINDING COMPOSITIONS AND USES THEREOF

This application is a National Phase Application of PCT/IL2004/000275 having International Filing Date of 25 Mar. 2004, which is a Continuation-in-Part of U.S. patent application Ser. No. 10/396,578 filed 26 Mar. 2003 now abandoned.

FIELD AND BACKGROUND OF THE INVENTION

The present invention relates to compositions-of-matter capable of specifically binding particular antigen-presenting molecule (APM):antigen complexes. More particularly, the present invention relates to compositions-of-matter capable of specifically binding a particular human APM:pathogen-derived antigen complex.

Diseases caused by pathogens, such as viruses, mycoplasmas, bacteria, fungi, and protozoans, account for a vast number of diseases, including highly debilitating/lethal diseases, affecting all human individuals at numerous instances during their lifetime. For example, diseases caused by retroviruses are associated with various immunological, neurological, and neoplastic disorders. For example, diseases caused by lymphotropic retroviruses, such as acquired immunodeficiency syndrome (AIDS) caused by human immunodeficiency virus (HIV), or the closely related human T-cell lymphotropic virus (HTLV), a causative agent of various lethal pathologies (for general references, refer, for example to: Johnson J M. et al., 2001. Int J Exp Pathol. 82:135-47; and Bangham C R., 2000. J Clin Pathol. 53:581-6), account for lethal disease epidemics of devastating human and economic impact.

However, satisfactory methods of diagnosing, characterizing, and treating many kinds of pathogen-associated diseases such as diseases associated with lymphotropic viruses such as HIV or HTLV are unavailable.

HTLV-1 was the first human retrovirus identified (Poiesz B. J. et al., 1980. Proc Natl Acad Sci USA. 77:7415-7419). It infects both CD4+ and CD8+ T-lymphocytes and is associated with a variety of diseases, including adult T-lymphocyte leukemia/lymphoma (ATLL; Yoshida M. et al., 1982. Proc Natl Acad Sci USA. 79:2031-2035) and a non neoplasic inflammatory neurological syndrome called human T lymphotropic type I (HTLV-1)-associated myelopathy/tropical virus spastic paraparesis (HAM/TSP; Osame M. et al., 1986. Lancet 1:1031-1032; reviewed in Ribas J G. and Melo G C., 2002. Rev Soc Bras Med Trop. 35:377-84; and Plumelle Y., 1999. Med Hypotheses. 52:595-604). Other diseases linked to HTLV-1 infection on the basis of seroepidemiological studies include Sjogren's syndrome, inflammatory arthropathies, polymyositis, and pneumopathies (Coscoy L. et al., 1998. Virology 248: 332-341). The HTLV protein Tax seems to play a major role in the pathogenesis of HTLV-1 associated diseases. Tax protein is known to stimulate the transcription of viral and cellular genes such as the genes coding for interleukin-2 (IL-2) and other cytokines, interleukin-2 receptor (IL-2R), proto-oncogenes, c-jun and c-fos, and major histocompatibility complex (MHC) molecules (Yoshida M., 1993. Trends Microbiol. 1:131-135). The transforming potential of Tax has been demonstrated in different experimental systems. It has been shown that rodent fibroblastic cell lines expressing Tax form colonies in soft agar and tumors in nude mice (Tanaka A. et al., 1990. Proc Natl Acad Sci USA. 87:1071-1075). Also, Tax transforms primary fibroblasts in cooperation with the Ras protein (Pozzatti R. et al., 1990. Mol Cell Biol. 10:413-417), and immortalizes primary T-lymphocytes in the presence of IL-2 (Grassmann R. et al., 1989. Proc Natl Acad Sci USA. 86:3351-3355). Transgenic mice carrying the tax gene develop different types of tumors (Grossman W. J. et al., 1995. Proc Natl Acad Sci USA. 92:1057-1061). Tax binds directly to DNA but acts in cooperation with several cellular transcription factors, but the role of these different interactions in the cell transformation mediated by Tax is still unclear (Coscoy L. et al., 1998. Virology 248: 332-341).

HAM/TSP is a progressive chronic demyelinating disorder affecting the white matter of the central nervous system (CNS) and the spinal cord. The disease affects approximately twice as many females as males, and typically the time of disease onset occurs during the fourth decade of life. The disease causes numerous highly debilitating symptoms, with common early symptoms and signs including gait disturbance and weakness and stiffness of the lower limbs. The disease affects the lower extremities to a much greater degree than upper extremities, spasticity may be moderate to severe, and lower back pain commonly occurs. Disease progression is associated with bowel and bladder dysfunction, and sensory loss and dysesthesia. Patients examined via magnetic resonance imaging may exhibit nonspecific lesions in the brain as well as spinal cord atrophy. Immune manifestations associated with HAM/TSP include inflammatory infiltrates in the central nervous system consisting predominantly of monocytes, and large numbers of CD8+ T-cells which are primarily reactive with peptides of the HTLV-1 Tax protein. The frequency of such T-cells in the peripheral blood and cerebrospinal fluid (CSF) has been shown to be proportional to the amount of HTLV-1 proviral load and the levels of HTLV-1 tax mRNA expression. It has further been shown that in patients carrying the HLA-A2 allele, the immune response is dominated by CD8+ T-lymphocytes that recognize the $Tax_{11-19}$ peptide (Bieganowska K. et al., 1999. J Immunol. 162:1765-1771; Nagai, M. et al., 2001. J Inf Dis. 183:197-205). Thus, immunological determinants, such as the $Tax_{11-19}$ peptide and antigenic mimics thereof, shared by thymus, brain and HTLV-1 are thought to direct lymphocytic neurotropism and demyelinization in nervous tissues. It is thought that the specificity of thoracic spinal cord involvement could be linked to shared thymic and thoracic spinal cord determinants, genetically peculiar to HAM/TSP patients. In a first stage, disease onset may be dependent on CD4+ T-lymphocytes specific for such determinants, reactivated in response to HTLV-1 infection, and that demyelinization during this stage could potentially be initiated as a result of stoppage in the synthesis of myelin following alteration of expression of oligodendrocytic and neuronal adhesion molecules. The second stage of the disease, involving chronic inflammatory manifestations, may depend on CD8+ T-lymphocytes specific for viral peptides, but also on CD8+ T-lymphocytes specific for peptides generated as a result of proteolysis of myelin layer, and other central nervous system proteins.

While, at best, therapy of HAM/TSP with corticosteroids, and IFN-gamma may result transient responses, similarly to numerous diseases associated with lymphotropic viruses there is currently no effective treatment for HAM/TSP, nor does the state of the art currently enable optimal prediction, diagnosis, staging, monitoring, and prognosis of the disease in patients.

The immune system employs two types of immune responses to provide antigen specific protection from pathogens; humoral immune responses, and cellular immune, responses, which involve specific recognition of pathogen antigens via antibodies and T-lymphocytes, respectively.

T-lymphocytes, by virtue of being the antigen specific effectors of cellular immunity, play a central and direct role in the body's defense against diseases mediated by intracellular pathogens, such as viruses, intracellular bacteria, mycoplasmas, and intracellular parasites, by directly cytolysing cells infected by such pathogens. However, helper T-lymphocytes also play a critical role in humoral immune responses against non intracellular pathogens by providing T-cell help to B lymphocytes in the form of interleukin secretion to stimulate production of antibodies specific for antigens of such pathogens.

The specificity of T-lymphocyte responses is conferred by, and activated through T-cell receptors (TCRs). T-cell receptors are antigen specific receptors clonally distributed on individual T-lymphocytes whose repertoire of antigenic specificity is generated via somatic gene rearrangement mechanisms analogously to those involved in generating the antibody gene repertoire. T-cell receptors are composed of a heterodimer of transmembrane molecules, the main type being composed of an alpha-beta dimer and a smaller subset of a gamma-delta dimer. T-lymphocyte receptor subunits comprise a transmembrane constant region and a variable region in the extracellular domain, similarly to immunoglobulins, and signal transduction triggered by TCRs is indirectly mediated via CD3/zeta, an associated multi-subunit complex comprising signal transducing subunits.

The two main classes of T-lymphocytes, helper T-lymphocytes and cytotoxic T-lymphocytes (CTLs), are distinguished by expression of the surface markers CD4 and CD8, respectively. As described hereinabove, the main function of helper T-lymphocytes is to secrete cytokines, such as IL-2, promoting activation and proliferation of CTLs and B lymphocytes, and the function of CTLs is to induce apoptotic death of cells displaying immunogenic antigens.

T-lymphocyte receptors, unlike antibodies, do not recognize native antigens but rather recognize cell-surface displayed complexes comprising an intracellularly processed fragment of a protein or lipid antigen in association with a specialized antigen-presenting molecule (APM): major histocompatibility complex (MHC) for presentation of peptide antigens; and CD1 for presentation of lipid antigens, and to a lesser extent, peptide antigens. Peptide antigens displayed by MHC molecules and lipid antigens displayed by CD1 molecules have characteristic chemical structures are referred to as MHC-restricted peptides and CD1 restricted lipids, respectively. Major histocompatibility complex molecules are highly polymorphic, comprising more than 40 common alleles for each individual gene. "Classical" MHC molecules are divided into two main types, class I and class II, having distinct functions in immunity.

Major histocompatibility complex class I molecules are expressed on the surface of virtually all cells in the body and are dimeric molecules composed of a transmembrane heavy chain, comprising the peptide antigen binding cleft, and a smaller extracellular chain termed $\beta_2$-microglobulin. MHC class I molecules present 9- to 11-amino acid residue peptides derived from the degradation of cytosolic proteins by the proteasome a multi-unit structure in the cytoplasm, (Niedermann G., 2002. Curr Top Microbiol Immunol. 268:91-136; for processing of bacterial antigens, refer to Wick M J, and Ljunggren H G., 1999. Immunol Rev. 172:153-62). Cleaved peptides are transported into the lumen of the endoplasmic reticulum (ER) by TAP where they are bound to the groove of the assembled class I molecule, and the resultant MHC:antigen complex is transported to the cell membrane to enable antigen presentation to T-lymphocytes (Yewdell J W., 2001. Trends Cell Biol. 11:294-7; Yewdell J W. and Bennink J R., 2001. Curr Opin Immunol. 13:13-8).

Major histocompatibility complex class II molecules are expressed on a restricted subset of specialized antigen-presenting cells (APCs) involved in T-lymphocyte maturation and priming. Such APCs in particular include dendritic cells and macrophages, cell types which internalize, process and display antigens sampled from the extracellular environment. Unlike MHC class I molecules, MHC class II molecules are composed of an alpha-beta transmembrane dimer whose antigen binding cleft can accommodate peptides of about 10 to 30, or more, amino acid residues.

The antigen presenting molecule CD1, whose main function, as described hereinabove, is presentation of lipid antigens, is a heterodimer comprising a transmembrane heavy chain paired with beta$_2$-microglobulin, similarly to MHC class I, and is mainly expressed on professional APCs, similarly to MHC class II (Sugita M. and Brenner M B., 2000. Semin Immunol. 12:511). CD1:antigen complexes are specifically recognized by TCRs expressed on CD4$^-$CD8$^-$ T-lymphocytes and NKT lymphocytes and play a significant role in microbial immunity, tumor immunology, and autoimmunity.

The cells of the body are thus scanned by T-lymphocytes during immune surveillance or during maturation of T-lymphocytes for their intracellular protein or lipid content in the form of such APM:antigen complexes.

One strategy which has been proposed to enable optimal diagnosis, characterization, and treatment of diseases, such as HAM/TSP, associated with an infection by a pathogen involves using molecules capable of specifically binding APM:antigen complexes composed of a particular combination of APM and an antigen derived from such a pathogen. Such molecules, for example, could be conjugated to functional moieties, such as detectable moieties or toxins, and the resultant conjugates could be used to detect such complexes or cells displaying such complexes, or to kill cells displaying such complexes. Hence, such conjugates could be used to diagnose/characterize and treat a pathogen infection in an individual, respectively. Alternately, molecules capable of specifically binding such complexes could be used to bind such complexes on cells so as to block activation of T-lymphocytes bearing. TCRs specific for such complexes. Such molecules could further be used, for example, to isolate such complexes, or cells displaying such complexes, such as cells infected with a pathogen, or APCs exposed to a pathogen-derived antigen.

Several prior art approaches have been described involving molecules capable of binding particular APM:antigen complexes.

One approach involves using TCRs or derivatives thereof specific for particular MHC:peptide complexes in attempts to provide reagents capable of specifically binding such complexes.

Another approach involves using antibodies or derivatives thereof specific for particular mouse MHC:peptide complexes in attempts to provide reagents capable of specifically binding such complexes (Aharoni, R. et al., 1991. Nature 351:147-150; Andersen, P. S. et al., 1996. Proc. Natl. Acad. Sci. U.S.A 93:1820-1824; Dadaglio, G. et al., 1997. Immunity 6:727-738; Day, P. M. et al., 1997. Proc. Natl. Acad. Sci. U.S.A. 94:8064-8069; Krogsgaard, M. et al., 2000. J. Exp. Med. 191:1395-1412; Murphy, D. B. et al., 1989. Nature 338:765-768; Porgador, A. et al., 1997. Immunity 6:715-726; Reiter, Y. et al., Proc. Natl. Acad. Sci. U.S.A. 94:4631-4636; Zhong, G. et al., 1997. Proc. Natl. Acad. Sci. U.S.A. 94:13856-13861; Zhong, G. et al., 1997. J. Exp. Med. 186: 673-682).

A further approach involves utilizing antibodies or derivatives thereof specific for the human MHC class I molecule HLA-A1 in complex with an HLA-A1 restricted peptide derived from the melanoma specific tumor associated antigen melanoma associated antigen (MAGE)-A1 in attempts to provide reagents capable of specifically binding such a complex (Chames, P. et al., 2000. Proc. Natl. Acad. Sci. U.S.A. 97:7969-7974).

An additional approach involves employing antibodies or derivatives thereof specific for the human MHC class I molecule HLA-A2 in complex with an HLA-A2 restricted peptide derived from the melanoma specific tumor associated antigen gp100 in attempts to provide reagents capable of specifically binding such a complex (Denkberg, G. et al., 2002. Proc. Natl. Acad. Sci. U.S.A. 99:9421-9426).

Yet another approach involves using antibodies or derivatives thereof specific for human MHC class I molecule HLA-A2 in complex with an HLA-A2 restricted peptide derived from human telomerase catalytic subunit (hTERT) in attempts to provide reagents capable of specifically binding such a complex (Lev, A. et al., 2002. Cancer Res. 62:3184-3194).

However, all of the aforementioned prior art approaches suffer from significant disadvantages: (i) approaches involving the use TCRs or portions thereof as compounds capable of specifically binding particular MHC:peptide complexes are suboptimal due to the relatively low intrinsic binding affinity of TCRs for such complexes; (ii) approaches involving the use of antibodies or portions thereof specific for MHC:peptide complexes comprising non-human MHC are not suitable for human application; and (iii) approaches involving antibodies or portions thereof specific for MHC:non-pathogen-derived antigen complexes are not suitable for specifically binding complexes comprising pathogen-derived antigens.

Thus, all prior art approaches have failed to provide an adequate solution for providing molecules capable of specifically binding with high specificity and affinity a particular human APM:pathogen-derived antigen complex.

There is thus a Widely recognized need for, and it would be highly advantageous to have, molecules devoid of the above limitation.

SUMMARY OF THE INVENTION

According to one aspect of the present invention there is provided a method of detecting an antigen-presenting portion of a complex composed of a human antigen-presenting molecule and an antigen derived from a pathogen, the method comprising: (a) exposing the antigen-presenting portion of the complex to a composition-of-matter comprising an antibody or antibody fragment including an antigen-binding region capable of specifically binding the antigen-presenting portion of the complex, to thereby obtain a conjugate of the antigen-presenting portion of the complex and the antibody or antibody fragment; and (b) detecting the antibody or antibody fragment of the conjugate, thereby detecting an antigen-presenting portion of a complex composed of a human antigen-presenting molecule and an antigen derived from a pathogen.

According to further features in preferred embodiments of the invention described below, the complex is displayed or expressed by a target cell, and step (a) is effected by exposing the target to the composition-of-matter.

According to still further features in the described preferred embodiments the method of detecting an antigen-presenting portion of a complex composed of a human antigen-presenting molecule and an antigen derived from a pathogen further comprises: (c) obtaining the target cell from an individual.

According to another aspect of the present invention there is provided a method of detecting in a biological sample an antigen-presenting portion of a complex composed of an antigen-presenting molecule and an antigen, the method comprising: (a) attaching the biological sample to a surface; (b) exposing the biological sample to a composition-of-matter comprising an antibody or antibody fragment including an antigen-binding region capable of specifically binding the antigen-presenting portion of the complex, to thereby obtain a conjugate of the antigen-presenting portion of the complex and the antibody or antibody fragment; and (c) detecting the antibody or antibody fragment of the conjugate, thereby detecting in a biological sample an antigen-presenting portion of a complex composed of a human antigen-presenting molecule and an antigen.

According to further features in preferred embodiments of the invention described below, the he method of detecting in a biological sample an antigen-presenting portion of a complex composed of an antigen-presenting molecule and an antigen further comprises: (d) obtaining the biological sample from an individual.

According to still further features in the described preferred embodiments, step (b) is effected by administering the composition-of-matter to an individual.

According to still further features in the described preferred embodiments, the antigen is derived from a pathogen.

According to still further features in the described preferred embodiments, the biological sample is infected with the pathogen.

According to still further features in the described preferred embodiments, the biological sample is a cell sample or a tissue sample.

According to yet another aspect of the present invention there is provided a method of diagnosing an infection by a pathogen in an individual, the method comprising: (a) exposing a target cell of the individual to a composition-of-matter comprising an antibody or antibody fragment including an antigen-binding region capable of specifically binding an antigen-presenting portion of a complex composed of a human antigen-presenting molecule and an antigen derived from the pathogen, to thereby obtain a conjugate of the antigen-presenting portion of the complex and the antibody or antibody fragment; and (b) detecting the antibody or antibody fragment of the conjugate, thereby diagnosing an infection by a pathogen in an individual.

According to further features in preferred embodiments of the invention described below, the method of diagnosing an infection by a pathogen in an individual further comprises: (c) obtaining the target cell from the individual.

According to still further features in the described preferred embodiments, step (a) is effected by administering the composition-of-matter to the individual.

According to still further features in the described preferred embodiments, the composition-of-matter further comprises a detectable moiety attached to the antibody or antibody fragment, and detecting the antibody or antibody fragment of the conjugate is effected by detecting the detectable moiety attached to the antibody or antibody fragment of the conjugate.

According to still another aspect of the present invention there is provided a method of killing or damaging a target cell expressing or displaying an antigen-presenting portion of a complex composed of a human antigen-presenting molecule and an antigen derived from a pathogen, the method comprising exposing the target cell to a composition-of-matter comprising an antibody or antibody fragment including an antigen-binding region capable of specifically binding the antigen-presenting portion of the complex, thereby killing or damaging a target cell expressing or displaying an antigen-presenting portion of a complex composed of a human antigen-presenting molecule and an antigen derived from a pathogen.

According to further features in preferred embodiments of the invention described below, the method of killing or damaging a target cell expressing or displaying an antigen-presenting portion of a complex composed of a human antigen-presenting molecule and an antigen derived from a pathogen further comprises the step of obtaining the target cell from an individual.

According to still further features in the described preferred embodiments, exposing the target cell to the composition-of-matter is effected by administering the composition-of-matter to an individual.

According to still further features in the described preferred embodiments, the target cell is infected with the pathogen.

According to still further features in the described preferred embodiments, the target cell is a T-lymphocyte or an antigen presenting cell.

According to still further features in the described preferred embodiments, the antigen presenting cell is a B cell or a dendritic cell.

According to a further aspect of the present invention there is provided a method of treating a disease associated with a pathogen in an individual, the method comprising administering to the individual a therapeutically effective amount of a pharmaceutical composition comprising as an active ingredient, a composition-of-matter comprising an antibody or antibody fragment including an antigen-binding region capable of specifically binding an antigen-presenting portion of a complex composed of a human antigen-presenting molecule and an antigen derived from the pathogen, thereby treating a disease associated with a pathogen in an individual.

According to a yet a further aspect of the present invention there is provided an isolated polynucleotide comprising a first nucleic acid sequence encoding an antibody fragment, the antibody fragment including an antigen-binding region capable of specifically binding an antigen-presenting portion of a complex composed of a human antigen-presenting molecule and an antigen derived from a pathogen.

According to further features in preferred embodiments of the invention described below, the isolated polynucleotide further comprises a second nucleic acid sequence encoding a polypeptide selected from the group consisting of a coat protein of a virus, a detectable moiety, and a toxin.

According to still further features in the described preferred embodiments, the second nucleic acid sequence is translationally fused with the first nucleic acid sequence.

According to still a further aspect of the present invention there is provided a nucleic acid construct comprising the isolated polynucleotide and a promoter sequence for directing transcription of the isolated polynucleotide in a host cell.

According to further features in preferred embodiments of the invention described below, the promoter sequence is a T7 promoter sequence.

According to still further features in the described preferred embodiments, the promoter sequence is capable of driving expression of the nucleic acid sequence in a prokaryote.

According to still further features in the described preferred embodiments, the promoter sequence is capable of driving inducible expression of the nucleic acid sequence.

According to an additional aspect of the present invention there is provided a host cell comprising the nucleic acid construct.

According to further features in preferred embodiments of the invention described below, the host cell is a prokaryotic cell.

According to still further features in the described preferred embodiments, the prokaryotic cell is an *E. coli* cell.

According to yet an additional aspect of the present invention there is provided a virus comprising the nucleic acid construct.

According to still an additional aspect of the present invention there is provided a virus comprising a coat protein fused to an antibody fragment including an antigen-binding region capable of specifically binding an antigen-presenting portion of a complex composed of a human antigen-presenting molecule and an antigen derived from a pathogen.

According to further features in preferred embodiments of the invention described below, the virus is a filamentous phage and the coat protein is pIII.

According to another aspect of the present invention there is provided a composition-of-matter comprising an antibody or antibody fragment including an antigen-binding region capable of specifically binding an antigen-presenting portion of a complex composed of a human antigen-presenting molecule and an antigen derived from a pathogen.

According to yet another aspect of the present invention there is provided a pharmaceutical compositions comprising as an active ingredient the composition-of-matter and a pharmaceutically acceptable carrier.

According to still another aspect of the present invention there is provided a composition-of-matter comprising a multimeric form of an antibody or antibody fragment including an antigen-binding region capable of specifically binding an antigen-presenting portion of a complex composed of a human antigen-presenting molecule and an antigen derived from a pathogen.

According to a further aspect of the present invention there is provided a pharmaceutical composition comprising as an active ingredient the composition-of-matter comprising a multimeric form of an antibody or antibody fragment including an antigen-binding region capable of specifically binding an antigen-presenting portion of a complex composed of a human antigen-presenting molecule and an antigen derived from a pathogen, and a pharmaceutically acceptable carrier.

According to, further features in preferred embodiments of the invention described below, the antibody is a monoclonal antibody.

According to still further features in the described preferred embodiments, the antibody fragment is a monoclonal antibody fragment.

According to still further features in the described preferred embodiments, the antibody fragment is selected from the group consisting of an Fd fragment, an Fab, and a single chain Fv.

According to still further features in the described preferred embodiments, the antigen-binding region includes an amino acid sequence selected from the group consisting of SEQ ID NOs: 14 to 97.

According to still further features in the described preferred embodiments, the antibody or antibody fragment, or a part of the antibody or antibody fragment is of human origin.

According to still further features in the described preferred embodiments, the part of the antibody or antibody fragment is a portion of a constant region of the antibody or antibody fragment, or a constant region of the antibody or antibody fragment.

According to still further features in the described preferred embodiments, the binding of the antibody or antibody fragment to the antigen-presenting portion of the complex is characterized by an affinity having a dissociation constant selected from the range consisting of $1 \times 10^{-2}$ molar to $5 \times 10^{-16}$ molar.

According to still further features in the described, preferred embodiments, the composition-of-matter further comprises a toxin or detectable moiety attached to the antibody or antibody fragment.

According to still further features in the described preferred embodiments, the detectable moiety is selected from the group consisting of a recognition sequence of a biotin protein ligase, a biotin molecule, a streptavidin molecule, a fluorophore, an enzyme, and a polyhistidine tag.

According to still further features in the described preferred embodiments, the biotin protein ligase is BirA.

According to still further features in the described preferred embodiments, the fluorophore is phycoerythrin.

According to still further features in the described preferred embodiments, the enzyme is horseradish peroxidase.

According to still further features in the described preferred embodiments, the toxin is *Pseudomonas* exotoxin A or a portion thereof.

According to still further features in the described preferred embodiments, the portion of *Pseudomonas* exotoxin A is a translocation domain and/or an ADP ribosylation domain.

According to still further features in the described preferred embodiments, the human antigen-presenting molecule is a major histocompatibility complex molecule.

According to still further features in the described preferred embodiments, the major histocompatibility complex molecule is a major histocompatibility complex class I molecule.

According to still further features in the described preferred embodiments, the major-histocompatibility complex class I molecule is an HLA-A2 molecule.

According to still further features in the described preferred embodiments, the human antigen-presenting molecule is a single chain antigen-presenting molecule.

According to still further features in the described preferred embodiments, the pathogen is a viral pathogen.

According to still further features in the described preferred embodiments, the viral pathogen is a retrovirus.

According to still further features in the described preferred embodiments, the retrovirus is human T lymphotropic virus-1.

According to still further features in the described preferred embodiments, the antigen derived from a pathogen is restricted by the antigen-presenting molecule.

According to still further features in the described preferred embodiments, the antigen derived from a pathogen is a polypeptide.

According to still further features in the described preferred embodiments, the polypeptide is a segment of a Tax protein, or a polypeptide having an amino acid sequence as set forth in SEQ ID NO: 3.

The present invention successfully addresses the shortcomings of the presently known configurations by providing a composition-of-matter comprising an antibody or antibody fragment capable of binding with optimal specificity/affinity a human APM:pathogen-derived antigen complex.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a histogram depicting specific binding of recombinant Fab-phage clones to HLA-A2:$Tax_{11-19}$ complex, as determined by ELISA. TAX—HLA-A2:$Tax_{11-19}$ complex, gp100-154—HLA-A2:G9-154 peptide complex, MUC1-D6—HLA-A2:MUC1-D6 peptide complex, MART 27—HLA-A2:MART 27 peptide complex.

Figure 2A:
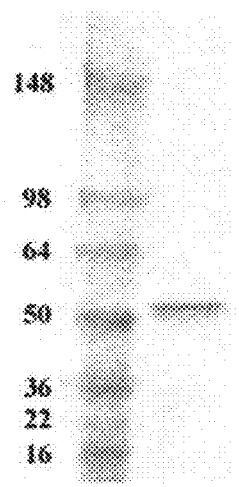
Figure 2B:
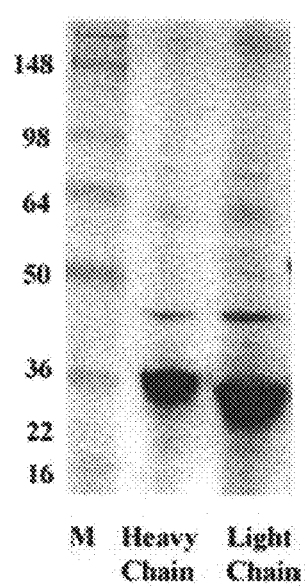
Figure 2C:
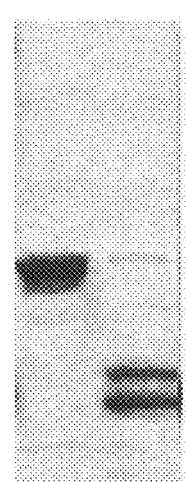

FIGS. 2a-c are photographs depicting Western immunoblotting assays of expression and purification of Fab's selected for specific binding to HLA-A2:$Tax_{11-19}$ complex. Shown are SDS-PAGE analyses of purified Fab protein after metal affinity chromatography, inclusion bodies from BL21 cultures expressing Fab T3F2 light chain and Fd fragment, and purified in vitro refolded non-reduced (NR) and reduced (R) Fab T3F2 (FIGS. 2a-c, respectively). M—molecular weight markers.

Figure 3A:
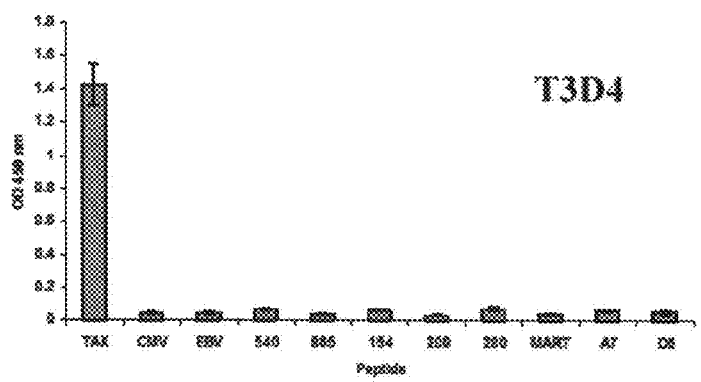
Figure 3B:
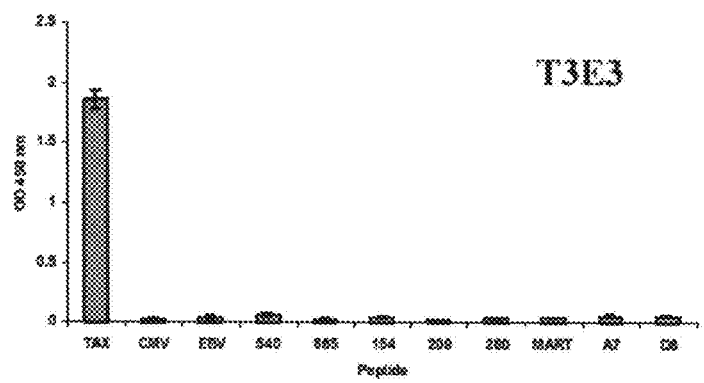
Figure 3C:
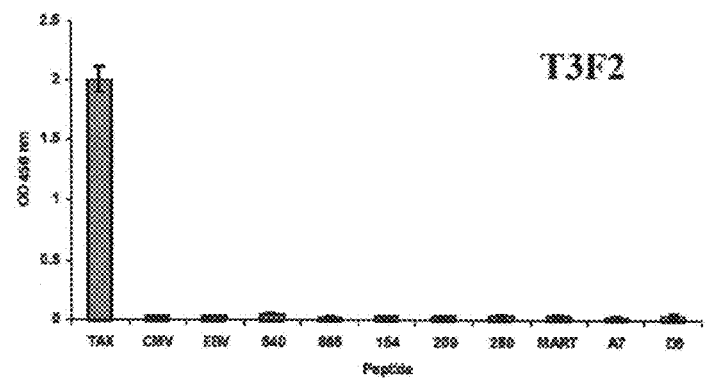

FIGS. 3a-c are histograms depicting specific binding of soluble purified Fab's T3D4, T3E3, and T3F2, respectively, to immobilized HLA-A2:$Tax_{11-19}$ complex, but not to HLA-A2:control peptide complexes, as determined by ELISA.

Figure 4A:
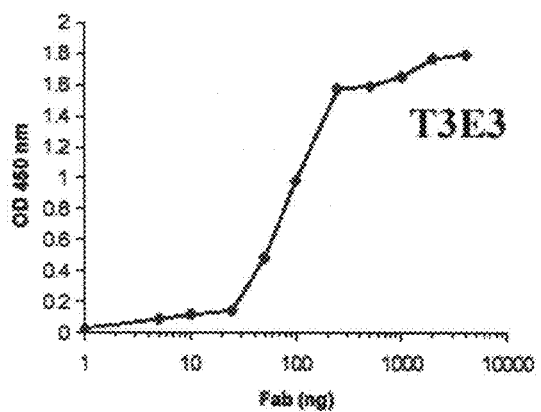
Figure 4B:
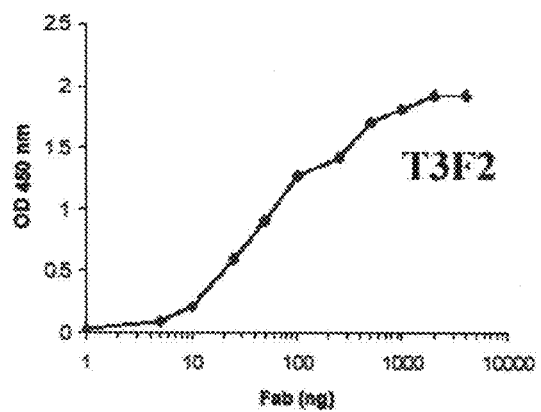

FIGS. 4a-b are data plots depicting the binding characteristics of Fab's T3E3 and T3F2, respectively, as determined by titration ELISA using single chain HLA-A2:$Tax_{11-19}$ complex as binding target.

Figure 4C:
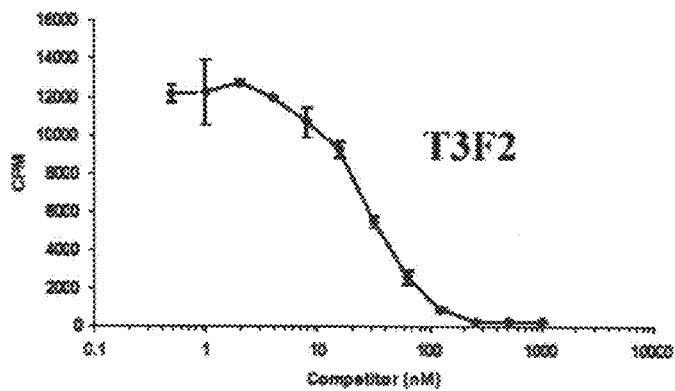

FIG. 4c is a competitive binding analysis data plot depicting the ability of purified Fab T3F2 to inhibit the binding of [125]iodine labeled Fab T3F2 to immobilized HLA-A2:Tax complex. The apparent binding affinity of the recombinant Fab was determined as the concentration of competitor (soluble purified Fab) required for 50 percent inhibition of the binding of the [125]iodine labeled tracer.

FIGS. 5a-f are flow cytometry histograms depicting specific detection of HLA-A2:$Tax_{11-19}$ complex on the surface of APCs. RMAS-HHD, JY, and human dendritic (DC) cells (FIGS. 5a-b, 5c-d, and 5e-f, respectively) were loaded with $Tax_{11-19}$ peptide or negative control melanoma gp100-derived peptide G9-154, as described in the experimental procedures. Peptide-loaded cells were then incubated with the soluble purified HLA-A2:Tax$_{11-19}$ complex specific Fab's T3E3 (FIGS. 5a, 5c, and 5e) or T3F2 (FIGS. 5b, 5d, and 5f). Note specific staining of cells loaded with Tax$_{11-19}$ but not negative control peptide. Control unloaded cells are shown in black trace. Control assays were performed using the 10 different negative control HLA-A2 restricted peptides listed under Materials and Methods.

Figure 6A:
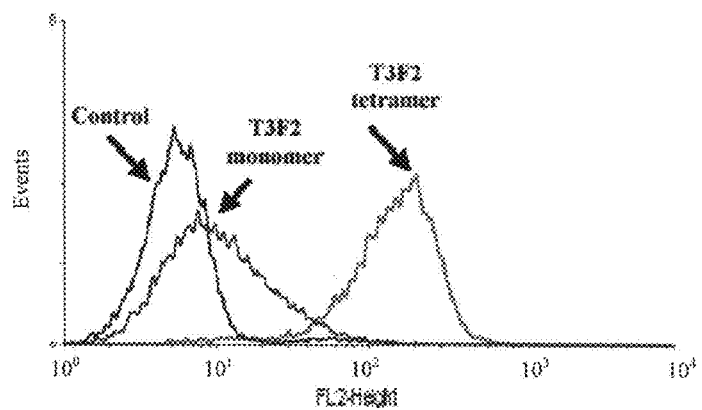
Figure 6B:
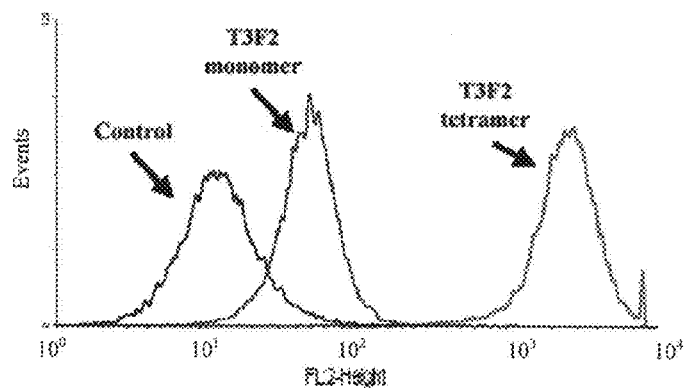
Figure 6C:
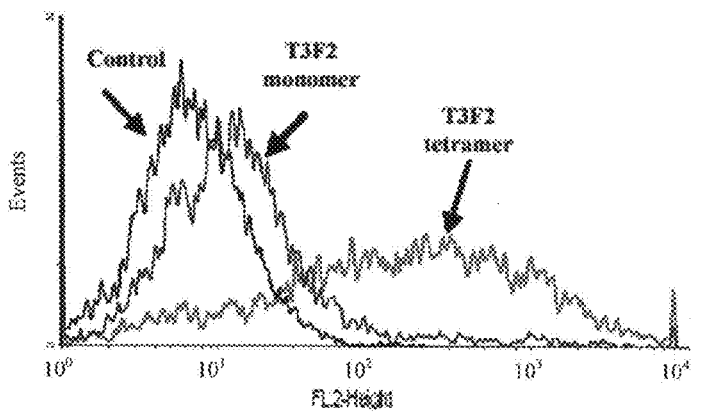

FIGS. 6a-c are flow cytometry histograms depicting specific detection of HLA-A2:Tax$_{11-19}$ complex on the surface of antigen-presenting cells (APCs) using Fab T3F2 tetramer. RMAS-HHD, JY, or HLA-A2 positive mature dendritic cells (FIGS. 6a-c, respectively) were pulsed with Tax$_{11-19}$ peptide. Peptide pulsed cells were then incubated with phycoerythrin conjugated T3F2 tetramer or monomer, as indicated. Fab monomer binding was detected using phycoerythrin conjugated anti human Fab antibody. Control unloaded cells stained with the T3F2 tetramer are shown.

Figure 7A:
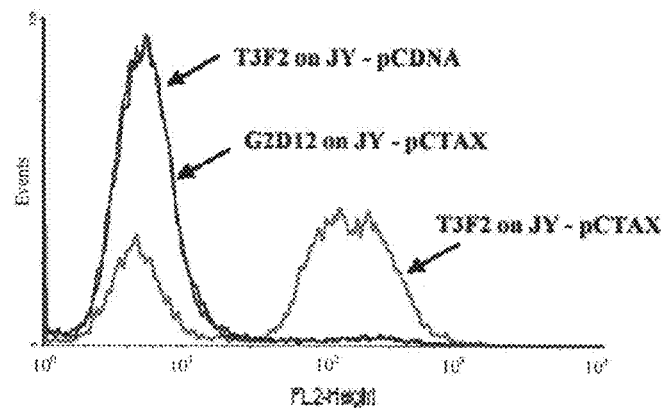
Figure 7B:
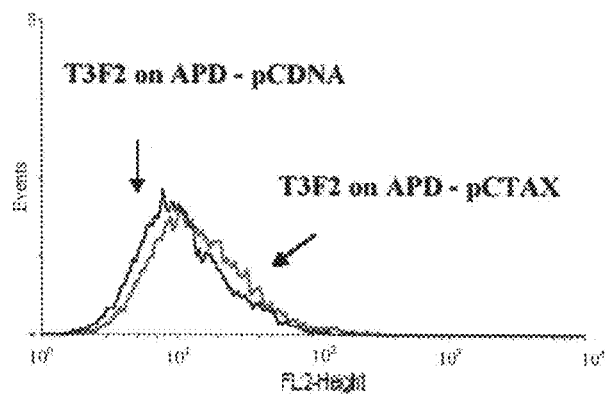
Figure 7C:
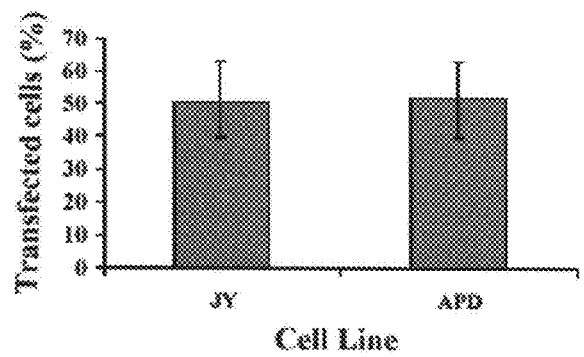
Figure 7D:
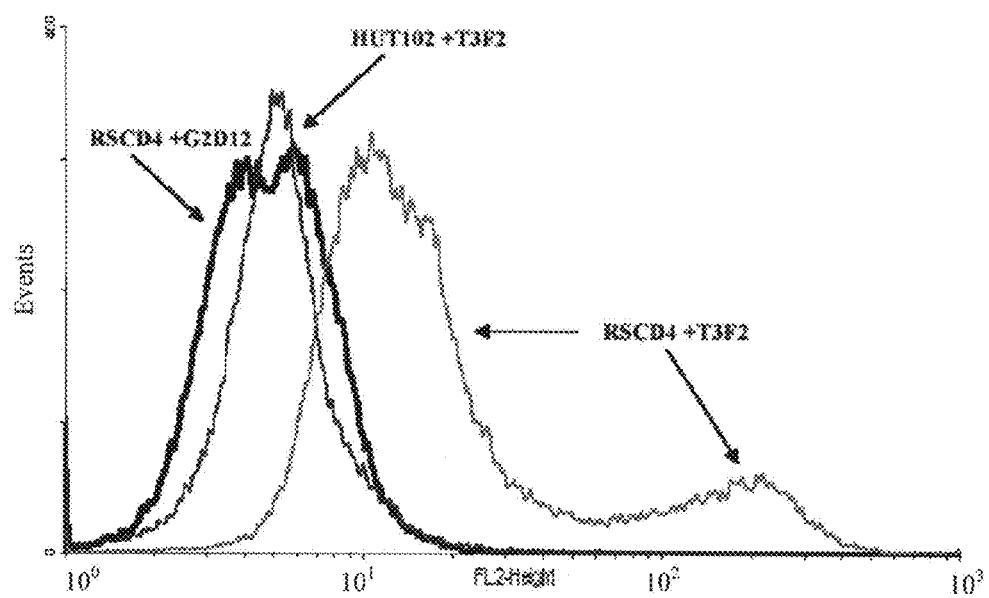

FIGS. 7a-d depict specific detection of cell surface displayed HLA-A2:Tax$_{11-19}$ complex by T3F2 after naturally occurring active intracellular processing. FIGS. 7a-b are flow cytometry histograms depicting specific detection of HLA-A2:Tax$_{11-19}$ complex on the surface of HLA-A2 positive JY cells, but not HLA-A2 negative APD cells, respectively. Cells were transfected with pcDNA control vector or with pcDNA containing the intact full length Tax gene (pcTAX), and 12 to 24 hours following transfection, cells were stained by flow cytometry using Fab T3F2 or the negative control Fab G2D12 specific for HLA-A2:G9-154 complex. FIG. 7c is a bar graph depicting the efficiency of Tax gene transduction into JY and APD cells, as monitored by transfection of the pcDNA vector carrying the GFP gene. FIG. 7d is a flow cytometry histogram depicting staining of HLA-A2 positive RSCD4 and HLA-A2 negative HUT102 cells (which are lines of human CD4 positive T-cells infected with HTLV-1) with phycoerythrin conjugated Fab T3F2 tetramer, or negative control G2D12, as indicated.

FIGS. 8a-b depict quantitation of the number of HLA-A2:Tax$_{11-19}$ complexes on the surface of Tax$_{11-19}$ peptide pulsed cells. JY APCs were pulsed with various concentrations of Tax$_{11-19}$ peptide and surface display of HLA-A2-Tax$_{11-19}$ peptide complex on the cells was analyzed by flow cytometry using phycoerythrin conjugated T3F2 Fab. FIG. 8a is a bar graph depicting the calculated number of complexes per cell with various concentration of peptide. The level of fluorescence intensity on stained cells was quantitated flow cytometrically using calibration beads conjugated to graded numbers of phycoerythrin molecules (QuantiBRITE PE beads, Becton-Dickinson). FIG. 8b is a flow cytometry histogram depicting fluorescence intensity as a function of Tax$_{11-19}$ peptide concentration.

FIGS. 8c-d depict high-sensitivity quantitative detection of HLA-A2:Tax$_{11-19}$ complex on the surface JY APCs transfected with the Tax gene mixed at different ratios within a non-transfected cell population. The mixed population was stained with Fab T3F2 and detection sensitivity was monitored by single-color flow cytometry. FIG. 8c is a set of overlapping flow cytometry histograms shown in large-scale (left panel) or zoomed (right panel) depicting quantitative detection of transfected cells mixed into populations of non-transfected cells at the various ratios, as indicated. FIG. 8d is a data table depicting sensitivity of detection of HLA-A2:Tax$_{11-19}$ complex as a function of the percentage of transfected cells admixed within a population of non-transfected cells, on the basis of a transfection efficiency of 62.1 percent. Note detection of HLA-A2:Tax$_{11-19}$ complex-displaying cells present in a population of non-transfected cells in a proportion as low as 1 percent.

Figure 9A:
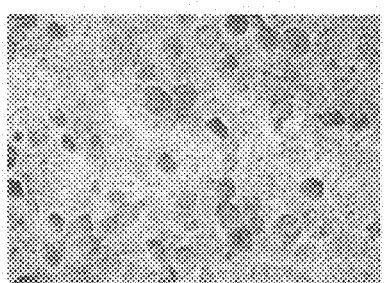
Figure 9B:
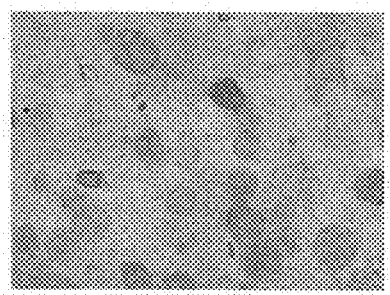
Figure 9C:
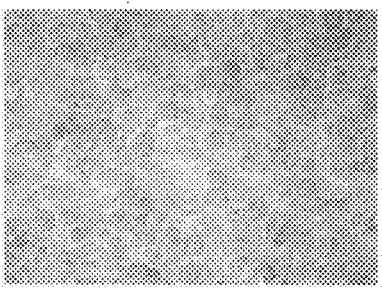
Figure 9D:
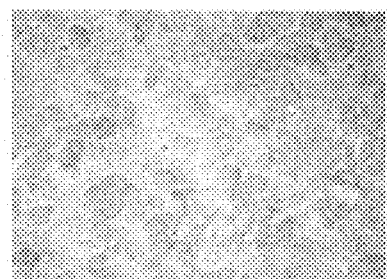
Figure 9E:
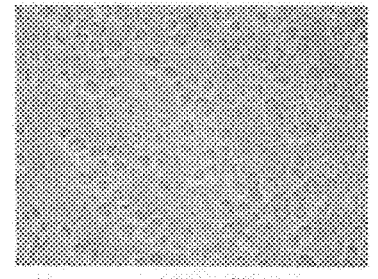
Figure 9F:
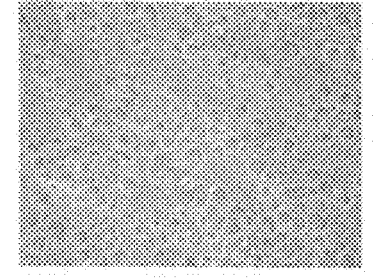

FIGS. 9a-f are photomicrographs depicting immunohistochemical detection of HLA-A2:Tax$_{11-19}$ complex by Fab T3F2 following intracellular processing. FIGS. 9a-b depict ×60 and ×40 original magnification views, respectively, of Tax transfected JY cells stained with Fab T3F2. FIG. 9c depicts control non transfected JY cells stained with Fab T3F2. FIG. 9d depicts staining of Tax transfected JY cells with negative control Fab G2D12 specific for HLA-A2:G9-154 complex. FIGS. 9e-f depict HLA-A2 negative cells transfected for expression of Tax or not transfected, respectively, stained with T3F2. Cells were adsorbed onto poly-L-lysine coated glass slips 12 to 24 hours following transfection, and stained with Fab T3F2. As a negative control Fab G2D12 was used.

Figure 10:
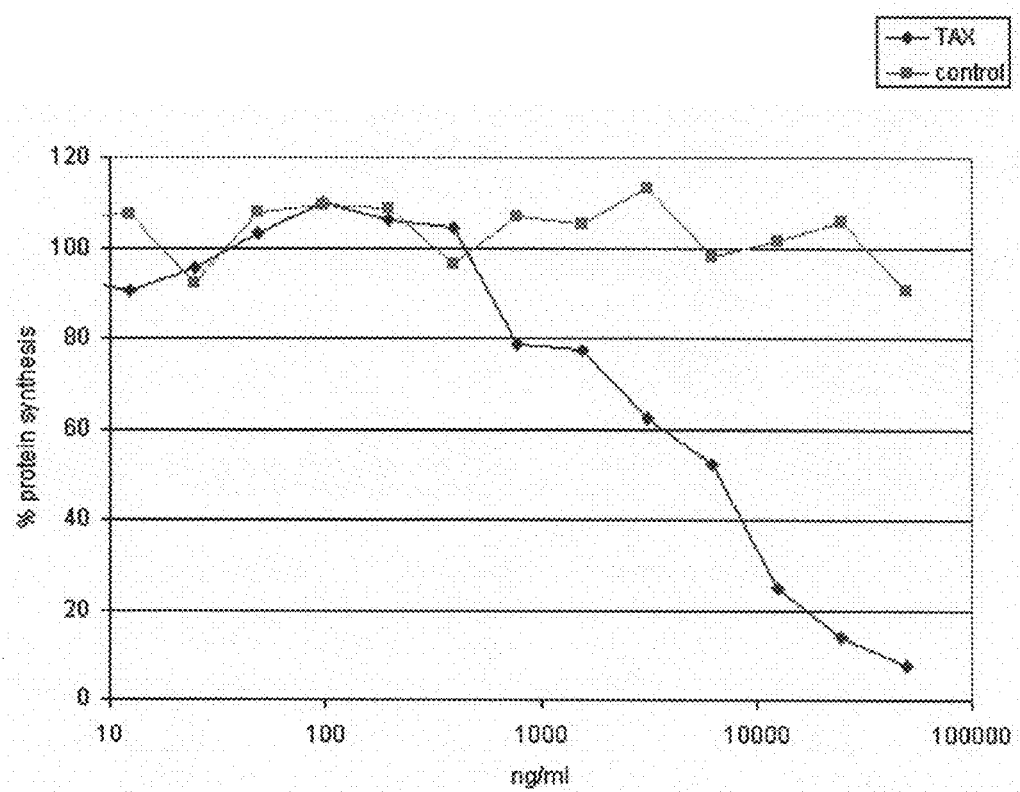

FIG. 10 is a data plot depicting specific and efficient killing of target cells displaying a specific human MHC:viral peptide complex by a fusion protein consisting of an anti specific human MHC:viral peptide complex Fab conjugated to a toxin. A cytotoxicity assay was performed using T3F2-PE38 KDEL fusion protein, consisting of anti HLA-A2:Tax$_{11-19}$ complex Fab fused to the PE38 KDEL truncated form of *pseudomonas* exotoxin A. To assay cytolysis by the fusion protein, JY cells loaded with Tax$_{11-19}$ peptide, loaded with control HLA-A2 restricted peptides, or not peptide loaded were incubated with T3F2-PE38 KDEL. Note specific and efficient T3F2-PE38 KDEL mediated killing of cells loaded with Tax$_{11-19}$ peptide, but not of control JY cells loaded control peptide, or of JY cells not peptide loaded.

DESCRIPTION OF THE PREFERRED EMBODIMENTS

The present invention is of compositions-of-matter capable of specifically binding particular antigen-presenting molecule (APM):antigen complexes, and to methods of using such compositions-of-matter to detect, characterize or kill/damage cells/tissues expressing/displaying such complexes. In particular, the present invention can be used to optimally detect, characterize or kill/damage human cells/tissues displaying/expressing a particular human APM:pathogen-derived antigen complex, such as cells/tissues infected with a pathogen, or antigen-presenting cells (APCs) exposed to the pathogen, or an antigen thereof. As such the compositions-of-matter of the present invention can be used, for example, to optimally diagnose, characterize, and treat a pathogen infection in a human.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Molecules capable of binding with optimal specificity/affinity a particular human APM:pathogen-derived antigen complex would be of significant and unique utility since they would enable optimal diagnosis, characterization, and treatment of pathogen infections in humans.

Various molecules capable of binding specific APM:antigen complexes have been described by the prior art.

For example, one approach involves using antibodies or derivatives thereof specific for mouse MHC:peptide complexes in attempts to provide compounds capable of specifically binding such murine complexes.

Another approach involves using antibodies or derivatives thereof specific for human MHC:tumor-associated antigen (TAA) peptide complexes in attempts to provide compounds capable of specifically binding such human tumor antigen-presenting complexes.

A further approach involves using antibodies or derivatives thereof specific for human MHC:telomerase-derived peptide complexes in attempts to provide compounds capable of specifically binding such human telomerase antigen-presenting complexes.

However, all such prior art approaches suffer from significant drawbacks. Prior art approaches involving molecules capable of specifically binding complexes comprising non-human APMs do not have utility for human applications, and prior art approaches involving compositions-of-matter capable of specifically binding complexes comprising non-pathogen-derived antigens do not have utility for applications requiring molecules capable of specifically binding complexes comprising pathogen-derived antigens, such as diagnosis, characterization, and treatment of pathogen infections in humans.

Thus, the prior art has failed to provide molecules capable of binding particular human APM:pathogen-derived antigen complexes with optimal specificity and affinity.

While reducing the present invention to practice molecules capable of binding particular human APM:pathogen-derived antigen complexes with optimal specificity and affinity were unexpectedly uncovered. Such a capacity is unique relative to all prior art molecules capable of binding particular APM:antigen complexes.

It was also unexpectedly uncovered that attaching such molecules to a detectable moiety or toxin could be used, respectively, to detect/characterize, or kill/damage with optimal efficiency/specificity cells/tissues displaying such complexes. Such capacities are also unique relative to all prior art molecules capable of binding particular APM:antigen complexes.

Thus, in sharp contrast to prior art molecules capable of binding particular APM:antigen complexes, the molecules of the present invention can be used to detect, or characterize with optimal specificity and sensitivity, or kill with optimal efficiency and specificity human cells/tissues infected with a pathogen, or antigen-presenting cells exposed to a pathogen, or an antigen thereof.

Thus, according to one aspect of the present invention there is provided a composition-of-matter comprising an antibody or antibody fragment including an antigen-binding region capable of specifically binding an antigen-presenting portion of a complex composed of an APM and an antigen derived from a pathogen.

The composition-of-matter is optimal for use in essentially any application benefiting from a reagent having the capacity to specifically bind the antigen-presenting portion of a complex composed of a particular APM and a particular antigen derived from a pathogen which is restricted by such an APM (referred to hereinafter as "complex" or "the complex"). Such applications particularly include those involving: (i) specific detection of the antigen-presenting portion of the complex, in particular for diagnosing a disease associated with the pathogen; (ii) killing/damaging cells/tissues displaying/expressing the antigen-presenting portion of the complex (referred to herein as "target cells/tissues"), including pathogen-infected cells or APCs exposed to an antigen of the pathogen; and (iii) blocking binding of the antigen-presenting portion of the complex to a cognate T-cell receptor (TCR); and (iv) isolating the complex or a cell displaying/expressing the complex.

As used herein, the term "antibody" refers to a substantially whole or intact antibody molecule.

As used herein, the phrase "antibody fragment" refers to molecule comprising a portion or portions of an antibody capable of specifically binding an antigenic determinant or epitope, such as the antigen-presenting portion of the complex.

As used herein, the phrase "antigen-binding region", when relating to the antibody or antibody fragment, refers to a portion of the antibody or antibody or antibody fragment (typically a variable portion) capable of specifically binding a particular antigenic determinant or epitope, or particular set of antigenic determinants or epitopes.

As used herein, the term "APM" refers to an antigen-presenting molecule such as an MHC molecule, a CD1 molecule, and a molecule structurally and/or functionally analogous to an MHC or CD1 molecule. A specific APM is typically capable of binding any of a particular set of distinct antigens so as to form an antigen-presenting complex therewith which can be specifically bound by a variable portion of a TCR. Antigen-presenting molecules forming complexes whose antigen-presenting portions comprise antigenic determinants or epitopes which can be specifically bound by the antibody or antibody fragment comprised in the composition-of-matter are described in further detail hereinbelow.

As used herein, the term "antigen" refers to a molecule or portion thereof (typically a peptide or a lipid), where such a molecule or portion thereof is capable of specifically binding an antigen-binding groove of an APM. Such an antigen is commonly referred to in the art as being "restricted" by such an APM. A typical antigen, such as a pathogen-derived antigen, is typically generated in a human cell by intracellular processing of a larger molecule derived from the pathogen. Such cells typically include a cell infected with the pathogen—in particular an intracellular pathogen, or an APC exposed to an antigen derived from the pathogen. The antigen generally has a characteristic dimension and/or chemical composition—for example, a characteristic amino acid length and set of anchor residues, respectively, in the case of a peptide antigen—enabling it to specifically bind the antigen-binding groove of a particular APM so as to form an APM:antigen complex therewith having an antigen presenting portion capable of specifically binding a variable region of a cognate TCR.

As used herein, the phrase "antigen-presenting portion", when relating to the complex, refers to any portion of the complex which can be specifically bound by the antibody or antibody fragment, such that the antibody or antibody fragment is effectively incapable of specifically binding: (i) the APM of the complex not bound to the antigen of the complex; (ii) an APM:antigen complex composed of the APM of the complex and an antigen other than that of the complex; or (iii) an APM:antigen complex composed of an APM other than that of the complex and any antigen restricted by such an APM, including the antigen of the complex.

As mentioned hereinabove, the antigen-presenting portion of the complex is typically a portion of the complex capable of specifically binding a cognate TCR variable region. Antigen-presenting portions of complexes which can be specifically bound by the antibody or antibody fragment comprised in the composition-of-matter of the present invention are described in further detail hereinbelow.

As used herein, the term peptide refers to a polypeptide composed of 50 amino acid residues or less.

Depending on the application and purpose, the composition-of-matter may comprise an antibody or an antibody fragment.

Preferably, the composition-of-matter comprises an antibody fragment.

Antibody fragments, various types of which are described in further detail hereinbelow, have the advantage of generally being smaller than an antibody while retaining essentially a substantially identical binding specificity of a whole antibody comprising the immunoglobulin variable regions of the antibody fragment. Thus, a composition-of-matter of the present invention comprising an antibody fragment will be generally smaller than one comprising an antibody, and will thereby generally have superior biodistribution, and diffusion properties (for example, systemically in-vivo, or in isolated tissues) than the latter. A smaller composition-of-matter will have the additional advantage of being less likely to include moieties capable of causing steric hindrance inhibiting binding of the antibody or antibody fragment comprised in the composition-of-matter to the antigen-presenting portion of the complex. Also, the absence of some or all of an antibody constant region (referred to herein as "constant region"), such as an Fc region, from a composition-of-matter of the present invention comprising an antibody fragment lacking such an Fc region will be advantageous for applications involving exposure of the composition-of-matter to a molecule capable of specifically binding such a constant region and in which such binding is undesirable. Typically this may involve an undesired binding of an Fc region comprised in a composition-of-matter of the present invention exposed to a cognate Fc receptor, or an Fc-binding complement component (for example, complement component C1q, present in serum). Fc receptors are displayed on the surface of numerous immune cell types, including: professional APCs, such as dendritic cells; B lymphocytes; and granulocytes such as neutrophils, basophils, eosinophils, monocytes, macrophages, and mast cells. In particular, the absence of a functional constant region, such as the Fc region, from the composition-of-matter will be particularly advantageous in applications in which the composition-of-matter is exposed to a specific ligand of a constant region, such as a cognate Fc receptor or an Fc binding complement component, capable of activating an undesired immune response, such as an Fc receptor-mediated immune cell activation or complement component-mediated complement cascade, respectively, via interaction with the constant region.

It will be appreciated by the ordinarily skilled artisan that in various contexts, the aforementioned Fc receptor-displaying cell types will function as APCs displaying/expressing the complex. Hence a composition-of-matter of the present invention comprising an antibody fragment lacking an Fc region may be advantageous for preventing undesired binding of the antibody or antibody fragment by Fc receptors displayed by such cells, or for preventing consequent activation of such cells.

Alternately, an antibody or antibody fragment of the present invention comprising such a functional constant region may be advantageous in applications in which such an immune response is desirable. This will be particularly desirable in applications involving use of the composition-of-matter to kill/damage target cells/tissues, as described in further detail hereinbelow. A composition-of-matter of the present invention comprising an antibody or an antibody fragment including a constant region, such as an Fc region, which may be conveniently attached to a functional moiety will also be advantageous for applications in which such attachment is desirable.

Furthermore, the use of a composition-of-matter of the present invention comprising an antibody fragment will be advantageous relative to one employing a whole antibody when employing recombinantly producing the antibody or antibody fragment due to antibody fragments being more economical and efficient to synthesize due to their smaller size relative to whole antibodies.

Depending on the application and purpose, the composition-of-matter may advantageously comprise an antibody or antibody fragment having any of various structural and/or functional characteristics. In particular, according to the teachings of the present invention, the composition-of-matter may advantageously comprise: (i) a monoclonal or polyclonal antibody or antibody fragment; (ii) a monomeric or multimeric form of antibody or antibody fragment; (iii) an antibody or antibody fragment of any of various configurations or types (such as those described hereinbelow); (iv) an antibody or antibody fragment, or portion thereof, originating from any of various mammalian species; (v) an antibody or antibody fragment attached to any of various functional moieties; (vi) an antibody or antibody fragment capable of specifically binding any of various particular complexes; and/or (vii) an antibody or antibody fragment capable of specifically binding the antigen-presenting portion of the complex with a desired affinity.

As mentioned hereinabove, depending on the application and purpose, the antibody or antibody fragment may be polyclonal or monoclonal.

As used herein, a composition-of-matter of the present invention comprising a "polyclonal" or "monoclonal" antibody or antibody fragment is a population of molecules of the composition-of-matter comprising a polyclonal or monoclonal population of the antibody or antibody fragment, respectively.

As used herein, a composition-of-matter of the present invention comprising a "polyclonal" or "monoclonal" antibody or antibody fragment is a population of composition-of-matter molecules of the present invention each comprising a monoclonal antibody or antibody fragment or a population thereof.

Methods of generating monoclonal or polyclonal antibodies or antibody fragments are described hereinbelow.

Preferably, according to the teachings of the present invention, the antibody or antibody fragment is monoclonal.

For applications benefiting from optimal reproducibility, standardization, or precision, such as analytical applications, as described in further detail hereinbelow, a composition-of-matter comprising a monoclonal antibody or antibody fragment will generally be superior to one comprising a polyclonal antibody or antibody fragment directed at the antigen-presenting portion of the same complex. A monoclonal antibody or antibody fragment will be particularly advantageous in instances where the antibody or antibody fragment has been characterized as having a desired binding affinity/specificity for the antigen-presenting portion of the complex. A composition-of-matter of the present invention comprising such an antibody or antibody fragment will thus be optimal for an application, as will generally be the case, benefiting from a composition-of-matter comprising an antibody or antibody fragment capable of binding the antigen-presenting portion of the complex with the highest affinity/specificity possible.

As is described and demonstrated in the Examples section below, a composition-of-matter comprising a monoclonal antibody fragment can be used to optimally practice various aspects of the present invention, including applications involving specific detection of the complex, or killing/damaging of target cells/tissues.

Alternately, for applications wherein a composition-of-matter capable of binding one or more complexes with a spectrum of, or with various distinct affinities/specificities is desirable, a composition-of-matter of the present invention comprising a polyclonal antibody or antibody fragment will be advantageous. In any case, where no monoclonal antibody or antibody fragment having a desired binding affinity/specificity for the antigen-presenting portion of the complex is available, a composition-of-matter comprising a polyclonal antibody or antibody fragment will nevertheless often be adequate since the heterogeneity of a polyclonal antibody or antibody fragment mixture will often include one or more antibodies or antibody fragments having an adequate binding affinity/specificity for the antigen-presenting portion of the complex.

As mentioned hereinabove, depending on the application and purpose, the antibody fragment may be any of various configurations or types.

Suitable antibody fragments include a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, an Fv, a single chain Fv, an Fab, an Fab', and an F(ab')$_2$.

Antibody fragments among the aforementioned antibody fragments which comprise whole or essentially whole variable regions of both light and heavy chains are defined as follows: (i) Fv, a fragment of an antibody molecule consisting of the light chain variable domain ($V_L$) and the heavy chain variable domain ($V_H$) expressed as two chains (typically obtained via genetic engineering of immunoglobulin genes); (ii) single chain Fv (also referred to in the art as "scFv"), a single chain molecule including the variable region of the light chain and the variable region of the heavy chain, linked by a suitable polypeptide linker (a single-chain Fv is typically obtained via genetic engineering of immunoglobulin genes and polypeptide linker-encoding DNA); (iii) Fab, a fragment of an antibody molecule containing essentially a monovalent antigen-binding portion of an antibody generally obtained by suitably treating the antibody with the enzyme papain to yield the intact light chain and the heavy chain Fd fragment (the Fd fragment consists of the variable and $C_H1$ domains of the heavy chain); (iv) Fab', a fragment of an antibody molecule containing a monovalent antigen binding portion of an antibody typically obtained by suitably treating the antibody molecule with the enzyme pepsin, followed by reduction of the resultant F(ab')$_2$ fragment (two Fab' fragments are obtained per antibody molecule); and (v) F(ab')$_2$, a fragment of an antibody molecule containing a monovalent antigen-binding portion of an antibody molecule typically obtained by suitably treating the antibody molecule with the enzyme pepsin (i.e., an F(ab')$_2$ consists of two Fab's connected by a pair of disulfide bonds).

Depending on the application and purpose, the antibody fragment is preferably an Fab, or a single chain Fv.

As is described and illustrated in the Examples section which follows, and as described in further detail below, a composition-of-matter of the present invention comprising an Fab may be employed to effectively practice the present invention, in particular aspects thereof involving using the composition-of-matter to detect the antigen-presenting portion of the complex.

As is described and illustrated in the Examples section which follows, and as described in further detail below, a composition-of-matter of the present invention comprising a single chain Fv may be utilized to effectively practice the present invention, in particular aspects thereof involving utilizing the composition-of-matter to kill/damage target cells/tissues.

It will be appreciated by the ordinarily skilled artisan that, due to an Fab' being essentially similar in structure to an Fab, a composition-of-matter of the present invention comprising an Fab' may be employed interchangeably with one comprising an Fab, where such Fab' and Fab comprise essentially the same heavy and light chain variable regions. For applications, as will usually be the case, benefiting from a composition-of-matter of the present invention comprising an antibody fragment capable of binding the antigen-presenting portion of the complex with the highest possible affinity, a composition-of-matter of the present invention comprising an F(ab')$_2$ may be advantageously employed over one comprising a monovalent antibody fragment, such as an Fab, an Fab' or a single chain Fv, due to the divalent binding of an F(ab')$_2$ to the antigen-presenting portion of the complex relative to the monovalent binding of such a monovalent antibody fragment.

As mentioned hereinabove, depending on the application and purpose, the antibody or antibody fragment may originate from any of various mammalian species.

Preferably, the antibody or antibody fragment is of human origin.

An antibody or antibody fragment of human origin may be derived as described further hereinbelow, or as described in the Examples section which follows.

A composition-of-matter of the present invention comprising an antibody or antibody fragment of human origin will generally be preferable for applications involving administration of the composition-of-matter to an individual. For example, such an antibody or antibody fragment will generally tend to be better tolerated immunologically than one of non human origin since non variable portions of non human antibodies will tend to trigger xenogeneic immune responses more potent than the allogeneic immune responses triggered by human antibodies which will typically be allogeneic with the individual. It will be preferable to minimize such immune responses since these will tend to shorten the half-life, and hence the effectiveness, of the composition-of-matter in the individual. Furthermore, such immune responses may be pathogenic to the individual, for example by triggering harmful inflammatory reactions.

As used herein, the term "individual", refers to a human.

Alternately, an antibody or antibody fragment of human origin, or a humanized antibody, will also be advantageous for applications in which a functional physiological effect, for example an immune response against a target cell, activated by a constant region of the antibody or antibody fragment in the individual is desired. Such applications particularly include those in which the functional interaction between a functional portion of the antibody or antibody fragment, such as an Fc region, with a molecule such as an Fc receptor or an Fc-binding complement component, is optimal when such a functional portion is, similarly to the Fc region, of human origin.

Depending on the application and purpose, a composition-of-matter of the present invention comprising an antibody or antibody fragment including a constant region, or a portion thereof, of any of various isotypes may be employed. Preferably, the isotype is selected so as to enable or inhibit a desired physiological effect, or to inhibit an undesired specific binding of the composition-of-matter via the constant region or portion thereof. For example, for inducing antibody-dependent cell mediated cytotoxicity (ADCC) by a natural killer (NK) cell, the isotype will preferably be IgG; for inducing ADCC by a mast cell/basophil, the isotype will preferably be IgE; and for inducing ADCC by an eosinophil, the isotype will preferably be IgE or IgA. For inducing a complement cascade the composition-of-matter will preferably comprise an antibody or antibody fragment comprising a constant region or portion thereof capable of initiating the cascade. For example, the antibody or antibody fragment may advantageously comprise a Cgamma2 domain of IgG or Cmu3 domain of IgM to trigger a C1q-mediated complement cascade.

Conversely, for avoiding an immune response, such as the aforementioned one, or for avoiding a specific binding via the constant region or portion thereof, the composition-of-matter will preferably not comprise a constant region, or a portion thereof, of the relevant isotype.

As mentioned hereinabove, depending on the application and purpose, the antibody or antibody fragment may be attached to any of various functional moieties. An antibody or antibody fragment, such as that of the present invention, attached to a functional moiety may be referred to in the art as an "immunoconjugate".

Preferably, the functional moiety is a detectable moiety or a toxin. An antibody or antibody fragment attached to a toxin may be referred to in the art as an immunotoxin.

As is described and demonstrated in further detail hereinbelow, a detectable moiety or a toxin may be particularly advantageously employed in applications of the present invention involving use of the composition-of-matter to detect the antigen-presenting portion of the complex, or to kill/damage target cells/tissues, respectively.

The composition-of-matter may comprise an antibody or antibody fragment attached to any of numerous types of detectable moieties, depending on the application and purpose.

For applications involving using the composition-of-matter to detect the antigen-presenting portion of the complex, the detectable moiety attached to the antibody or antibody fragment is preferably a reporter moiety enabling specific detection of the antigen-presenting portion of the complex bound by the antibody or antibody fragment of the composition-of-matter.

While various types of reporter moieties may be utilized to detect the antigen-presenting portion of the complex, depending on the application and purpose, the reporter moiety is preferably a fluorophore or an enzyme. Alternately, the reporter moiety may be a radioisotope, such as [125]iodine, as is described and illustrated in the Examples section below.

A fluorophore may be advantageously employed as a detection moiety enabling detection of the antigen-presenting portion of the complex via any of numerous fluorescence detection methods. Depending on the application and purpose, such fluorescence detection methods include, but are not limited to, fluorescence activated flow cytometry (FACS), immunofluorescence confocal microscopy, fluorescence in-situ hybridization (FISH), fluorescence resonance energy transfer (FRET), and the like.

Various types of fluorophores, depending on the application and purpose, may be employed to detect the antigen-presenting portion of the complex.

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like.

Preferably, the fluorophore is phycoerythrin.

As is described and illustrated in the Examples section below, a composition-of-matter of the present invention comprising an antibody or antibody fragment attached to a fluorophore, such as phycoerythrin, can be used to optimally detect the antigen-presenting portion of the complex using various immunofluorescence-based detection methods.

Ample guidance regarding fluorophore selection, methods of linking fluorophores to various types of molecules, such as an antibody or antibody fragment of the present invention, and methods of using such conjugates to detect molecules which are capable of being specifically bound by antibodies or antibody fragments comprised in such immunoconjugates is available in the literature of the art [for example, refer to: Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. While various methodologies may be employed to detect the antigen-presenting portion of the complex using a fluorophore, such detection is preferably effected as described and demonstrated in the Examples section below.

Alternately, an enzyme may be advantageously utilized as the detectable moiety to enable detection of the antigen-presenting portion of the complex via any of various enzyme-based detection methods. Examples of such methods include, but are not limited to, enzyme linked immunosorbent assay (ELISA; for example, to detect the antigen-presenting portion of the complex in a solution), enzyme-linked chemiluminescence assay (for example, to detect the complex in an electrophoretically separated protein mixture), and enzyme-linked immunohistochemical assay (for example, to detect the complex in a fixed tissue).

Numerous types of enzymes may be employed to detect the antigen-presenting portion of the complex, depending on the application and purpose.

Examples of suitable enzymes include, but are not limited to, horseradish peroxidase (HPR), beta-galactosidase, and alkaline phosphatase (AP).

Preferably, the enzyme is horseradish peroxidase.

As is described in the Examples section which follows, a composition-of-matter of the present invention comprising an antibody or antibody fragment attached to an enzyme such as horseradish peroxidase can be used to effectively detect the antigen-presenting portion of the complex, such as via ELISA, or enzyme-linked immunohistochemical assay.

Ample guidance for practicing such enzyme-based detection methods is provided in the literature of the art (for example, refer to: Khatkhatay M I. and Desai M., 1999. J Immunoassay 20:151-83; Wisdom G B., 1994. Methods Mol. Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49). While various methodologies may be employed to detect the antigen-presenting portion of the complex using an enzyme, such detection is preferably effected as described in the Examples section below.

The functional moiety may be attached to the antibody or antibody fragment in various ways, depending on the context, application and purpose.

A polypeptidic functional moiety, in particular a polypeptidic toxin, may be advantageously attached to the antibody or antibody fragment via standard recombinant techniques broadly practiced in the art (for Example, refer to Sambrook et al., infra, and associated references, listed in the Examples section which follows). While various methodologies may be employed, attaching a polypeptidic functional moiety to the antibody or antibody fragment is preferably effected as described and illustrated in the Examples section below.

A functional moiety may also be attached to the antibody or antibody fragment using standard chemical synthesis techniques widely practiced in the art [for example, refer to the extensive guidelines provided by The American Chemical Society (for example at: http://www.chemistry.org/portal/Chemistry)]. One of ordinary skill in the art, such as a chemist, will possess the required expertise for suitably practicing such chemical synthesis techniques.

Alternatively, a functional moiety may be attached to the antibody or antibody fragment by attaching an affinity tag-coupled antibody or antibody fragment of the present invention to the functional moiety conjugated to a specific ligand of the affinity tag.

Various types of affinity tags may be employed to attach the antibody or antibody fragment to the functional moiety.

Preferably, the affinity tag is a biotin molecule, more preferably a streptavidin molecule.

A biotin or streptavidin affinity tag can be used to optimally enable attachment of a streptavidin-conjugated or a biotin-conjugated functional moiety, respectively, to the antibody or antibody fragment due to the capability of streptavidin and biotin to bind to each other with the highest non covalent binding affinity known to man (i.e., with a Kd of about $10^{-14}$ to $10^{-15}$). A biotin affinity tag may be highly advantageous for applications benefiting from, as will oftentimes be the case, a composition-of-matter of the present invention comprising a multimeric form of the antibody or antibody fragment, which may be optimally formed by conjugating multiple biotin-attached antibodies or antibody fragments of the present invention to a streptavidin molecule, as described in further detail below.

As used herein the term "about" refers to plus or minus 10 percent.

Various methods, widely practiced in the art, may be employed to attach a streptavidin or biotin molecule to a molecule such as the antibody or antibody fragment to a functional moiety.

For example, a biotin molecule may be advantageously attached to an antibody or antibody fragment of the present invention attached to a recognition sequence of a biotin protein ligase. Such a recognition sequence is a specific polypeptide sequence serving as a specific biotinylation substrate for the biotin protein ligase enzyme. Ample guidance for biotinylating a target polypeptide such as an antibody fragment using a recognition sequence of a biotin protein ligase, such as the recognition sequence of the biotin protein ligase BirA, is provided in the literature of the art (for example, refer to: Denkberg, G. et al., 2000. Eur. J. Immunol. 30:3522-3532). Preferably, such biotinylation of the antibody or antibody fragment is effected as described and illustrated in the Examples section below.

Alternately, various widely practiced methods may be employed to attach a streptavidin molecule to an antibody fragment, such as a single chain Fv (for example refer to Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson). Standard recombinant DNA chemical techniques are preferably employed to produce a fusion protein comprising streptavidin fused to a polypeptidic functional moiety. Standard chemical synthesis techniques may also be employed to form the streptavidin-functional moiety conjugate. Extensive literature is available providing guidance for the expression, purification and uses of streptavidin or streptavidin-derived molecules (Wu S C. et al., 2002. Protein Expression and Purification 24:348-356; Gallizia A. et al., 1998. Protein Expression and Purification 14:192-196), fusion proteins comprising streptavidin or streptavidin-derived molecules (Sano T. and Cantor C R., 2000. Methods Enzymol. 326:305-11), and modified streptavidin or streptavidin-derived molecules (see, for example: Sano T. et al., 1993. Journal of Biological Chemistry 270:28204-28209), including for streptavidin or streptavidin-derived molecules whose gene sequence has been optimized for expression in $E.\ coli$ (Thompson L D. and Weber P C., 1993. Gene 136:243-6).

The use of a composition-of-matter of the present invention comprising an antibody or antibody fragment attached to a functional moiety for various purposes other than detection of the antigen-presenting portion of the complex, or killing/damaging target cells/tissues is also envisaged by the present invention. In particular, a composition-of-matter of the present invention comprising an antibody or antibody fragment attached to an affinity tag, or any substance, particle, virus or cell displaying/expressing such a composition-of-matter, can be conveniently isolated or purified using an affinity purification method employing as a capture ligand a specific ligand of the affinity tag. Preferably, for such purposes, the affinity tag is a polyhistidine tag, and the purification method is effected using nickel as the specific ligand of the affinity tag.

A histidine tag is a peptide typically consisting of 4 to 8 histidine amino acid residues. Preferably a histidine tag composed of 6 histidine residues, commonly referred to as a hexahistidine tag in the art, is employed. Such histidine tags specifically bind nickel-containing substrates. Ample guidance regarding the use of histidine tags is available in the literature of the art (for example, refer to Sheibani N., 1999. Prep Biochem Biotechnol. 29:77). Purification of molecules comprising histidine tags is routinely effected using nickel-based affinity purification techniques. An alternate suitable capture ligand for histidine tags is the anti histidine tag single-chain antibody 3D5 (Kaufmann, M. et al., 2002. J Mol. Biol. 318, 135-47). While various techniques may be employed, purifying a composition-of-matter of the present invention comprising an antibody or antibody fragment attached to a histidine tag is preferably effected as described and illustrated in the Examples section which follows.

The composition-of-matter may be purified using any of various suitable standard and widely employed affinity chromatography techniques. Ample guidance for practicing such techniques is provided in the literature of the art [for example, refer to: Wilchek M. and Chaiken I., 2000. Methods Mol Biol 147, 1-6; Jack G W., 1994. Mol Biotechnol 1, 59-86; Narayanan S R., 1994. Journal of Chromatography A 658, 237-258; Nisnevitch M. and Firer M A., 2001. J Biochem Biophys Methods 49, 467-80; Janson J C. and Kristiansen T. in "Packings and Stationary Phases in Chromatography Techniques", Unger K K. (ed), Marcel Dekker, New York, pp. 747 (1990); Clonis Y D: HPLC of Macromolecules: A Practical Approach, IRL Press, Oxford, pp. 157 (1989); Nilsson J. et al., 1997. Protein Expr Purif. 11:1-16].

Various affinity tags, other than those described hereinabove, may also be employed to attach the functional moiety to the antibody or antibody fragment or to purify a composition-of-matter of the present invention comprising an antibody or antibody fragment attached to an affinity tag, or any substance, particle, virus or cell displaying/expressing such a composition-of-matter.

Such affinity tags include, but are not limited to, a streptavidin tag (Strep-tag), an epitope tag (a moiety, usually peptidic, which can be specifically bound with high affinity by a specific monoclonal antibody), a maltose-binding protein (MBP) tag, and a chitin-binding domain (CBD) tag.

Examples of epitope tags include an 11-mer Herpes simplex virus glycoprotein D peptide, and an 11-mer N-terminal bacteriophage t7 peptide, being commercially known as HSVTag and t7Tag, respectively (Novagen, Madison, Wis., USA), and 10- or 9-amino acid c-myc or *Haemophilus influenza* hemagglutinin (HA) peptides, which are recognized by the variable regions of monoclonal antibodies 9E10 and 12Ca5, respectively.

A Strep-tag is a peptide having the capacity to specifically bind streptavidin. Ample guidance regarding the use of Strep-tags is provided in the literature of the art (see, for example: Schmidt, T G M. and Skerra, A. 1993. Protein Eng. 6:109; Schmidt T G M. et al., 1996. Journal of Molecular Biology 255:753-766; Skerra A. and Schmidt T G M., 1999. Biomolecular Engineering 16:79-86; Sano T. and Cantor C R. 2000. Methods Enzymol. 326, 305-11; and Sano T. et al., 1998. Journal of Chromatography B 715:85-91).

A suitable maltose-binding domain tag is malE-encoded maltose-binding protein which has the capacity to specifically bind a substrate including amylose such as, for example, an amylose-based affinity purification column. Ample guidance regarding the use of maltose-binding protein as an affinity tag is provided in the literature of the art (see, for example: Guan M. et al., 2002. Protein Expr Purif. 26:229-34; Cattoli F and Sarti G C, 2002. Biotechnol Prog. 18:94-100).

A suitable chitin-binding domain tag is *B. circulans* cbd-encoded chitin binding domain which has the capacity to specifically bind chitin. Ample guidance regarding the use of maltose-binding protein as an affinity tag is provided in the literature of the art (see, for example: Humphries H E et al., 2002. Protein Expr Purif. 26:243-8; and Chong S. et al., 1997. Gene 192:271-81).

Thus, the functional moiety may be attached to the antibody or antibody fragment via any of the aforementioned various affinity tags, depending on the application and purpose.

As mentioned hereinabove, the functional moiety attached to the antibody or antibody fragment may be a toxin.

For applications of the composition-of-matter involving killing/damaging of target cells/tissues, the toxin is preferably capable of killing/damaging the target cells/tissues when conjugated thereto as a consequence of specific binding of the antibody or antibody fragment to the antigen-presenting portion of the complex.

Any of various toxins may be attached to the antibody or antibody fragment, to thereby generate an immunotoxin suitable, for example, to kill/damage target cells/tissues using a composition-of-matter comprising such an immunotoxin.

Preferably, the toxin is *Pseudomonas* exotoxin A, more preferably a portion thereof comprising the translocation domain and/or an ADP ribosylation domain. Preferably, the portion comprising the translocation domain and/or an ADP ribosylation domain is the toxin PE38KDEL. Generation of an immunotoxin comprising PE38KDEL as a toxin moiety is preferably effected as described and illustrated in the Examples section below. Ample guidance for generating such an immunotoxin is provided in the literature of the art (for example, refer to: Brinkmann U. et al., 1991. Proc. Natl. Acad. Sci. U.S.A. 88:8616-20; and Brinkmann U., 2000. In-vivo 14:21-7).

Other types of toxins which may be attached to the antibody or antibody fragment, depending on the application and purpose, in particular to kill/damage a target cell, include, but are not limited to, various bacterial toxins, plant toxins, chemotherapeutic agents, and radioisotopes, respectively. Examples of toxins commonly used to generate immunotoxins include ricin and *Pseudomonas* exotoxin A-derived PE40 toxin. Alternately, immunotoxins may be generated with toxins such as diphtheria toxin, *pertussis* toxin, or *cholera* toxin.

Ample guidance for selecting, generating and using immunotoxins is provided in the literature of the art (for example, refer to: Knechtle S J. 2001, Philos Trans R Soc Lond B Biol: Sci. 356:681-9; Hall W A., 2001. Methods Mol. Biol. 166: 139-54; Brinkmann U., 2000. In-vivo 14:21-7; Haggerty H G. et al., 1999. Toxicol Pathol. 27:87-94; Chaplin J W., 1999. Med Hypotheses 52:133-46; Wu M., 1997. Br J Cancer. 75:1347-55; Hall W A. 1996, Neurosurg Clin N Am. 7:537-46; Pasqualucci L. et al., 1995. Haematologica 80:546-56; Siegall C B., 1995. Semin Cancer Biol. 6:289-95; Grossbard M L. et al., Clin Immunol Immunopathol. 76:107-14; Ghetie M A and Vitetta E S., 1994. Curr Opin Immunol. 6:707-14; Grossbard M L and Nadler L M., 1994. Semin Hematol. 31:88-97; Frankel A E., 1993. Oncology (Huntingt) 7:69-78; Pai L H. and Pastan I., 1993. JAMA. 269:78-81; Boon, T. and van der Bruggen, P., 1996. J. Exp. Med. 183:725-729; Renkvist, N. et al., 2001. Cancer Immunol Immunother. 50:3-15; Rosenberg, S. A., 2001. Nature 411:380-384; and U.S. Pat. No. 5,677,274).

As mentioned hereinabove, depending on the application and purpose, the composition-of-matter may advantageously comprise a monomeric or multimeric form of the antibody or antibody fragment.

A composition-of-matter of the present invention comprising a multimeric form of the antibody or antibody fragment will generally bind the antigen-presenting portion of the complex with higher avidity, and thereby with higher affinity, than one comprising a monomeric form of the antibody or antibody fragment. Hence, a composition-of-matter of the present invention comprising a multimeric form of the antibody or antibody fragment may be advantageous for applications benefiting from, as will usually be the case, a reagent capable of specifically binding the antigen-presenting portion of the complex with the highest affinity possible.

As is described and illustrated in the Examples section below, a composition-of-matter of the present invention comprising a multimeric form of an antibody or antibody fragment may be advantageously employed to effectively practice the method of the present invention, in particular with respect to applications involving using the composition-of-matter to specifically detect the antigen-presenting portion of the complex.

Various methods may be employed to generate a composition-of-matter of the present invention comprising a multimeric form of the antibody or antibody fragment.

Preferably, the multimeric form of the antibody or antibody fragment is generated by binding a plurality of antibodies or antibody fragments attached to an affinity tag to a multimerizing molecule capable of specifically and simultaneously binding such a plurality of affinity tags. Alternately, the multimeric form of the antibody or antibody fragment may be generated by attaching a plurality of antibodies or antibody fragments of the present invention to a moiety capable of automultimerizing, so as to thereby multimerize such a plurality of antibodies or antibody fragments.

Any of various types of multimerizing molecule/affinity tag combinations may be employed to generate the multimeric form of the antibody or antibody fragment of the present invention.

Preferably, such a combination consists of a biotin affinity tag, and a streptavidin multimerizing molecule, which, as described hereinabove, bind to each other with the highest affinity known to man, and hence will normally generate an optimally stable multimeric form of an antibody or antibody fragment of the present invention.

For certain applications a composition-of-matter of the present invention comprising a monomeric form of the antibody or antibody fragment may be advantageous. Such a composition-of-matter, due to its relatively small size may be advantageous for applications, such as in-vivo applications, benefiting from optimal biodistribution and/or diffusion thereof.

As is described and illustrated in the Examples section which follows, a composition-of-matter of the present invention comprising a monomeric form of an antibody or antibody fragment of the present invention may be advantageously utilized, for example, in applications where such an antibody or antibody fragment is attached to a toxin to kill/damage target cells.

Preferably, the composition-of-matter comprises an antibody or antibody fragment capable of specifically binding a complex in which the APM is an MHC class I molecule and the antigen is an MHC class I-restricted antigen (referred to herein as "MHC class I:antigen complex").

Alternately, the composition-of-matter may comprise an antibody or antibody fragment capable of specifically binding the antigen-presenting portion of a complex in which the APM is an MHC class II molecule and the antigen is an MHC class II-restricted antigen ("MHC class II:antigen complex"), or the APM is a CD1 molecule and the antigen is a CD1-restricted antigen ("CD1: antigen complex"). The composition-of-matter may also comprise an antibody or antibody fragment capable of specifically binding a complex structurally and/or functionally analogous to an APM:antigen complex such as one of the aforementioned MHC- or CD1-based complexes.

The composition-of-matter may comprise an antibody or antibody fragment capable of specifically binding the antigen-presenting portion of any of various particular MHC class II:antigen complexes. For example, the antigen-presenting portion of an MHC class II:antigen complex having as an APM an HLA-DP, HLA-DQ or HLA-DR molecule.

A composition-of-matter of the present invention may comprise an antibody or antibody fragment capable of specifically binding the antigen-presenting portion of a complex composed of an MHC class II molecule and any of various MHC class II-restricted antigens, which are generally peptides about 10 to 30 amino acid residues in length. Such peptides generally have particular chemical compositions enabling their specific binding to a particular MHC class II molecule (for example, refer to: Fairchild P J., 1998. J Pept Sci. 4:182; Rammensee H G., 1995. Curr Opin Immunol. 7:85; Sinigaglia F. and Hammer J., 1994. APMIS. 102:241; and Hobohm U. and Meyerhans A., 1993. Eur J. Immunol. 23:1271).

The composition-of-matter may comprise an antibody or antibody fragment capable of specifically binding the antigen-presenting portion of any of various particular CD1:antigen complexes. For example, the antigen-presenting portion of a CD1:antigen complex having as an APM a CD1a, CD1b, CD1c or CD1d molecule.

A composition-of-matter of the present invention may comprise an antibody or antibody-fragment capable of specifically binding the antigen-presenting portion of a complex composed of a CD1 molecule and any of various CD1-restricted antigens, which may be either peptides or more typically lipids. For example: CD1b and CD1c molecules both have the capacity to specifically associate with CD1b- or CD1-c-restricted lipoarabinomannan, mycolic acid, or glucose monomycolate antigens; CD1c has the capacity to specifically associate with CD1c-restricted polyisoprenyl glycolipid antigens; and CD1d has the capacity to specifically associate with CD1d-restricted glycophosphatidylinositol (GPI) anchor lipid and glycosylceramide lipid antigens.

The composition-of-matter may comprise an antibody or antibody fragment capable of specifically binding the antigen-presenting portion of any of various particular MHC class I:antigen complexes, for example, an MHC class I:antigen complex having as an MHC class I APM an HLA-A, HLA-B, or HLA-C molecule (referred to herein as "HLA-A: antigen complex", "HLA-B:antigen complex", or "HLA-A: antigen complex", respectively).

While the composition-of-matter may comprise an antibody or antibody fragment capable of specifically binding the antigen-presenting portion of a complex in which the APM is any of various HLA-A molecules, the composition-of-matter is preferably capable of binding the antigen-presenting portion of one in which the HLA-A molecule is HLA-A2, most preferably HLA-A2.1 (alternately termed "HLA-A*201").

As is described and illustrated in Examples section below, a composition-of-matter of the present invention comprising an antibody or antibody fragment capable of specifically binding a complex having an HLA-A2 molecule as APM can be used to effectively practice various embodiments of the present invention.

A composition-of-matter of the present invention may comprise an antibody or antibody fragment capable of specifically binding the antigen-presenting portion of a complex composed of an MHC class I molecule and any of various MHC class I-restricted antigens, which are typically peptides about 9 to 11 amino acid residues in length. Such peptides generally have particular chemical compositions enabling their specific binding to a particular MHC class I molecule (for example, refer to: Bianco A. et al., 1998. J Pept Sci. 4:471; Fairchild P J., 1998. J Pept Sci. 4:182; Falk K. and Rotzschke O., 1993. Semin Immunol. 5:81; Rammensee H G., 1995. Curr Opin Immunol. 7:85; and Hobohm U. and Meyerhans A., 1993. Eur J Immunol. 23:1271).

As described hereinabove, the composition-of-matter of the present invention comprises an antibody or antibody fragment capable of specifically binding the antigen-presenting portion of a particular complex composed of a human APM and an antigen derived from a pathogen.

While the composition-of-matter may comprise an antibody or antibody fragment capable of specifically binding the antigen-presenting portion of a particular complex comprising an APM-restricted antigen derived from essentially any type of pathogen, the pathogen is preferably an intracellular pathogen.

Alternately, the pathogen may a non-intracellular pathogen, such as a bacterium, a fungus, a protozoan, a mycobacterium, a helminth, and the like.

The composition-of-matter may comprise an antibody or antibody fragment capable of specifically binding the antigen-presenting portion of a complex comprising an APM-restricted antigen derived from any of various intracellular pathogens, including a virus, a mycobacterium, a bacterium (such as, for example, *Listeria monocytogenes*), and a protozoan (such as, for example, *Leishmania* or *Trypanosoma*).

Preferably the antibody or antibody fragment is capable of specifically binding the antigen-presenting portion of a complex comprising an APM-restricted antigen derived from a viral pathogen.

Examples of such viral pathogens include retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

While the composition-of-matter may comprise an antibody or antibody fragment capable of specifically binding the antigen-presenting portion of a complex comprising as APM-restricted antigen an antigen derived from any of various retroviruses, the retrovirus is preferably human T lymphotropic virus-1 (HTLV-1; also referred to as human T-cell leukemia virus in the art).

Alternately, the retrovirus may be, for example, HTLV-2, a human immunodeficiency virus (HIV) causing acquired immunodeficiency syndrome (AIDS) such as HIV-1 or HIV-2, or the like.

The composition-of-matter may comprise an antibody or antibody fragment capable of specifically binding the antigen-presenting portion of a complex comprising any of various antigens derived from HTLV-1.

Preferably, a composition-of-matter of the present invention comprising an antibody or antibody fragment capable of specifically binding the antigen-presenting portion of a complex comprising as APM-restricted antigen derived from HTLV-1, an antigen derived from Tax protein.

The composition-of-matter may comprise an antibody or antibody fragment capable of specifically binding the antigen-presenting portion of a complex comprising as APM-restricted antigen any of various Tax protein-derived antigens, and having an antigen binding region comprising any of various amino acid sequences.

Preferably, the antibody or antibody fragment comprises an antibody or antibody fragment: (i) capable of specifically binding the antigen-presenting portion of a complex comprising as Tax protein-derived APM-restricted antigen a peptide comprising amino acid residues 11 to 19 of Tax protein, a peptide having the amino acid sequence set forth in SEQ ID NO: 3, or preferably both; (ii) having an antigen-binding region including a maximal number of amino acid sequences corresponding to one selected from: the group of amino acid sequences set forth in SEQ ID NOs: 14 to 97; or (iii) preferably both.

As is described and illustrated in the Examples section below, a composition-of-matter of the present invention comprising an antibody or antibody fragment: (i) capable of specifically binding a complex having as APM-restricted antigen a peptide comprising amino acid residues 11 to 19 of Tax protein having the amino acid sequence set forth in SEQ ID NO: 3; and (ii) having an antigen-binding region including amino acid sequences corresponding to those set forth in SEQ ID NOs: 14 to 97 can be used to effectively practice various embodiments of the present invention involving using the composition-of-matter for detecting the antigen-presenting portion of the complex, or killing target cells/tissues.

It will, be appreciated that a cell infected with a pathogen, and an APC exposed to the pathogen, or an antigen thereof, may express distinct complexes comprising different APMs and/or different antigens derived from the pathogen, and that hence, the composition-of-matter may be advantageously selected so as to selectively bind one or the other of such cell types. This may be advantageously applied in numerous applications of the present invention, such as, for example, when using the composition-of-matter, as described hereinbelow, to treat a disease associated with a pathogen in an individual by selectively killing/damaging cells infected with the pathogen displaying one particular complex of an APM and an antigen derived from the pathogen without killing/damaging benign or beneficial APCs displaying a different complex of an APM and an antigen derived from the pathogen.

As mentioned hereinabove, depending on the application and purpose, the antibody or antibody fragment may be selected capable of binding the antigen-presenting portion of the complex with a desired affinity.

Preferably, the desired affinity is as high as possible. A composition-of-matter of the present invention comprising an antibody or antibody fragment having as high as possible a binding affinity for the antigen-presenting portion of the complex will generally enable optimally stable conjugation of a functional moiety to the antigen-presenting portion of the complex, and thereby detection of the antigen-presenting portion of the complex with optimal sensitivity, or killing/damaging of target cells/tissues with, optimal efficiency.

Preferably, the affinity is characterized by a dissociation constant ($K_d$) selected from the range of $1 \times 10^{-2}$ molar to $5 \times 10^{-3}$ molar, more preferably $5 \times 10^{-3}$ molar to $5 \times 10^{-4}$ molar, more preferably $5 \times 10^{-4}$ molar to $5 \times 10^{-5}$ molar, more preferably $5 \times 10^{-5}$ molar to $5 \times 10^{-6}$ molar, more preferably $5 \times 10^{-6}$ molar to $5 \times 10^{-7}$ molar, more preferably $5 \times 10^{-7}$ molar to $5 \times 10^{-8}$ molar, more preferably $5 \times 10^{-8}$ molar to $5 \times 10^{-9}$ molar, more preferably $5 \times 10^{-9}$ molar to $5 \times 10^{-10}$ molar, more preferably $5 \times 10^{-10}$ molar to $5 \times 10^{-11}$ molar, more preferably $5 \times 10^{-11}$ molar to $5 \times 10^{-12}$ molar, more preferably $5 \times 10^{-12}$ molar to $5 \times 10^{-13}$ molar, more preferably $5 \times 10^{-13}$ molar to $5 \times 10^{-14}$ molar, more preferably $5 \times 10^{-14}$ molar to $5 \times 10^{-15}$ molar, and most preferably $5 \times 10^{-15}$ molar to $5 \times 10^{-16}$.

As is illustrated in the Examples section below, an antibody or antibody fragment capable of binding the antigen-presenting portion of a complex with an affinity characterized by a dissociation constant of about $10^{-9}$ molar can be generated using the protocol set forth therein.

As is described and illustrated in the Examples section which follows, a composition-of-matter of the present invention comprising an antibody or antibody fragment having a binding affinity for the antigen-presenting portion of the complex characterized by a dissociation constant of about $10^{-9}$ molar can be used to effectively practice various embodiments of the present invention, including those involving using the composition-of-matter for detecting the antigen-presenting portion of the complex, or for killing/damaging target cells/tissues.

Various methods may be employed to obtain the antibody or antibody fragment capable of specifically binding the antigen-presenting portion of the complex.

Preferably, the antibody or antibody fragment is obtained by screening a combinatorial antibody or antibody fragment display library for an element of the library displaying an antibody or antibody fragment capable of binding the antigen-presenting portion of the complex conjugated to a substrate with the desired affinity. Preferably, where the antibody or antibody fragment is an Fab, this may be advantageously effected by screening an Fab-phage library on substrate-immobilized single-chain MHC:peptide complex, preferably as described in the Examples section below. Ample guidance for identifying an antibody or antibody fragment capable of specifically binding the complex is provided in the literature of the art (for example, for generation of a human-derived antibody or antibody fragment refer, for example, to: Chames, P. et al., 2000. Proc. Natl. Acad. Sci. U.S.A. 97:7969-7974; Denkberg, G. et al., 2002. Proc. Natl. Acad. Sci. U.S.A. 99:9421-9426; and Lev, A. et al., 2002. Cancer Res. 62:3184-3194; for generation of a non human-derived antibody or antibody fragment refer, for example, to: Aharoni, R. et al., 1991. Nature 351:147-150; Andersen, P. S. et al., 1996. Proc. Natl. Acad. Sci. U.S. A 93:1820-1824; Dadaglio, G. et al., 1997. Immunity 6:727-738; Day, P. M. et al., 1997. Proc. Natl. Acad. Sci. U.S.A. 94:8064-8069; Krogsgaard, M. et al., 2000. J. Exp. Med. 191:1395-1412; Murphy, D. B. et al., 1989. Nature 338:765-768; Porgador, A. et al., 1997. Immunity 6:715-726; Reiter, Y. et al., Proc. Natl. Acad. Sci. U.S.A. 94:4631-4636; Zhong, G. et al., 1997. Proc. Natl. Acad. Sci. U.S.A. 94:13856-13861; Zhong, G. et al., 1997. J. Exp. Med. 186:673-682; Orlandi D. R. et al., 1989. Proc Natl Acad Sci USA. 86:3833-3837; for a general reference, refer to Winter G. et al., 1991. Nature 349:293-299).

Further guidance for generating the antibody or antibody fragment comprised in the composition-of-matter of the present invention is provided hereinbelow.

It will be appreciated by the ordinarily skilled artisan that generating an antibody or antibody fragment of a desired affinity, for example one characterized by a dissociation constant as high as $10^{-12}$ for a desired antigenic determinant can be achieved using common art techniques.

The composition-of-matter may be used per se or it can be formulated as an active ingredient in a pharmaceutical composition.

Thus, as described hereinabove, the present invention provides, and may be practiced, depending on the application and purpose using, a composition-of-matter comprising: (i) a monoclonal or polyclonal antibody or antibody fragment; (ii) a monomeric or multimeric form of an antibody or antibody fragment; (iii) an antibody or antibody fragment characterized by any of various configurations; (iv) an antibody or antibody fragment or a portion thereof derived from any of various mammalian species; (v) an antibody or antibody fragment capable of specifically binding the antigen-presenting portion of any of various specific human APM:pathogen-derived antigen complexes; and/or (vi) an antibody or antibody fragment capable of specifically binding the antigen-presenting portion of a particular human APM:pathogen-derived antigen complex with a desired affinity.

While further reducing the present invention to practice, genetic sequences encoding an antibody fragment of the present invention were isolated.

Thus, according to another aspect of the present invention there is provided an isolated polynucleotide comprising a nucleic acid sequence encoding an antibody fragment of the present invention.

Depending on the application and purpose, the isolated polynucleotide preferably further comprises a nucleic acid sequence encoding a coat protein of a virus, a detectable moiety, and a toxin.

Preferably, in order to enable generation of a chimeric polypeptide comprising the antibody fragment fused to the coat protein of the virus, the detectable moiety or the toxin, the nucleic acid sequence encoding the polypeptide is translationally fused with that encoding the antibody fragment. Nucleic acid sequences encoding polypeptides may be translationally fused in a polynucleotide by cloning the structural sequences of such nucleic acid sequences in-frame relative to each other in the polynucleotide without intervening transcriptional/translational stop codons, or any other sequences, present between such structural sequences capable of preventing production of a chimeric polypeptide comprising the polypeptides encoded by such structural sequences.

An antibody fragment attached to a coat protein of a virus can be used to generate a virus displaying the antibody fragment by virtue of the antibody fragment being fused to the coat protein of the virus. Generating such a virus may be effected as described in further detail hereinbelow, and in the Examples section which follows.

While various methods may be used to generate the isolated polynucleotide, the isolated polynucleotide is preferably generated as described in the Examples section, below.

As is described and illustrated in the Examples section below, an isolated polynucleotide of the present invention can be used to generate an antibody fragment or conjugate thereof with a coat protein of a virus, a detectable moiety, and/or a toxin suitable for generating the composition-of-matter of the present invention.

While reducing the present invention to practice nucleic acid constructs capable of expressing the polynucleotide of the present invention were isolated or generated.

Thus, the present invention provides a nucleic acid construct comprising the isolated polynucleotide of the present invention and a promoter sequence for directing transcription thereof in a host cell.

While various promoter sequences may be employed capable of directing transcription of the isolated polynucleotide in various types of host cell, depending on the application and purpose, the promoter sequence is preferably capable of directing transcription thereof in a prokaryote.

The promoter sequence may be capable of directing transcription of the polynucleotide in any of various suitable prokaryotes.

Preferably, the prokaryote is *E. coli*.

In order to enable regulatable transcription of the nucleic acid sequence in the host cell, the promoter sequence is preferably further capable of directing inducible transcription of the nucleic acid sequence in the host cell.

Various types of promoter sequences capable of directing transcription or inducible transcription of the polynucleotide in the host cell, such as a suitable *E. coli* cell may be employed.

Preferably, the promoter sequence is a T7 promoter sequence.

It will be appreciated by the skilled artisan that a construct of the present invention comprising a T7 promoter sequence for directing transcription of the polynucleotide can be used to efficiently inducibly express in a suitable *E. coli* host cell the antibody fragment of the present invention, or a conjugate thereof with a coat protein of a virus, detectable moiety, and/or toxin.

Preferably, the nucleic acid construct is isolated or assembled, and is used to inducibly produce the antibody fragment of the present invention in a host cell as is described and demonstrated in the Examples section below.

As described hereinabove, the nucleic acid construct may be expressed in various types of host cells. For example, the nucleic acid construct may be advantageously expressed in a eukaryotic host cell, such as a mammalian cell or a plant cell.

Methods of expressing nucleic acid constructs encoding antibody fragments in eukaryotic cells are widely practiced by the ordinarily skilled artisan.

Plant cells expressing the nucleic acid construct can be used to generate plants expressing the nucleic acid construct, thereby enabling inexpensive and facile production of large quantities of antibody which can be harvested, processed and stored using existant infrastructure.

Expression of the nucleic acid construct of the present invention in plants can be used to produce plants expressing various forms of the composition-of-matter of the present invention, including immunoconjugates such as immunotoxins.

Ample guidance for expressing nucleic acid constructs encoding antibody fragments, such as nucleic acid constructs encoding immunotoxins, in plant cells, and thereby in plants, is provided in the literature of the art (for example, refer to: Peeters K. et al., 2001. Vaccine: 19:2756-61; De Jaeger G. et al., 2000. Plant Mol. Biol. 43:419-28; Fischer R. et al., 2000. J Biol Regul Homeost Agents. 14:83-92; Fischer R. et al., 1999. Biotechnol Appl Biochem. 30:101-8; and Russell D A., 1999. Curr Top Microbiol Immunol. 240:119-38).

While reducing the present invention to practice, viruses comprising the nucleic acid construct of the present invention, and a coat protein fused to an antibody fragment of the present invention were isolated or generated.

Thus, the present invention provides a virus comprising the nucleic acid construct of the present invention and/or a coat protein fused to an antibody fragment of the present invention.

The virus of the present invention can be used in various applications, such as, for example, for selecting an antibody fragment of the present invention having a desired binding affinity/specificity for the antigen-presenting portion of the complex. Alternately, such a virus may be used for propagating the antibody fragment or the nucleic acid construct. Preferably, such propagation is effected by using the virus to infect a host cell.

Any of various types of viruses comprising an antibody fragment of the present invention fused to any of various types of coat protein may be used.

Preferably, the virus is a filamentous phage and the coat protein is pIII.

While various methods may be employed to obtain and utilize the virus, it is preferably obtained and utilized as described and demonstrated in the Examples section which follows.

While reducing the present invention to practice, host cells comprising the nucleic acid construct were generated and used to produce antibody fragments of the present invention.

Thus, the present invention provides a host cell comprising the nucleic acid construct.

While the host cell may be advantageously used in various applications, it is preferably used to produce the antibody fragment, as mentioned hereinabove. Alternately, the host cell may be used to propagate the nucleic acid construct.

Various types of host cell may be used to practice the present invention, depending on the application and purpose.

Preferably, the host cell is a prokaryotic cell.

Alternately, the host cell may be a mammalian cell (please refer to the antibody/antibody fragment production guidelines herein for description of suitable mammalian cells, and methods of their use).

While any of various types of prokaryotic host cells may be utilized, the prokaryotic cell is preferably an *E. coli* cell.

While various methods may be employed to obtain and utilize the *E. coli* host cell, for example, to produce the antibody or antibody fragment, it is preferably obtained and utilized as described and demonstrated in the Examples section which follows.

While reducing the present invention to practice the capacity of the composition-of-matter to enable specific detection of the antigen-presenting portion of a particular human APM: pathogen-derived antigen complex was demonstrated.

Thus, according to another aspect of the present invention there is provided a method of detecting the antigen-presenting portion of the complex.

The method is effected by exposing the antigen-presenting portion of the complex to a composition-of-matter of the present invention to thereby obtain a conjugate of the antigen-presenting portion of the complex and the antibody or antibody, fragment comprised in the composition-of-matter. Once the conjugate is formed, the method further comprises detecting the antibody or antibody fragment of the conjugate so as to thereby detect the antigen-presenting portion of the complex.

The method according to this aspect of the present invention can be used to detect the antigen-presenting portion of the complex in any of various contexts and applications.

In particular, as described hereinbelow, the method can be used to diagnose an infection by a pathogen in an individual.

Depending on the application and purpose, various methods may be utilized to expose the antigen-presenting portion of the complex to the composition-of-matter, according to the teachings of the present invention.

When using the method for detecting the antigen-presenting portion of a complex displayed/expressed by target cells/tissues, or of a complex immobilized on a surface, the antigen-presenting portion of the complex is preferably exposed to the composition-of-matter by exposing the target cells/tissues, or the surface-immobilized antigen-presenting portion of the complex, respectively, to the composition-of-matter.

For certain applications, the biological sample may be advantageously obtained from an individual prior to contacting the composition-of-matter with the biological sample. Alternately, the composition-of-matter may be contacted with the biological sample by administering the composition-of-matter to the individual.

As described hereinabove, once the composition-of-matter and the antigen-presenting portion of the complex exposed to the composition-of-matter form the conjugate, the method further comprises detecting the antibody or antibody fragment of the conjugate so as to thereby detect the antigen-presenting portion of the complex.

While various methods may be employed to detect the antibody or antibody fragment of the antigen-presenting portion of the complex, the antigen-presenting portion of the complex is preferably detected by using a composition-of-matter of the present invention comprising an antibody or antibody fragment attached a detectable moiety, and detecting the antibody or antibody fragment by detecting the detectable moiety attached thereto.

As described hereinabove, various detectable moieties may be used to detect the antigen-presenting portion of the complex in the context of various detection assays, depending on the application and purpose.

Preferably, the method according to this aspect of the present invention is used to detect the antigen-presenting portion of a complex in a biological sample. Alternately, the method may be used to detect the antigen-presenting portion of a complex immobilized on a non-cellular surface, such as an the surface of an ELISA plate.

While the method may be used to detect the antigen-presenting portion of the complex in essentially any type of biological sample, it is preferably applied to detect the antigen-presenting portion of a complex displayed/expressed by target cells/tissues.

Preferably, the target cells are pathogen infected cells displaying the complex, or APCs displaying the complex, such as professional APCs, dendritic cells, B lymphocytes, granulocytes, neutrophils, basophils, eosinophils, monocytes, macrophages, and mast cells.

It will be appreciated that since, as described hereinabove, the composition-of-matter may comprise an antibody or antibody fragment capable of specifically binding a complex comprising as, APM-restricted antigen an antigen derived from essentially any pathogen, the method according to this aspect of the present invention can be used to detect a complex comprising as APM-restricted antigen, an antigen derived from essentially any pathogen.

Preferably, the method is used to detect target cells displaying/expressing a particular complex comprising as APM-restricted antigen, an HTLV-1-derived antigen Preferably, the method according to this aspect of the present invention is effected as described in the Examples section which follows.

As is demonstrated in the Examples section below, practicing the method according to the protocol set forth therein can be used in numerous contexts to detect with optimal specificity and sensitivity cells displaying a particular complex comprising as APM-restricted antigen, an HTLV-1-derived antigen, or such a complex immobilized on a non cellular surface.

Thus, the method according to this aspect of the present invention may be used to effectively and potently diagnose and characterize an infection by a pathogen in an individual.

It will be appreciated that since, as described hereinabove, this aspect of method of the present invention can be used to detect essentially any complex in essentially any context with optimal specificity and/or sensitivity, the method according to this aspect of the present invention can be used to optimally diagnose and characterize essentially any infection associated with essentially any pathogen.

For example, as described in the Examples section below, the method according to this aspect of the present invention can be used to optimally detect an APM:retrovirus-derived antigen. Thus, the method can be used to optimally detect in an individual an infection by a retrovirus. Retrovirus are associated with a wide variety of diseases including an array of malignancies, immunodeficiencies (notably AIDS), and neurological disorders, and syndromes as seemingly diverse as arthritis, osteopetrosis, and anemia. Thus, the method according to this aspect of the present invention can be used, for example, to optimally diagnose essentially all such diseases in an individual.

Preferably, the method according to this aspect of the present invention is used to diagnose an HTLV-1 infection, or a disease associated with such infection, in an individual, since, as described and demonstrated, in the Examples section which follows, the method according to this aspect of the present invention can be used to detect with optimal sensitivity and specificity a target cell displaying a complex comprising as APM-restricted antigen, an HTLV-1-derived antigen. Diseases associated with HTLV-1 infection which may diagnosed and characterized using this according to this aspect of the present invention include adult T-lymphocyte leukemia/lymphoma (ATLL; Yoshida M. et al., 1982. Proc Natl Acad Sci USA. 79:2031-2035), Sjogren's syndrome, inflammatory arthropathies, polymyositis, and pneumopathies (Coscoy L. et al., 1998. Virology 248: 332-341).

Most preferably, this aspect of the present invention can be used for diagnosis and characterization of HTLV-1 associated myelopathy/tropical virus spastic paraparesis (HAM/TSP; Osame M. et al., 1986. Lancet 1:1031-1032), as is described in Example 2 of the Examples section which follows.

While reducing the present invention to practice, the capacity of the composition-of-matter of the present invention to enable killing/damaging of target cells was demonstrated.

Thus, according to a further aspect of the present invention there is provided a method of killing or damaging target cells.

According to the teachings of the present invention, the method is effected by exposing the target cells to the composition-of-matter of the present invention.

The method may be effected so as to kill various types of target cells in various ways, depending on the application and purpose.

Preferably, the method is effected by exposing target cells to a composition-of-matter of the present invention comprising an antibody or antibody fragment attached to a toxin, so as to thereby kill/damage the target cells via the toxin.

Alternately, in an in-vivo context or an in-vitro equivalent thereof, the method may be effected by exposing target cells to a composition-of-matter of the present invention comprising an antibody or antibody fragment including an Fc region, or portion thereof, capable of specifically binding a molecule capable of initiating an immune response, such as a complement cascade or ADCC, directed against target cells bound by such an antibody or antibody fragment, as described hereinabove.

While the method according to this aspect of the present invention can be used for killing/damaging target cells in any of various contexts and applications, it is preferably employed to kill/damage target cells so as to treat a disease associated with a pathogen in an individual.

It will be appreciated that the method may also be used to kill/damage target cells in-vitro or in-vivo in an animal model, in particular to test and/or optimize killing/damaging of target cells using the composition-of-matter. Such testing and/or optimizing killing/damaging of target cells using the composition-of-matter may be advantageously applied towards optimizing treatment of the disease in the individual using the composition-of-matter.

When using the method according to this aspect of the present invention for optimizing use of the composition-of-matter to kill/damage target cells for treating the disease, the method may be advantageously effected by obtaining the target cells from the individual. One of ordinary skill in the art, such as a physician, will possess the necessary expertise to obtain target cells from an individual.

Various types of target cells may be obtained from the individual for optimizing use of the composition-of-matter to kill/damage target cells. Preferably, such target cells are cells infected with the pathogen since such cells will be of particular utility for optimizing killing of target cells infected with the pathogen, and hence for optimizing treatment of the disease in the individual.

It will be appreciated that since, as described hereinabove, the composition-of-matter may comprise an antibody or antibody fragment capable of binding with optimal specificity and affinity a complex comprising as APM-restricted antigen an antigen derived from essentially any pathogen, the method according to this aspect of the present invention can be used to kill/damage cells displaying/expressing a complex comprising as APM-restricted antigen, an antigen derived from essentially any pathogen with optimal efficiency and specificity.

Preferably, the method is used to kill/damage target cells displaying/expressing a particular complex comprising as APM-restricted antigen, an HTLV-1-derived antigen Preferably the method according to this aspect of the present invention is effected as described in the Examples section which follows.

As is demonstrated in the Examples section below, practicing the method according to the protocol set forth therein can be used to kill with optimal efficiency and specificity cells displaying a particular complex comprising as APM-restricted antigen, an HTLV-1-derived antigen.

Thus, the present invention provides a method of treating a disease associated with a pathogen in an individual.

The method is effected by administering to the individual a therapeutically effective amount of a pharmaceutical composition comprising as an active ingredient a composition-of-matter of the present invention comprising as APM-derived antigen, an antigen derived from the pathogen.

As described in detail hereinbelow, the pharmaceutical composition may be administered in various ways.

As described hereinabove, the method according to this aspect of the present invention is preferably effected using a composition-of-matter comprising an immunotoxin.

Ample guidance for treating a disease using an immunotoxin is provided in the literature of the art (for example, for general references refer to: Knechtle S J. 2001, Philos Trans R Soc Lond B Biol Sci. 356:681-93; Kreitman R J., 2001. Methods Mol. Biol. 166:111-23; Brinkmann U., 2000. in-vivo 14:21-7; Ghetie M A and Vitetta E S., 1994. Curr Opin Immunol. 6:707-14; Wu M., 1997. Br J Cancer. 75:1347-55; Hall W A. 1996, Neurosurg Clin N Am. 7:537-46; Boon, T. and van der Bruggen, P., 1996. J. Exp. Med. 183:725-729; Renkvist, N. et al., 2001. Cancer Immunol Immunother. 50:3-15; Rosenberg, S. A., 2001. Nature 411:380-384; and U.S. Pat. No. 5,677,274; for treatment of acquired immunodeficiency syndrome (AIDS), refer, for example, to Chaplin J W., 1999. Med Hypotheses 52:133-46; for treatment of brain tumors, refer, for example, to Hall W A., 2001. Methods Mol. Biol. 166:139-54; for treatment of hematological malignancies, refer, for example to: Pasqualucci L. et al., 1995. Haematologica 80:546-56; Grossbard M L. et al.,. Clin Immunol Immunopathol. 76:107-14; and Grossbard M L and Nadler L M., 1994. Semin Hematol. 31:88-97; for treatment of carcinomas, refer, for example, to Siegall C B., 1995. Semin Cancer Biol. 6:289-95; for treatment of cancer, refer, for example, to: Frankel A E., 1993. Oncology (Huntingt) 7:69-78; and Pai L H. and Pastan I., 1993. JAMA. 269:78-81).

The method can be used to treat various types of diseases associated with a pathogen using various methodologies taught by the present invention.

Preferably, the method is used to treat a disease associated with a pathogen by killing/damaging pathogen infected cells. This may be advantageously performed where the pathogenesis of the disease derives predominantly from the pathogen infected, cells.

Alternately, the method may be used to treat the disease, where the disease involves a pathogenic immune response directed against pathogen-infected cells by pathogenic T-lymphocytes activated by pathogenic APCs displaying/expressing a complex comprising as APM-restricted antigen, an antigen derived from the pathogen. This is preferably effected, as described hereinabove, by using the composition-of-matter to kill/damage such pathogenic APCs. Alternately, the pathogenic immune response mediated by such pathogenic APCs may be inhibited as described hereinabove, by using a composition-of-matter of the present invention comprising an antibody or antibody fragment capable of specifically binding the pathogenic complex so as to thereby block activation of the pathogenic T-lymphocytes via engagement of the TCRs thereof by the complex.

It will be appreciated that since, as described hereinabove, this aspect of method of the present invention can be used to kill with optimal efficiency and specificity cells displaying/expressing essentially any particular complex, the method according to this aspect of the present invention can be used to optimally treat essentially any infection associated with essentially any pathogen in an individual.

For example, as described in the Examples section below, the method according to this aspect of the present invention can be used to kill/damage with optimal efficiency and specificity cells displaying a complex comprising as APM-restricted antigen, an antigen derived from a retrovirus. Thus, the method can be used to optimally treat, for example, an infection associated with a retrovirus in an individual Thus, the method according to this aspect of the present invention can be used, for example, to optimally treat the broad range of diseases associated with a retroviral infection described hereinabove.

Preferably, the method according to this aspect of the present invention is used to treat an HTLV-1 infection in an individual, since, as described and demonstrated in the Examples section which follows, the method according to this aspect of the present invention can be used to kill with optimal efficiency and specificity target cells displaying a complex comprising as APM-restricted antigen, an HTLV-1-derived antigen.

As described hereinabove, the antibody or antibody fragment of the present invention may be generated in numerous ways.

A monoclonal or polyclonal antibody or antibody fragment of the present invention may be generated via methods employing induction of in-vivo production of antibody or antibody fragment molecules, or culturing of antibody- or antibody fragment producing cell lines. Ample guidance for practicing such methods is provided in the literature, of the art [for example, refer to Harlow and Lane, "Antibodies: A Laboratory Manual", Cold Spring Harbor Laboratory, New York, (1988)].

Cell culture-based methods of generating antibodies include the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc Natl Acad Sci USA. 80:2026-2030; Cole S P. et al., 1984. Mol. Cell. Biol. 62:109-120).

Generating an antibody or antibody or antibody fragment of the present invention in-vivo may be advantageously effected by repeated injection of a target antigen (e.g., one comprising the antigen-presenting portion of the complex) into a mammal in the presence of adjuvants according to a schedule which boosts production of antibodies in the serum. In cases wherein the target antigen is too small to elicit an adequate immunogenic response (referred to as a "hapten" in the art), the hapten can be coupled to an antigenically neutral carrier such as keyhole limpet hemocyanin (KLH) or serum albumin [e.g., bovine serum albumin (BSA)] carriers (for example, refer to: U.S. Pat. Nos. 5,189,178 and 5,239,078). Coupling a hapten to a carrier can be effected using various methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling both homobifunctional and heterobifunctional linkers are available from Pierce Chemical Company, Rockford, Ill. The resulting immunogenic complex can then be injected into suitable mammalian subjects such as mice, rabbits, and the like. Following in-vivo generation of an antibody, its serum titer in the host mammal can readily be measured using immunoassay procedures which are well known in the art. Such a polyclonal antibody containing anti-serum may be utilized as such, following purification thereof to generate a pure polyclonal or monoclonal antibody preparation. Such an anti-serum or purified antibody preparation may also be modified in various ways, depending on the application and purpose, prior to use. Genetic sequences encoding an antibody isolated from such an anti-serum may be determined using standard art techniques, and used to recombinantly produce the antibody or a modification thereof, such as an antibody fragment.

An antibody fragment of the present invention can be obtained using various methods well known in the art. For example, such an antibody fragment can be prepared by proteolytic hydrolysis of a parental antibody or by recombinant expression in E. coli or mammalian cells (e.g., Chinese hamster ovary cell culture or other protein expression systems) of DNA encoding the fragment.

An $F(ab')_2$ antibody fragment can be produced by enzymatic cleavage of a parental antibody with pepsin to provide a 5S fragment. This fragment can be further cleaved using a thiol reducing agent, and optionally a blocking group for the sulfhydryl groups resulting from cleavage of disulfide linkages to produce a 3.5S monovalent Fab' antibody fragment.

Enzymatic cleavage of a parental antibody with pepsin can be used to directly produce two monovalent Fab' fragments and an Fc fragment. Ample guidance for practicing such methods is provided in the literature of the art (for example, refer to: Goldenberg, U.S. Pat. Nos. 4,036,945 and 4,331,647; Porter R R., 1959. Biochem J. 73:119-126).

As described hereinabove, an Fv is composed of paired heavy chain variable and light chain variable domains. This association may be noncovalent (for example, refer to Inbar et al., 1972. Proc. Natl. Acad. Sci. U.S.A. 69:2659-62). Alternatively, as described hereinabove the variable domains can be linked to generate a single chain Fv by an intermolecular disulfide bond, or such chains may be covalently cross-linked using chemicals such as glutaraldehyde. A single chain Fv may advantageously prepared by constructing a structural gene comprising DNA sequences encoding the heavy chain variable domain and the light chain variable domain connected by an oligonucleotide encoding a peptide linker. The structural gene is inserted into an expression vector, which is subsequently introduced into a host cell such as E. coli which will then synthesize such a single chain Fv. Ample guidance for practicing such methods of producing a single chain Fv is provided in the literature of the art (for example, refer to: Whitlow and Filpula, 1991. Methods 2:97-105; Bird et al., 1988. Science 242:423-426; Pack et al., 1993. Bio/Technology 11:1271-77; and Ladner et al., U.S. Pat. No. 4,946,778).

Other methods of cleaving an antibody, such as separation of heavy chains to form monovalent light-heavy chain fragments, further cleavage of fragments, or other enzymatic, chemical, or genetic techniques may also be used, so long as the fragment bind to the target antigen that is recognized by the intact antibody.

A polypeptide comprising a complementarity determining region (CDR) peptide of an antibody can be obtained via recombinant techniques using genetic sequences encoding such a CDR, for example, by RT-PCR of mRNA of an antibody-producing cell. Ample guidance for practicing such methods is provided in the literature of the art (for example, refer to Larrick and Fry, 1991. Methods 2:106-10).

It will be appreciated that for human therapy or diagnostics, a humanized antibody or antibody fragment may be advantageously used. Humanized non human (e.g., murine) antibodies are genetically engineered chimeric antibodies or antibody fragments having—preferably minimal—portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non human antibody and all or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596). Methods for humanizing non human antibodies or antibody fragments are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies. Human antibodies or antibody fragments can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147:86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368: 812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

Once an antibody or antibody or antibody fragment is obtained, it may be advantageously tested for specific binding to the antigen-presenting portion of the complex, for example via ELISA, using surface-immobilized target complex, as described in further detail hereinbelow, and in the Examples section which follows. Following confirmation of specific binding of the antibody or antibody fragment to the antigen-presenting portion of the complex, various methods may be employed to modify the antibody or antibody fragment to display the desired binding affinity for the antigen-presenting portion of the complex. Such methods include those based on affinity maturation (for example, refer to: Chowdhury, P. S., and Pastan, I., 1999. Nat. Biotechnol. 17:568-72).

As described hereinabove, the present invention can be used to treat a disease associated with an infection by a pathogen in an individual by administering a pharmaceutical composition comprising as an active ingredient a composition-of-matter of the present invention.

As used herein a "pharmaceutical composition" refers to a preparation of one or more of the active ingredients described herein with other chemical components such as physiologically suitable carriers and excipients. The purpose of a pharmaceutical composition is to facilitate administration of active ingredients to an organism.

Herein the term "active ingredients" refers to the composition-of-matter accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered active ingredients. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Alternatively, for oral administration, the pharmaceutical composition may comprise an edible part of a plant containing, for example the immunotoxin of the present invention, as described hereinabove. Hence an individual may consume such an immunotoxin in the form of a plant food endogenously expressing the immunotoxin.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g. gelatin for use in a dispenser may be formulated containing a powder mix of the active ingredients and a suitable powder base such as lactose or starch.

The pharmaceutical composition described herein may be formulated for parenteral administration, e.g., by bolus, injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (nucleic acid construct) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients sufficient to exert a desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is expected that during the life of this patent many relevant medical diagnostic techniques will be developed and the scope of the phrase "method of detecting" is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Generation of Reagents Capable of Binding with Optimal Affinity and Specificity Particular Human APM:Pathogen-derived Antigen Complexes Applicable Towards Optimal Diagnosis, Characterization, and Treatment of Human Pathogen Infections Diseases associated with a pathogen infection, such as a viral infection, include numerous debilitating or lethal diseases of major medical and economic impact, including influenza, the common cold, and acquired immunodeficiency syndrome (AIDS). One theoretically potent approach which has been proposed for diagnosing, characterizing, and treating such pathogen mediated diseases involves using compounds capable of binding specific human antigen-presenting molecule (APM):pathogen-derived peptide complexes. Such compounds could be used to identify and characterize pathogen infected cells/tissues, or APCs exposed to viral antigens with optimal specificity, to deliver cytotoxic agents with optimal selectivity and efficiency to pathogen infected cells, and to serve as uniquely potent tools for studying pathogen mediated pathogenesis involving viral antigen presentation. However, all prior art approaches of generating compounds capable of specifically binding such complexes have failed to provide compounds capable of binding with optimal affinity/specificity human APM:pathogen-derived antigen complexes. While reducing the present invention to practice, the present inventors have unexpectedly uncovered such compounds, as follows.

Materials and Methods:

Cell lines and antibodies: RMA-S-HHD is a TAP2 deficient murine cell line which expresses HLA-A2.1/Db-beta$_2$-microgulobulin single-chain (Pascolo, S. et al., 1997. J. Exp. Med. 185:2043-2051). JY is a TAP and HLA-A2 positive EBV transformed B lymphoblast cell line. APD is an HLA-A2 negative/HLA-A1 positive B cell line. HUT 102 and RSCD4 are HLA-A2 negative and positive, HTLV-1 infected human CD4 positive T-lymphocyte cell lines, respectively.

G2D12 is an anti HLA-A2:G9-154 complex Fab used as a negative control (peptide G9-154 is derived from the melanoma specific gp100 protein). Monoclonal antibodies w6/32 and BB7.2 specifically bind correctly folded, peptide bound HLA (pan HLA), and HLA-A2, respectively.

Production of biotinylated soluble HL4-A2:Tax$_{11-19}$ complex: Soluble biotinylated HLA-A2:Tax$_{11-19}$ complex was generated as previously described (Denkberg, G. et al., 2000. Eur. J. Immunol. 30:3522-3532). Briefly, a construct was assembled for expression of single chain MHC fusion protein containing HLA-A2.1 (alternately termed HLA-A*201) fused to beta$_2$-microglobulin, the BirA recognition sequence for site specific biotinylation at the C-terminus, and a hexahistidine tag fused to the CH1 domain of the Fd chain. In this single chain fusion protein, HLA-A2 and beta$_2$-microglobulin are fused via a flexible peptide linker. For expression of this single chain E. coli, transformants were generated using the construct, inclusion bodies containing the fusion protein were isolated from the periplasmic fraction of transformants by nickel affinity chromatography, and the fusion protein from inclusion bodies was refolded in-vitro in the presence of a 5 to 10 fold molar excess of HLA-A2 restricted peptide so as to generate soluble, correctly folded and assembled HLA-A2:Tax$_{11-19}$ complexes. Correctly folded HLA-A2:Tax$_{11-19}$ complex was isolated and purified by anion exchange Q-Sepharose chromatography (Pharmacia) followed by site specific biotinylation using the BirA enzyme (Avidity, Denver, Colo.), as previously described (Altman J. D. et al., 1996. Science 274:94-96). The homogeneity and purity of the HLA-A2:Tax$_{11-19}$ complex were analyzed by various biochemical means including SDS-PAGE, size exclusion chromatography, and enzyme linked immunosorbent assay (ELISA), as previously described (Denkberg, G. et al., 2000. Eur. J. Immunol. 30:3522-3532).

Selection of Fab-phages capable of specifically binding HL4-A2:Tax$_{11-19}$ complex: Selection of Fab-phages (Fab-phages) on surface immobilized biotinylated MHC:peptide complex was performed as previously described (Denkberg, G. et al., 2002. Proc. Natl. Acad. Sci. U.S.A. 99:9421-9426; Lev, A. et al., 2002. Cancer Res. 62:3184-3194). Briefly, a large human Fab library containing $3.7 \times 10^{10}$ different Fab clones (de Haard, H. J. et al., 1999. J. Biol. Chem. 274:18218-18230) was used for the selection. Aliquots of $10^{13}$ phages were pre incubated with 200 microliters of streptavidin coated paramagnetic beads (Dynal, Oslo) to deplete streptavidin binders. The remaining phages were then panned using decreasing amounts of surface immobilized biotinylated HLA-A2:Tax$_{11-19}$ complex as binding target (500 nanomolar for the first round, and 100 nanomolar for the following rounds). Bound phages were eluted with 100 millimolar triethylamine, and the eluate was neutralized with 1 molar Tris.HCl pH 7.4. Neutralized phages were then used to infect E. coli TG1 cells (OD$_{600}$=0.5) by incubation for 30 minutes at 37 degrees centigrade.

The diversity of the selected antibodies was determined by DNA fingerprinting. The Fab DNA of different clones was PCR amplified using the primers pUC-reverse [5'-AGCG-GATAACAATTTCACACAGG-3' (SEQ ID NO: 1)] and fd-tet-seq24 [5'-TTTGTCGTCTTTCCAGACGTTAGT-3' (SEQ ID NO: 2)] followed by digestion with BstNI (New England Biolabs, U.S.A.) by incubation for 2 hours at 60 degrees centigrade. Reaction products were analyzed by agarose gel electrophoresis.

Expression and purification of soluble recombinant Fab's: Fab's were expressed and purified as previously described (Denkberg, G. et al., 2000. Eur. J. Immunol. 30:3522-3532). Briefly, cultures of TG1 or BL21 cells transformed with constructs for expression of Fab's under the control of isopropyl beta-D-thiogalactoside (IPTG) inducible regulatory sequences were grown to $OD_{600}$=0.8 to 1.0. Cultures were induced to express recombinant Fab by addition of 1 millimolar IPTG and further culturing for 3 to 4 hours at 30 degrees centigrade. Periplasmic content was released using B-PER solution (Pierce), and applied onto a pre-washed TALON column (Clontech). Bound Fab was eluted from the column using 0.5 ml of 100 millimolar imidazole dissolved in phosphate buffered saline solution, and dialyzed twice against phosphate buffered saline solution by overnight incubations at 4 degrees centigrade to remove residual imidazole.

ELISA of Fab-phage clones and purified Fab's: The binding specificities of individual Fab-phage clones and soluble Fab's for HLA-A2:$Tax_{11-19}$ complex were determined by ELISA using biotinylated HLA-A2:$Tax_{11-19}$ complex as binding target. ELISA plates (Falcon) were coated overnight with BSA-biotin (1 microgram/well). Coated plates were washed and incubated for 1 hour at room temperature with streptavidin (1 microgram/well). After extensive washing, the plates were incubated for 1 hour at room temperature with 0.5 microgram of HLA-A2:Tax-$_{11-19}$ complex. The plates were blocked for 30 minutes at room temperature with 2 percent skim to milk-phosphate buffered saline solution, and were subsequently incubated for 1 hour at room temperature with about $10^9$ phage clones per well, or with various concentrations of soluble purified Fab. The plates were washed and incubated with horseradish peroxidase conjugated anti human Fab antibody for soluble Fab, or with horseradish peroxidase conjugated anti M13 phage antibody for Fab-phages. Detection was performed using TMB reagent (Sigma). The amino acid sequences of the $Tax_{11-19}$ target peptide and of HLA-A2 restricted negative control peptides used for screening the Fab-phage clones or purified Fab's are shown in Table 1.

TABLE 1

HLA-A2 restricted peptides used for screening Fab-phage clones or purified soluble Fab's.

| Sequence | | Protein | Peptide position |
|---|---|---|---|
| LLFGYPVYV | (SEQ ID NO: 3) | TAX | 11-19 |
| LLLTVLTVV | (SEQ ID NO: 4) | MUC1-D6 | 3-21 |
| NLTISDVSV | (SEQ ID NO: 5) | MUC1-A7 | 130-138 |
| NLVPMVATV | (SEQ ID NO: 6) | CMV-pp65 | 495-503 |
| SVRDRLARL | (SEQ ID NO: 7) | EBNA-3A | 596-604 |
| ILAKFLHWL | (SEQ ID NO: 8) | hTERT | 540-548 |
| RLVDDFLLV | (SEQ ID NO: 9) | hTERT | 865-873 |
| IMDQVPFSV | (SEQ ID NO: 10) | Gp100 | 209-217 |
| YLEPGPVTV | (SEQ ID NO: 11) | Gp100 | 280-288 |
| KTWGQVWQV | (SEQ ID NO: 12) | Gp100 | 154-162 |
| EAAGIGILTV | (SEQ ID NO: 13) | MART | 6-35 |

Production of fluorescent Fab T3F2 tetramer: The genes encoding the light and heavy chains of Fab, T3F2 were cloned separately into a pET expression vector for T7-promoter regulated expression of cloned inserts. The light chain gene was engineered as a fusion protein including the BirA recognition sequence for site specific biotinylation at the carboxy terminus (T3F2 light-BirA). These constructs were expressed separately in E. coli BL21 cells and upon induction with IPTG, intracellular inclusion bodies containing large amounts of the recombinant protein were generated. Inclusion bodies containing the T3F2 chains were purified, solubilized, reduced, and refolded in-vivo at a 1:1 ratio in a redox shuffling buffer system containing 0.1 molar Tris.HCl, 0.5 molar arginine, and 90 micromolar oxidized glutathione at pH 8.0. Correctly folded Fab was then isolated and purified by anion exchange MonoQ chromatography (Pharmacia). The Fab peak fractions were concentrated using Centricon-30 (Amicon) to 1 milligram per milliliter and the buffer was exchanged to 10 millimolar Tris.HCl pH 8.0. Biotinylation was performed using the BirA enzyme (Avidity, Denver, Colo.), as previously described (Denkberg, G. et al., 2000. Eur. J. Immunol. 30:3522-3532; Altman J. D. et al., 1996. Science 274:94-96). Excess biotin was removed from biotinylated Fab using a G-25 desalting column. Phycoerythrin labeled streptavidin (Jackson-Immunoresearch) was added at a molar ratio of 1:4 to produce fluorescent tetramers of the biotinylated Fab.

Flow Cytometry: The B cell line RMA-S-HHD transformant expressing HLA-A2-beta$_2$-microglobulin, the EBV transformed HLA-A2 positive JY cells, mature human HLA-M positive dendritic cells, and the HLA-A2 negative B cell line APD-70 were used to determine the reactivity: of the recombinant Fab's with cell surface expressed HLA-A2: $Tax_{11-19}$ complex. Peptide pulsing was performed as indicated. Briefly, about $10^6$ cells were washed twice with serum-free RPMI and incubated overnight at 26 degrees centigrade or 37 degrees centigrade, respectively, in medium containing 1 to 50 micromolar of the peptide. The RMA-S-HHD cells were subsequently incubated at 37 degrees centigrade for 2 to 3 hours to stabilize cell surface expression of HLA-A2:$Tax_{11-19}$ complex.

Alternatively, $20\times10^6$ JY or APD cells were transfected with 20 micrograms of the eukaryotic expression vector pcDNA 3.1 (Invitrogen) encoding the TAX protein cDNA (pcTAX). The cDNA was a kind gift of Drs. M. Yutsudo (Osaka University) and T. Oka, (Okayama University). Twelve to twenty four hours after transfection, cells were incubated for 60 to 90 minutes at 4 degrees centigrade with recombinant Fab (20 microgram per milliliter) in a volume of 100 microliters. After incubation, the primarily labeled cells were washed three times, and incubated with 1 microgram of anti human Fab antibody (Jackson-Immunoresearch). The secondarily labeled cells were then washed three times, and resuspended in ice cold phosphate buffered saline solution. All subsequent washes and incubations were performed under ice cold conditions. The cells were analyzed using a FACStar flow cytometer (Becton Dickinson) and the results were analyzed using WINANOMOLARDI software (Trotter J., http://facs.scripps.edu). Flow cytometric analysis of peptide loaded cells was performed as previously described (Denkberg, G. et al., 2002. Proc. Natl. Acad. Sci. U.S.A. 99:9421-9426; Lev, A. et al., 2002. Cancer Res. 62:3184-3194).

Competition binding assays: Flexible ELISA plates were coated with BSA-biotin and 10 micrograms of HLA-A2: $Tax_{11-19}$ complex in a volume of 100 microliters were immobilized, as previously described (Lev, A. et al., 2002. Cancer Res. 62:3184-3194; Cohen, C J. et al., 2002. Cancer Res. 62:5835-5844). Binding of soluble purified Fab was performed via a competitive binding analysis in which the ability of purified Fab to inhibit the binding of [125]iodine-Fab to specific surface immobilized HLA-A2:$Tax_{11-19}$ complex was examined. Recombinant Fab was radiolabeled with [125] iodine using the Bolton-Hunter reagent. The radiolabeled Fab was added to the wells as a tracer ($3\times10^5$ to $5\times10^5$ counts per minute per well) in the presence of increasing concentrations of unlabeled Fab as competitor. Binding assays were performed by incubation at room temperature for 1 hour in phosphate buffered saline solution. After incubation, plates were washed 5 times with phosphate buffered saline solution and bound radioactivity was determined using a gamma counter. The apparent affinity of Fab was determined by extrapolating the concentration of competitor necessary to achieve 50 percent inhibition of binding of [125]iodine labeled Fab to the immobilized HLA-A2:$Tax_{11-19}$ complex. Non specific binding was determined by adding a 20- to 40-fold excess of unlabeled Fab.

Enzyme-linked immunohistochemical analysis of specific human MHC:viral peptide complexes: JY or APD cells were transfected with pcTAX vector, as described above. After 24 hours, transfected cells were incubated with 20 micrograms of horseradish peroxidase (HRP) labeled T3F2 Fab tetramer for 1 hour on ice in RMPI supplemented with 10 percent FCS. The cell suspension was applied onto glass slides precoated with 0.1 percent poly-L-lysine (Sigma), as previously described [Harlow, E., and Lane, D. in: "Antibodies: A Laboratory Manual". Cold Spring Harbor, Cold Spring Harbor Laboratory Press (1988)], and the slides were incubated for 1 hour at room temperature. Following incubation, the slides were washed three times with phosphate buffered saline solution, and incubated with a DAB+ solution (Dako) for 1 minute followed by washing with phosphate buffered saline solution to remove excess staining reagent.

Expression and purification of soluble recombinant anti HLA-A2:$Tax_{11-19}$ complex immunotoxin: The DNA sequences encoding the heavy and light chain variable domains of T3F2 were recovered from Fab-phage clone by PCR amplification and subcloned using the NcoI-NotI fragment into bacterial expression vector pIB-NN, for expression of T3F2-PE38, a single chain immunotoxin consisting of the toxin PE38 KDEL fused to a single chain Fv of T3F2 via the carboxy terminus of the light chain variable region. Toxin PE38 KDEL consists of the translocation and ADP-ribosylation domains of *Pseudomonas* exotoxin A. Expression in BL21 IDE3 cells, refolding from inclusion bodies, and purification of the T3F2-PE38 was performed as previously described (Brinkmann U. et al., 1991. Proc. Natl. Acad. Sci. U.S.A. 88:8616-20).

Experimental Results:

Generation of anti HLA-A2:$Tax_{11-19}$ complex antibodies: The immune response in HTLV-1 infected patients carrying the MHC class I allele HLA-A2 is primarily directed against the HLA-A2 restricted Tax protein-derived $Tax_{11-19}$ peptide by clonal expansion of HTLV-1 reactive CD8 positive T-lymphocytes.

Recombinant HLA-A2:$Tax_{11-19}$ complex was generated using a previously described single chain MHC-$beta_2$-microglobulin fusion protein expression construct (Denkberg, G. et al., 2000. Eur. J. Immunol. 30:3522-3532). Using this construct, the extracellular domains of HLA-A2 are fused to $beta_2$-microglobulin using a flexible 15 amino acid long peptide linker. The HLA-A2:$Tax_{11-19}$ complex was produced by in-vitro refolding of inclusion bodies in the presence of $Tax_{11-19}$ peptide. The refolded HLA-A2:$Tax_{11-19}$ complex was found to be very pure, homogenous, and monomeric, as determined by SDS-PAGE and size-exclusion chromatography analyses (data not shown). Recombinant HLA-A2:$Tax_{11-19}$ complex generated by this strategy has been previously characterized in detail with respect to its biochemical, biophysical, and biological properties, and was found to be correctly folded and functional [Denkberg, G. et al., 2000. Eur. J. Immunol. 30:3522-3532; Harlow, E., and Lane, D. in: "Antibodies: A Laboratory Manual". Cold Spring Harbor: Cold Spring Harbor Laboratory Press (1988)].

For selection of antibodies capable of specifically binding a specific MHC:peptide complex, a large Fab-phage library consisting of a repertoire of $3.7\times10^{10}$ recombinant human Fab's (de Haard, H. J. et al., 1999. J. Biol. Chem. 274:18218-18230) was used. Due to exposure of the Fab's to streptavidin coated plates during selection, the library was first depleted of streptavidin binders, and subsequently used for panning soluble recombinant HLA-A2:$Tax_{11-19}$ complex. A 1,300 fold enrichment in phage titer was observed after three rounds of panning (Table 2). The specificity of the selected Fab-phages was determined by a differential ELISA using streptavidin coated wells incubated with biotinylated HLA-A2 in complex with either the $Tax_{11-19}$ peptide or negative control HLA-A2 restricted peptides. Phage clones analyzed following the third round of selection exhibited two types of binding patterns toward the HLA-A2:$Tax_{11-19}$ complex; one class of antibodies consisted of pan MHC binders which cannot differentiate between the various specific MHC:peptide complexes; the second type consisted of antibodies that specifically bound the HLA-A2:$Tax_{11-19}$ complex. The ELISA screen revealed that 87 percent of randomly selected clones (78/90) screened from the third round of panning appeared to specifically bind the HLA-A2:$Tax_{11-19}$ complex.

TABLE 2

Screening of Fab-phages for anti HLA-A2:$Tax_{11-19}$ complex Fab's.

| Cycle | Phage input (I) | Phage output (O) | Ratio (O/I) | Fold enrichment | MHC:peptide complex binders | Fraction MHC:peptide complex binders | No. of Fab's |
|---|---|---|---|---|---|---|---|
| 1 | $7.2 \times 10^{12}$ | $9.6 \times 10^5$ | $1.3 \times 10^{-7}$ | — | — | — | — |
| 2 | $5.8 \times 10^{13}$ | $1.1 \times 10^7$ | $1.9 \times 10^{-7}$ | 1.5 | 15/90 (17%) | 10/90 (11%) | 6 |
| 3 | $5.2 \times 10^{13}$ | $8.7 \times 10^9$ | $1.7 \times 10^{-4}$ | 1,300 | 78/90 (87%) | 56/90 (62%) | 14 |

Figure 1:
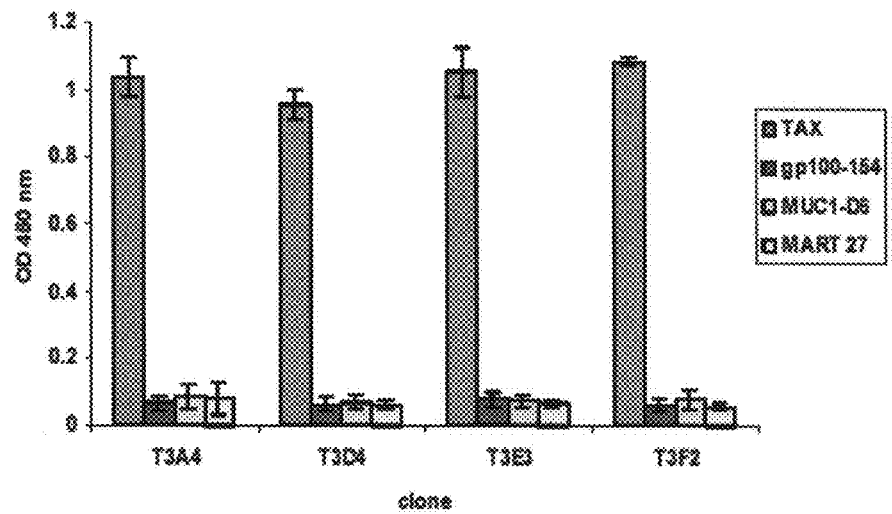

However, an unexpectedly high percentage of Fab's, 62 percent (56/90), were fully $Tax_{11-19}$ peptide dependent for binding and specific for HLA-A2:$Tax_{11-19}$ complex when tested as Fab-phages in ELISAs using various HLA-A2:control peptide complexes as binding targets. As shown in Table 2, 62 percent of the clones bound only to the HLA-A2:$Tax_{11-19}$ complex and not to negative control complexes containing other HLA-A2 restricted peptides. Such clones thus exhibited an MHC restricted peptide specific binding similar to T-cell receptors (TCRs). These apparent HLA-A2:$Tax_{11-19}$ complex specific clones remained specific for HLA-A2:$Tax_{11-19}$ complex in a secondary screening using HLA-A2 complexed with other HLA-A2 restricted peptides (listed under Materials and Methods). FIG. 1 shows a representative analysis of four Fab clones which reacted only with the HLA-A2:Tax$_{11-19}$ complex and not with HLA-A2:negative control peptide complexes displaying melanoma gp100 and MART-1-derived epitopes, and the MUC1-derived D6 epitope.

The diversity pattern of the peptide specific clones (from round two or three) was examined by DNA fingerprint analysis. Twenty different restriction patterns (6 for clones isolated from the second round of panning, and 14 different patterns after the third round of selection) were found, indicating successful selection of several different Fab's capable of specifically binding HLA-A2:Tax$_{11-19}$ complex. DNA sequencing analysis confirmed these observations. The variable heavy and variable light chain complementarity determining region sequences of 14 clones specific for HLA-A2:Tax$_{11-19}$ complex are shown in Table 3.

TABLE 3

Amino acid sequences of complementarity determining regions of Fab's specifically binding HLA-A2:Tax$_{11-19}$ complex

| Fab | Chain* | CDR1 | CDR2 | CDR3 |
|---|---|---|---|---|
| T3E3 | H | SYTIS (SEQ ID NO: 14) | GIIPIFGTANYAQKFQG (SEQ ID NO: 15) | DTDSSGYYGAVDY (SEQ ID NO: 16) |
|  | L | RASQSVGSYLA (SEQ ID NO: 17) | DASHRAT (SEQ ID NO: 18) | QQRSNWPPMYT (SEQ ID NO: 19) |
| T3F2 | H | SYGMH (SEQ ID NO: 20) | VISYDGSNKYYADSVKG (SEQ ID NO: 21) | DFDYGDSYYYYGMDV (SEQ ID NO: 22) |
|  | L | RSSQSLLHSNGY (SEQ ID NO: 23) | LGSNRAS (SEQ ID NO: 24) | MQALQTPRT (SEQ ID NO: 25) |
| T3D4 | H | NYGIN (SEQ ID NO: 26) | WISAYNGDTKYAQRLQD (SEQ ID NO: 27) | GDSTVGYEYLQY (SEQ ID NO: 28) |
|  | L | QASQGIGKYLN (SEQ ID NO: 29) | VASSLQS (SEQ ID NO: 30) | QQTSSFPPT (SEQ ID NO: 31) |
| T3D3 | H | SYAIS (SEQ ID NO: 32) | RIIPILGIANYAQKFQG (SEQ ID NO: 33) | QGGDYSNYYYYMDV (SEQ ID NO: 34) |
|  | L | RASQSVSSYLA (SEQ ID NO: 35) | DASNRAT (SEQ ID NO: 36) | QHRFNWPVT (SEQ ID NO: 37) |
| T3D1 | H | SYGMH (SEQ ID NO: 38) | VISYDGSNKYYADSVKG (SEQ ID NO: 39) | DQTYYGSGSPRGGLDY (SEQ ID NO: 40) |
|  | L | TGSSGSIANNYVQ (SEQ ID NO: 41) | EDDQRPS (SEQ ID NO: 42) | QSYDNSNSFVV (SEQ ID NO: 43) |
| T2B12 | H | SNSAAWN (SEQ ID NO: 44) | RTYYRSKWYNDYVSVKS (SEQ ID NO: 45) | GPYDTTGPWGNWFDP (SEQ ID NO: 46) |
|  | L | RASQSVSSDLA (SEQ ID NO: 47) | GASYRAT (SEQ ID NO: 48) | QQYGSSPRT (SEQ ID NO: 49) |
| T2G7 | H | SYGMH (SEQ ID NO: 50) | VISYDGSNKYYADSVKG (SEQ ID NO: 51) | DFDYGDSYYYYGMDV (SEQ ID NO: 52) |
|  | L | RSSQSLLHSNGYNYLD (SEQ ID NO: 53) | LGSNRAS (SEQ ID NO: 54) | MQALQTPRT (SEQ ID NO: 55) |
| T2H9 | H | SYAMS (SEQ ID NO: 56) | AISGSGGSTYYADSVKG (SEQ ID NO: 57) | DSLAGATGTDFDY (SEQ ID NO: 58) |
|  | L | RASQTVTANYLA (SEQ ID NO: 59) | DASVRAT (SEQ ID NO: 60) | QQYGSSPIT (SEQ ID NO: 61) |
| T3A2 | H | SYAMS (SEQ ID NO: 62) | GISGSGGSTYYADSVKG (SEQ ID NO: 63) | DFDYGGNSGSLFDY (SEQ ID NO: 64) |
|  | L | GASESVGGNYLA (SEQ ID NO: 65) | DASTRAT (SEQ ID NO: 66) | QHYGSSPSTY (SEQ ID NO: 67) |
| T3A4 | H | SSNWWS (SEQ ID NO: 68) | EIYHSGSTNYNPSLKS (SEQ ID NO: 69) | HSYDYLWGTYRFDY (SEQ ID NO: 70) |
|  | L | RASQDIGTWLA (SEQ ID NO: 71) | AATTLES (SEQ ID NO: 72) | QQARSLPYT (SEQ ID NO: 73) |
| T3B5 | H | NYGIN (SEQ ID NO: 74) | WISAYNGDTKYAQRLQD (SEQ ID NO: 75) | GDSTVGYEYLQY (SEQ ID NO: 76) |
|  | L | QASQGIGKYLN (SEQ ID NO: 77) | VASSLQS (SEQ ID NO: 78) | QQTSSFPPT (SEQ ID NO: 79) |
| T4B7 | H | SYGMH (SEQ ID NO: 80) | VISYDGSNKYYADSVKG (SEQ ID NO: 81) | DYNGYGDYVLGY (SEQ ID NO: 82) |
|  | L | RASQSVSSYLA (SEQ ID NO: 83) | DASNRAT (SEQ ID NO: 84) | QQRSNWASYT (SEQ ID NO: 85) |

TABLE 3-continued

Amino acid sequences of complementarity
determining regions of Fab's specifically
binding HLA-A2:Tax$_{11-19}$complex

| Fab | Chain* | CDR1 | CDR2 | CDR3 |
|---|---|---|---|---|
| T4D10 | H | SYYMH (SEQ ID NO: 86) | IINPSGGSTSYAQKFQG (SEQ ID NO: 87) | DRGGGYDVSPYGMDV (SEQ ID NO: 88) |
|  | L | RASQSISSYLN (SEQ ID NO: 89) | AASNLQT (SEQ ID NO: 90) | QQTYSLPT (SEQ ID NO: 91) |
| T4B12 | H | SYAIS (SEQ ID NO: 92) | GIIPIPGITNYAQKFQG (SEQ ID NO: 93) | RVGYYYGMDV (SEQ ID NO: 94) |
|  | L | AGSGGDIASNFVQ (SEQ ID NO: 95) | EENRRPS (SEQ ID NO: 96) | QSYDGSAW (SEQ ID NO: 97) |

*H - heavy chain, L - light chain

Specificity and affinity of anti HLA-A2:Tax$_{11-19}$ complex Fab's: Using *E. coli* BL21 or TG1 cells, soluble Fab's from 3 phage clones exhibiting the most specific binding pattern to HLA-A2:Tax$_{11-19}$ complex (analyzed above, FIG. 1) were produced.

SDS-PAGE analysis of Fab's purified from the periplasmic fraction of *E. coli* transformants by nickel affinity chromatography revealed homogenous, pure Fab's with the expected molecular weight of 50 kDa (FIG. 2a). Quantities of 2 to 4 milligrams of pure Fab was obtained from 1 liter of bacterial shake flask culture. For further manipulation; i.e. to increase the avidity of monomeric Fab's, the Fab's were also produced by in-vitro refolding. The light chain and Fd fragment (truncated portion of the heavy chain consisting of the variable region and the CH1 domain of the constant region) were subcloned into pET based expression vectors for T7 promoter regulated expression of cloned inserts, and upon induction with IPTG, large amounts of recombinant protein accumulated as intracellular inclusion bodies (FIG. 2b). Upon in-vitro redox shuffling refolding, purified monomeric Fab's were obtained in high yield (4 to 6 milligrams of purified Fab was obtained from two 1 liter shake flask cultures, each expressing the Fab light or Fd fragment; FIG. 2c).

The fine specificity of the soluble Fab's for HLA-A2:Tax$_{11-19}$ complex was analyzed by ELISA using biotinylated HLA-A2:Tax$_{11-19}$ complex immobilized to BSA-streptavidin coated wells. The BSA-streptavidin-biotin spacer enables the correct folding of the complex, which may be distorted by direct binding to plastic. To verify correct folding of the bound complex and its stability during binding assays, the ability of the bound complex to react with the conformation specific monoclonal antibody w6/32 which exclusively recognizes correctly folded, peptide complexed HLA was monitored. FIGS. 3a-c show specific binding of soluble Fab's T3D4, T3E3, and T3F2, respectively, to HLA-A2:Tax$_{11-19}$ complex, but not to 10 control HLA-A2:peptide complexes containing viral epitopes derived from CMV or EBV, and a variety of tumor associated epitopes such as telomerase epitopes (540, 865), melanoma gp100 and MART-1-derived epitopes (154,209,280 and MART, respectively), and the MUC1-derived epitopes A7 and D6 (see experimental procedures for list of peptides). Thus, these anti specific MHC:peptide complex Fab's exhibit the binding characteristics and fine specificity of a TCR. In control experiments, the Fab's did not recognize the Tax$_{11-19}$ peptide alone when immobilized on the plate, nor immobilized streptavidin or other protein antigens such as BSA, IgG, RNase, or chymotrypsin (data not shown).

The binding affinity properties of two of the soluble Fab's were tested using a saturation ELISA assay using addition of increasing amounts of Fab's to biotinylated HLA-A2:Tax$_{11-19}$ bound to streptavidin coated plates. As shown in FIGS. 4a-b, the binding of Fab's T3E3 and T3F2, respectively, was dose dependent and saturable. Extrapolating the 50 percent binding signal of either fragment revealed that their affinity was in the nanomolar range.

Finally, the apparent binding affinity of the Fab's for HLA-A2:Tax$_{11-19}$ complex was determined using a competition binding assay in which the binding of [125]iodine labeled Fab was competed with increasing concentrations of unlabeled Fab's. These binding studies (FIG. 4c) revealed an apparent binding affinity of approximately 25 to 30 nanomolar for the T3F2 antibody. Similar results were observed for the T3E3 antibody (not shown).

Detection of HLA-A2:Tax$_{11-19}$ complex on peptide pulsed antigen-presenting cells (APCs): To demonstrate that the isolated Fab's can specifically bind HLA-A2:Tax$_{11-19}$ complex not only in the recombinant soluble form but also in the native form, as expressed on the cell surface, murine TAP2 deficient RMA-S cells transfected with the human HLA-A2 gene in a single chain format (Pascolo, S. et al., 1997. J. Exp. Med. 185:2043-2051) (HLA-A2.1/Db-beta$_2$-microglobulin single chain, RMA-S-HHD cells). The Tax$_{11-19}$ peptide and HLA-A2 restricted control peptides were loaded on RMA-S-HHD cells and the ability of the selected Fab's to bind to peptide loaded cells was monitored by flow cytometry. Peptide induced MHC stabilization of the TAP2 mutant RMA-S-HHD cells was demonstrated by reactivity of monoclonal antibodies w6/32 (HLA conformation dependent) and BB7.2 (HLA-A2 specific) with peptide loaded but not unloaded cells (data not shown). Fab's T3E3 and T3F2 reacted only with Tax$_{11-19}$ peptide loaded RMA-S-HHD cells but not with cells loaded with the gp100 derived G9-154 peptide (FIGS. 5a-b, respectively). Similar results were observed using flow cytometric analysis using 10 other HLA-A2 restricted control peptides (data not shown).

Cells, of the TAP and HLA-A2 positive EBV transformed B lymphoblast cell line JY were also used as APCs. The cells were incubated with Tax$_{11-19}$ peptide, and HLA-A2 restricted control peptides, and following incubation the cells were washed and incubated with the Fab's. The T3E3 or T3F2-Fab's were found to bind only to JY cells incubated with the Tax$_{11-19}$ peptide against which they were selected but not to HLA-A2 restricted control peptides-(FIGS. 5c-d, respectively). As a control, peptide loaded HLA-A2 negative/HLA-A1 positive APD B cells were also used. No binding of the Fab's to these cells was observed (data not shown). Fab's T3E3 and T3F2 were also tested for binding to peptide pulsed mature HLA-A2 positive dendritic cells. As shown in FIGS. 5e-f, respectively, the T3E3 and T3F2 Fab's recognized HLA-A2 positive dendritic cells pulsed with $Tax_{11-19}$ peptide but not with a control gp100-derived peptide.

The Fab's were modified for detection of MHC:peptide complex on the surface of cells. Since the density of a particular endogenous HLA:peptide complex on cells is expected to be low compared to that of peptide pulsed APCs, the avidity of Fab T3F2 was increased by making Fab tetramers, which are directly tagged with a fluorescent probe. This approach was used previously to increase the binding avidity of MHC:peptide complexes to TCRs or to increase the sensitivity of recombinant antibody molecules (Cloutier, S. M. et al., 2000. Mol. Immunol. 37:1067-1077). Another advantage of using fluorescently labeled tetramers is that only a single staining step is required whereas monomeric unlabeled Fab's require a fluorescently labeled secondary antibody. The Fab tetramers generated with fluorescently labeled streptavidin were thus used to measure the expression of HLA-A2:$Tax_{11-19}$ complex on the surface of peptide pulsed APCs. As shown in FIGS. 6a-c, the intensity of the binding as measured by flow cytometry with peptide pulsed RMA-S-HHD (FIG. 6a), JY cells (FIG. 6b), and human dendritic cells (FIG. 6c), was dramatically increased by two logs compared to the staining intensity with the T3F2 Fab monomer.

Unexpectedly, the staining pattern of the mature HLA-A2 positive dendritic cells was found to be scattered over a wide range of fluorescence intensities, indicating for the first time that dendritic cell populations display heterogeneous levels of specific MHC:peptide complexes at the cell surface. Such results therefore indicate the potency of the Fab's such as those described herein for studying the biology of specific MHC:peptide complex presentation by APCs.

In particular, these results demonstrate the ability of the Fab's to detect cell surface displayed HLA-A2:$Tax_{11-19}$ complex.

Cell surface detection of HLA-A2:$Tax_{11-19}$ complex formed by intracellular antigen processing: To examine the ability of the Fab's to detect HLA-A2:$Tax_{11-19}$ complex produced by physiological antigen processing, the HTLV-1 Tax gene was transfected Pinto HLA-A2 positive and negative JY or APD cells, respectively. Twenty four hours following transfection, the reactivity of T3F2 to cell surface displayed HLA-A2:$Tax_{11-19}$ complex was tested by flow cytometry. The analysis was performed using the high avidity tetrameric Fab T3F2. Positive staining above control could be clearly seen only with HLA-A2 positive JY cells transfected with the Tax gene but not with HLA-A2 negative cells transfected with the Tax gene (FIGS. 7a-b, respectively). Negative control Fab G2D12 specific for HLA-A2:G9-154 complex did not react with the Tax transfected JY cells (FIG. 7a). The $Tax_{11-19}$ peptide specific, MHC restricted pattern of reactivity by T3F2 was not due to differences in transfection efficiency, or HLA expression of JY and APD cells. As determined via control experiments employing transfection of green fluorescent protein (GFP) into these cells, the percentage of transfected cells with both cell lines using the same transfection protocol used for expression of Fab was similar (FIG. 7c), and the staining intensity of these cells with w6/32, a pan MHC monoclonal antibody, was similar (data not shown). These results indicate that the Fab's are capable of detecting HLA-A2:$Tax_{11-19}$ complex formed by intracellular antigen processing.

The use of Fab T3F2 for detecting HLA-A2:$Tax_{11-19}$ complex on virus infected cells was attempted. To this end, HLA-A2 negative HUT 102 and HLA-A2 positive RSCD4 cells (human CD4 positive T-lymphocyte cell lines infected with HTLV-1) were used. As shown in FIG. 7d, a significant staining with Fab T3F2 was observed on RSCD4 but not on HUT 102 cells, indicating that the Fab is capable of detecting the specific HLA-A2:$Tax_{11-19}$ complex on the surface of virus infected cells. Unexpectedly, the staining pattern revealed two cell subpopulations having moderate or high reactivity, respectively, with the Fab, which may indicate variability in the expression of the HLA-A2:$Tax_{11-19}$ complex within subpopulations of RSCD4 HTLV-1 infected cells. Similar variability was observed in staining experiments with an anti Tax protein antibody (not shown). Negative control Fab G2D12 specific for HLA-A2:G9-154 complex did not stain RSCD4 cells (FIG. 7d).

These results underscore the utility of anti specific MHC:peptide complex Fab's, in particular that of the above described anti HLA-A2:$Tax_{11-19}$ complex fragments, for the study of antigen presentation on APCs as well as virus infected cells.

High sensitivity detection and direct quantitation of surface expressed HLA-A2:$Tax_{11-19}$ complex on APCs and virus infected cells: The data presented above demonstrate the high specificity of the HLA-A2:$Tax_{11-19}$ complex specific Fab's as well as their ability to detect naturally processed $Tax_{11-19}$ peptide complexed with HLA-A2. The sensitivity of specific MHC:peptide recognition by the Fab's in-vitro was tested by staining with Fab T3F2 was tested over a broad range of $Tax_{11-19}$ peptide concentrations. As shown in FIGS. 8a-b, titration of peptide pulsed JY cells using graded concentrations of $Tax_{11-19}$ peptide demonstrated staining intensity dependent on the concentration of the peptide used for pulsing, and that the Fab was capable of detecting HLA-A2:$Tax_{11-19}$ complex when pulsing $Tax_{11-19}$ peptide at a concentration in the low nanomolar range. The staining intensity of peptide pulsed JY cells observed with T3F2 Fab was estimated by comparison to calibration beads displaying graded numbers of phycoerythrin molecules. This comparison enabled determination of the number of HLA-A2:$Tax_{11-19}$ complexes displayed on the surface of cells that are pulsed with various concentrations of the $Tax_{11-19}$ peptide (FIG. 8a and Table 2). Specific detection of as few as 100 HLA-A2:$Tax_{11-19}$ complexes per cell was achieved (using 6 nanomolar $Tax_{11-19}$ peptide pulsing) and reached saturation at about $1.1 \times$ to $1.2 \times 10^5$ complexes per cell when pulsing with 25 to 50 micromolar $Tax_{11-19}$ peptide.

These results therefore demonstrate that the sensitivity of specific MHC:peptide complex detection by T3F2 Fab is in the same range as the minimal concentration peptide needed to elicit measurable cytokine secretion (IL-2 or IFN-gamma) from T-lymphocyte hybridomas or target T-lymphocyte lysis by CD8 positive cytotoxic T-lymphocyte lines (Reis e Sousa, C., and Germain, R. N., 1995. J. Exp. Med. 182:841-851; Reis e Sousa, C. et al., 1996. J. Exp. Med. 184:149-157).

A major problem hampering the study of MHC dependent antigen presentation is the unavailability of adequate methods for quantifying surface expression levels on individual cells of specific MHC:peptide complexes produced by intracellular antigen processing. Using flow cytometric analysis of cell surface display of HLA-A2:$Tax_{11-14}$ complex using Fab T3F2 and comparison of the fluorescence intensity of T3F2 stained cells with that of calibration beads displaying graded numbers of phycoerythrin sites, it was possible to quantitate the number of specific HLA-A2:$Tax_{11-19}$ complexes on the cell surface (Table 4). Namely, JY cells pulsed with 1.5 micromolar $Tax_{11-19}$ peptide displayed on their surface $5 \times 10^3$ complexes per cell, while JY cells transfected with the Tax gene displayed on their surface, after intracellular antigen processing, $1 \times 10^4$ complexes per cell. The latter result is in complete agreement with recent quantitation of murine H-2k$^b$ bound to the ovalbumin peptide SIINFEKL after recombinant Vaccinia virus infection of cells in-vitro using an anti specific mouse MHC:peptide complex antibody (Porgador, A. et al., 1997. Immunity 6:715-726). As shown in FIG. 7$d$ and Table 4, direct detection of HLA-A2:Tax$_{11-19}$ complex on HTLV-1 infected cells enabled quantification of the number of complexes displayed on these cells. This analysis, using calibration beads, revealed that virus infected RSCD4 cells display on their surface about $3 \times 10^4$ HLA-A2:Tax$_{11-19}$ complexes per cell. As demonstrated in FIG. 7$d$, Fab T3F2 recognized two subpopulations of HTLV-1 infected RSCD4 cells with high and moderate reactivity. The highly reactive cells express on their surface $3 \times 1$ HLA-A2:Tax$_{11-19}$ complexes while the cell population with low to moderate staining intensity expresses several hundred HLA-A2:Tax$_{11-19}$ complexes. These results clearly demonstrate the power of such anti specific MHC:peptide complex Fab's to quantitate specific MHC:peptide complex expression on each cell in a population.

TABLE 4

Quantitation of the number of HLA-A2:Tax$_{11-19}$ complexes on the surface of APCs and HTLV-1-infected cells

| Cells | Mean number of sites per cell* |
|---|---|
| JY (50 mM peptide pulsed) | 120,132 ± 16,934 |
| JY (1.5 mM peptide pulsed) | 5,150 ± 691 |
| JY (Tax-transfected) | 12,746 ± 2,877 |
| RSCD4 (CD4 positive T-cells, HTLV-1-infected) | High: 32,820 ± 4,910 Low: 456 ± 72 |
| Background** | 32 ± 13 |

*The fluorescence intensity of stained cells in each experiment was compared with fluorescence intensities of calibration beads with known numbers of phycoerythrin (PE) molecules per bead (QuantiBRITE PE beads, Becton-Dickinson) and the number of sites for each experiment was determined. The mean number of non specific sites was determined by the intensity of staining of cells that are HLA-A2 positivebut not infected with HTLV-1, HLA-A2 negative cells infected with HTLV-1, or APCs not transfected with the Tax gene. The number of specific sites for each experiment was then calculated for each experiment. The deviation in number of sites depend on the sensitivity of detection and the physiological status of the cells in each individual determination.
**The background number of sites was determined as described, using SK-BR3 (HLA-A2 negative/HUT102), FM3D (HLA-A2 positive), and JY (HLA-A2 positive) cells not transfected with the Tax gene as controls.

Detection of cells displaying HLA-A2:Tax$_{11-19}$ complex in a heterogeneous cell population: At present, there are no reagents available for detecting and phenotyping individual cells displaying specific MHC:peptide complexes in mixed cell populations. Such reagents would have great utility, for example, for detecting or staging tumorigenic cells, or for studying antigen presentation in lymphoid tissues within heterogeneous cell populations. The anti specific MHC:peptide complex Fab's described above would be ideally suited to conduct such analyses. To simulate a heterogeneous population of cells in which only a small fraction expresses a specific MHC:peptide complex, Tax transfected and control non transfected JY cells were mixed in various ratios, and the reactivity of T3F2 Fab to such cells was analyzed by flow cytometry. As shown in FIG. 8$c$, single color flow cytometric analysis using T3F2 Fab allows accurate identification of the admixed Tax transfected JY cells that express on their surface HLA-A2:Tax$_{11-19}$ complex generated by intracellular antigen processing. T3F2 Fab was shown to be able to detect Tax transfected JY cells in a proportion as low as 1 percent within a population of non transfected cells (FIGS. 8$c$-$d$), as demonstrated by the ability to detect 0.5 percent of positive cells (calculated from a maximal 61.2 percent transfection efficiency of JY cells; FIG. 8$d$).

These results demonstrate the ease with which anti specific MHC:peptide complex, Fab's can reveal a cell subpopulation bearing a specific endogenously generated MHC:peptide complex.

Immunohistochemical detection of cells displaying HLA-A2:Tax$_{11-19}$ complex generated by intracellular antigen processing: Another major potential use for anti specific MHC:peptide complex antibodies is in situ immunohistochemical analysis of specific MHC:peptide complexes in tissues. As a first step to assess this potential, the capacity of T3F2 Fab to detect in situ HLA-A2:Tax$_{11-19}$ complex displayed on JY cells by intracellular antigen processing was determined. Tax transfected JY cells were subjected to single step immunohistochemical analysis using horseradish peroxidase conjugated T3F2 Fab. As shown in FIGS. 9$a$-$f$, these experiments showed the capacity of the Fab to strongly and specifically stain Tax transfected (FIGS. 9$a$-$b$) but not control non transfected JY cells (FIG. 9$c$). Negative control Fab G2D 12 specific for HLA-A2:G9-154 complex did not exhibit any significant immune reactivity on Tax transfected JY cells (FIG. 9$d$). Further evidence for the specific, MHC restricted reactivity of Fab T3F2 in these in situ immunohistochemistry experiments is provided by the lack of reactivity of the Fab with Tax transfected (FIG. 9$e$) and non transfected (FIG. 9$f$) HLA-A2 negative/HLA-A1 positive APD cells. These data demonstrate the capacity of the T3F2 Fab to specifically detect HLA-A2:Tax$_{11-19}$ complex generated by intracellular antigen processing in situ on cells and potentially in tissue sections. To the present inventors' knowledge, this is the first demonstration of in situ detection of a specific human MHC:peptide complex.

Specific cytolysis of cells displaying HLA-A2:Tax$_{11-19}$ complex by T3F2-PE38 immunotoxin: The capacity of an anti specific human MHC:viral peptide complex immunotoxin to cytolyse cells displaying such a complex was determined by testing the capacity of T3F2-PE38 to kill/damage peptide loaded APCs. The killing assay was performed by loading JY cells with Tax$_{11-19}$ peptide, or control HLA-A2 restricted peptides, including the gp100-derived G9-209 peptide. As shown in FIG. 10, T3F2-PE38 was capable of killing JY cells loaded with Tax$_{11-19}$ peptide with an IC$_{50}$ of 2,500 nanograms per milliliter. No T3F2-PE38 mediated cytolysis of JY cells loaded with control HLA-A2 restricted peptides, or of cells not loaded with peptide occurred.

Thus, the capacity to specifically and efficiently kill/damage target cells displaying a specific human MHC:viral peptide complex using cytotoxic conjugates targeted using an antibody specific for such a complex was demonstrated for the first time.

Discussion: The above described results demonstrate for the first time generation of recombinant antibody-derived molecules, such as Fab's, capable of specifically binding specific human MHC:pathogen-derived peptide complexes, such as MHC:viral peptide complexes, and of cytotoxic conjugates including such molecules to specifically kill/damage cells displaying, such complexes. Until now, anti specific MHC:pathogen-derived peptide complex antibodies have been generated against murine forms of such complexes only (Andersen, P. S. et al., 1996. Proc. Natl. Acad. Sci. U.S.A 93:1820-1824; Day, P. M. et al., 1997. Proc. Natl. Acad. Sci. U.S.A. 94:8064-8069; Porgador, A. et al., 1997. Immunity 6:715-726; Reiter, Y. et al., Proc. Natl. Acad. Sci. U.S.A. 94:4631-4636).

These novel molecules exhibit high affinity, high specificity binding to specific human MHC:pathogen-derived peptide complexes, and hence display TCR like specificity for such complexes. However, in contrast to the inherently low affinity of TCRs for MHC:peptide complexes, these molecules display the high affinity antigen binding characteristics of antibodies, while retaining TCR specificity. By virtue of such characteristics such molecules have very promising utility in the numerous diagnostic, therapeutic and scientific applications which would benefit from the capacity to specifically label or target specific human MHC:pathogen-derived peptide complexes such as those comprising viral peptides.

Crucial features of these Fab's were identified, including the capacity to: (a) bind with high sensitivity and specificity particular human MHC:pathogen-derived peptide complexes, such as HLA-A2:$Tax_{11-19}$ complex, expressed or displayed by cells which are infected with a pathogen such as HTLV-1, peptide loaded, in suspension, and/or surface immobilized using immunohistochemical techniques; and (b) the capacity to deliver molecules, such as toxins, to cells displaying a specific human MHC:pathogen-derived peptide complex, such as HLA-A2:$Tax_{11-19}$ complex.

An important feature of these molecules is their capacity to detect specific human MHC:pathogen-derived peptide complexes at surface densities near the threshold limit required for triggering signaling via the TCR. Studies from other laboratories using a monoclonal antibody specific for mouse MHC class I ($H-2K^b$) in complex with an ovalbumin peptide indicated that the lower limit of sensitivity of flow cytometry detection is in the range of 100 to 500 specific MHC:peptide complexes per cell using single step or sandwich staining techniques (Porgador, A. et al., 1997. Immunity 6:715-726). The data presented herein for anti specific human MHC:pathogen-derived peptide Fab's are in good agreement with these numbers since the HLA-A2:$Tax_{11-19}$ complex specific Fab was able to detect in a reproducible manner as few as 100 complexes per cell. These numbers agree with several estimates of the threshold number of specific MHC:peptide complexes on APCs required to elicit effector responses from T-lymphocytes, such as cytokine secretion (Demotz, S. et al., 1990. Science 249:1028-1030; Harding, C.V., and Unanue, E. R., 1990. Nature 346:574-576), and are about 10 fold greater than what may be required for cytotoxic T-lymphocyte mediated cell lysis (Christinck E R. et al., 1991. Nature 352:67-70; Sykulev Y. et al., 1996. Immunity 4:565-71). Using flow cytometry, it was possible to use an anti specific human MHC: pathogen-derived peptide complex Fab to detect such complexes on cells pulsed with peptide concentrations being similar to those required to trigger cytokine secretion by T-lymphocyte hybridoma or cytotoxic T-lymphocyte lines, and being within a few fold of concentrations required for sensitizing target T-lymphocytes for lysis in a short term assay by APCs (Porgador, A. et al., 1997. Immunity 6:715-726). The presently described data indicate that when applied to dissociated cell populations using flow cytometry, the Fab's can detect specific human MHC:pathogen-derived peptide complexes at densities approaching those required for activating T-lymphocytes. Hence these molecules are suitable reagents for evaluating specific human MHC:pathogen-derived peptide complex expression at low but physiologically relevant levels.

This principle was applied here to mixtures of the parental JY APCs and its Tax gene transfected derivative. The latter intracellularly processes Tax antigens and displays the relevant HLA-A2:$Tax_{11-19}$ complex at the cell surface, as demonstrated by positive staining of Tax transfected but not control cells using T3F2 Fab. Even when using T3F2 Fab in a single step staining for flow cytometry, it was possible to readily identify Tax transfected cells admixed with non transfected JY cells in a proportion as low as 1 percent. The extreme ease with which precise quantitation of cell surface expressed specific human MHC:pathogen-derived peptide complexes can be accomplished using this approach also makes it an invaluable tool for analyzing antigen processing and presentation. Increasingly, such analyzes are aimed at determining quantitative differences in antigen display resulting from use of distinct forms of an antigen, of various antigen delivery methods, or of cells deficient in some known or suspected component of the antigen processing machinery. Without reagents such as the presently described anti specific human MHC:viral peptide complex Fab's, the quantitation of cell surface levels of specific human MHC:pathogen-derived peptide complexes relies on biochemical isolation of antigenic peptides. This is an expensive and laborious process subject to numerous experimental artifacts and cannot distinguish between intracellular pools of loaded molecules and those on the cell surface accessible to TCRs.

In the data presented here, anti HLA-A2:$Tax_{11-19}$ complex Fab's enabled quantitation of such complexes generated by intracellular antigen processing on the surface of cells transfected with the Tax gene or on HTLV-1 infected cells. This analysis demonstrated that intracellular antigen processing in Tax transfected cells led to a display of about $10^4$ specific MHC:peptide complexes per cell. Comparison with total HLA-A2 staining showed that nearly 90 percent of the HLA-A2 molecules were occupied with a single-peptide species (not shown). These data agree with previous studies in which the number of $H-2K^b$:ovalbumin-derived peptide complexes on the surface of cells following infection with recombinant Vaccinia virus encoding the peptide was analyzed in a variety of contexts (Porgador, A. et al., 1997. Immunity 6:715-726). These data also agree with results from studies investigating the occupancy of MHC class I molecules by peptides derived from virally encoded proteins displayed by infected cells (Antón, L. C. et al., 1997. J. Immunol. 158:2535-42). Such occupancy estimates were obtained by analysis of stabilization of newly synthesized MHC class I heavy chain-$beta_2$-microglobulin complexes, or by elution of peptides from expressed MHC class I molecules and reconstruction experiments to determine the peptide concentration in the eluates. The ability of Fab T3F2 to detect the heterogeneity of HLA-A2:$Tax_{11-19}$ complex expression levels in a population of virally infected cells was shown. Such novel and striking data highlight the potential utility of such antibodies for studying specific human MHC:pathogen-derived peptide complex expression in contexts such as diagnosis of infection with a pathogen.

Immunohistochemical staining with T3F2 Fab permitted in situ detection of HLA-A2:$Tax_{11-19}$ complex generated by intracellular antigen processing on the surface of Tax transfected JY cells. Staining of background HLA display levels with the Fab was insignificant under these conditions because neither non transfected cells nor HLA-A2 negative cells transfected with Tax exhibited positive staining. Such data represent the first immunohistochemical visualization of a specific human MHC:peptide complex on immobilized biological samples.

Such an approach could be applied to confocal immunofluorescence microscopy, which, using anti specific human MHC:pathogen-derived peptide complex antibodies, would permit analysis of the intracellular site(s) of assembly and trafficking of such complexes. In situ localization of APCs displaying or expressing specific human MHC:pathogen-derived peptide complexes would be especially valuable in characterizing the intercellular interactions between APCs and T-lymphocytes involved in initiation, propagation, and maintenance of anti viral T-lymphocyte immune responses. Multicolor histochemistry could be used to reveal not only the type and location of viral APCs but also the phenotype of interacting anti viral T-lymphocytes, including the set of cytokines elicited.

The fact that 62 percent of the HLA-A2:Tax$_{11-19}$ complex binding Fab's were peptide specific and MHC restricted was unexpected since these antibodies were selected from a non immune repertoire considered not to be biased toward such specificity. The fact that it was possible to isolate from the same phage library recombinant Fab's capable of specifically binding a large variety of specific MHC:peptide complexes comprising various cancer associated or viral HLA-A2 restricted peptides (Denkberg, G. et al., 2002. Proc. Natl. Acad. Sci. U.S.A. 99:9421-9426; Lev, A. et al., 2002. Cancer Res. 62:3184-3194) indicates that the capacity to isolate anti MHC:Tax$_{11-19}$ complex antibodies from such a library was not Tax or peptide related. It is possible that one particular antibody family or antibody V gene segment could have an intrinsic propensity to bind HLA-A2 molecules, and that the high frequency could be explained by a high abundance of such antibodies in the non immune library. However, the sequences of the selected clones are derived from many different antibody families and germline segments, without any biases visible in the complementarity determining regions (CDRs) either (Table 3). The high frequency and high, affinities for some of the antibodies isolated herein suggest that these molecules may be present at a high frequency in the antibody repertoires from the B cell donors of the phage library, however an in-vivo role for such antibodies remains unclear.

Whatever the reason for this high frequency of Fab's to bind specific MHC:peptide complexes may be, it appears that this phage based approach can be successfully applied to identify recombinant antibodies capable of specifically binding to a large variety of specific human MHC:pathogen-derived peptide complexes. Thus, it may now be possible to elucidate the role of pathogen-derived antigens not only from the perspective of the T-lymphocyte, using MHC:pathogen-derived peptide complex based TCR detection reagents such as tetrameric single chain MHC:pathogen-derived peptide complexes, but also from the perspective of pathogen-derived APCs and diseased cells, using the novel antibody type described herein.

A further application for anti specific human MHC:pathogen-derived peptide complex antibodies is in structure function studies of specific interactions between such complexes and cognate TCRs. By mutating particular residues in the MHC restricted pathogen-derived peptide and testing the influence of these mutations on the binding of the Fab's and peptide specific T-lymphocyte clones, it may be possible to obtain important data regarding the structure function relationship and the different nature of the recognition process between such Fab's and the native TCR (Stryhn A. et al., 1996. Proc. Natl. Acad. Sci. U.S.A. 93:10338-10342).

Conclusion: By virtue of the capacity of the presently described Fab's to specifically bind with optimal affinity and specificity particular human APM:pathogen-derived antigen complexes, such reagents are uniquely suitable and optimal relative to all prior art compounds for: (a) identification, and characterization of cells/tissues expressing or displaying such complexes; (b) specific killing of cells displaying such complexes by targeting cytotoxic drugs or radionuclides to pathogen infected cells analogously to previously described methodologies (Boon, T. and van der Bruggen, P., 1996. J. Exp. Med. 183:725-729; Renkvist, N. et al., 2001. Cancer Immunol. Immunother. 50:3-15; Rosenberg, S. A., 2001. Nature 411:380-384); (c) confocal microscopic visualization and characterization of the intracellular localization and trafficking of such complexes; (d) tracking of cells displaying such complexes in real-time via confocal microscopy and in-vivo; and (e) modulation of immune responses by blocking interactions between specific human APM:pathogen-derived antigen complexes and cognate TCRs, analogously to previously described methodologies practiced by the present inventors (Denkberg, G. et al., 2002. Proc. Natl. Acad. Sci. U.S.A. 99:9421-9426; Lev, A. et al., 2002. Cancer Res. 62:3184-3194). For example, the presently described reagents could be used to control pathogenic T-lymphocyte mediated anti pathogen immune responses without the risk of antigen administration to an infected individual, and without the loss of function of an entire MHC allele, as would be the case with prior art anti MHC antibodies.

Thus, the presently described compounds are uniquely and optimally suitable for diagnosing, characterizing and treating diseases in humans caused by pathogens such as viruses, and for studying aspects of such diseases involving antigen presentation.

Example 2

Optimal Prediction, Diagnosis, Staging, Monitoring and Prognosis of a Pathogen-associated Disease Using a Detection Reagent Specific for a Complex of a Human Antigen-presenting Molecule and a Pathogen-derived Antigen Background: As described above, there are currently no satisfactory treatment methods, nor does the state of the art enable optimal prediction, diagnosis, staging, monitoring and prognosis for diseases associated with HTLV-1 infection, such as HAM/TSP, in human patients. The pathogenesis of such diseases is associated with lymphocyte mediated autoimmune responses primarily directed against peptides of the HTLV-1 Tax protein. Hence, an optimal strategy for diagnosing, staging and characterizing patients having such a disease would be to obtain and employ a detection reagent capable of specifically detecting a complex of an antigen-presenting molecule (APM) and a Tax-derived peptide antigen displayed by cells infected with HTLV-1. It will be appreciated that the optimal diagnosis, staging and monitoring capacity which could be afforded by such a reagent would in turn enable the optimal development of therapy for such a disease. While various molecules capable of binding particular APM:antigen complexes have been proposed in the prior art, none have been shown to be capable of detecting a complex of a human antigen-presenting molecule and a pathogen-derived antigen, and hence of enabling characterization of a pathogen-induced disease. As described below, the present inventors have devised for the first time relative to the prior art a method of utilizing a detection reagent specific for a complex of a human APM and an HTLV-1 Tax peptide for optimally characterizing an HTLV-1-associated disease, such as HAM/TSP, in a human, thereby overcoming the limitations of the prior art.

Materials and Methods:

Harvesting of peripheral blood and cerebrospinal fluid lymphocytes: Peripheral blood is harvested via routine blood collection and cerebrospinal fluid (CSF) is harvested via lumbar puncture from HLA-A2 positive HAM/TSP patients. Peripheral blood mononuclear cells (PBMCs) are isolated from the harvested peripheral blood by centrifugation over a Ficoll cushion following hypotonic erythrocyte lysis. CD4+, CD4+CD25+, and CD8+ T-cell subsets are isolated from the harvested blood and CSF via magnetic cell sorting using MACS beads.

Flow cytometric analysis of HLA-A2:Tax$_{11-19}$ complexes on peripheral blood and cerebrospinal fluid T-cell subsets from HAM/TSP patients: The isolated CD4+, CD4+CD25+ and CD8+ T-cell subsets are analyzed for surface expression of HLA-A2:Tax$_{11-19}$ peptide complex via flow cytometry, performed essentially as described above in Example 1, using as complex detection reagent phycoerythrin-conjugated T3F2 Fab tetramer (refer to Example 1, above). Alternately, CD4+, CD4+CD25+ and CD8+ T-cell subsets from the harvested blood and from the harvested CSF are analyzed for surface expression of HLA-A2:Tax$_{11-19}$ complex via multicolor flow cytometry, essentially as previously described (Kivisakk P. et al., 2003. Proc. Natl. Acad. Sci. U.S.A. 100: 8389-8394), using as detection reagents phycoerythrin-conjugated T3F2 Fab tetramer with: FITC-conjugated anti-human CD4 antibody; FITC-conjugated anti-human CD8 antibody; or FITC-conjugated anti-human CD4 antibody and PE-Cy5-conjugated anti-human CD25 antibody. As described in Example 1 above, Tax$_{11-19}$ peptide-loaded or gp100-derived G9-154 peptide-loaded HLA-A2-positive RMAS-HHD cells are employed as positive and negative controls, respectively, for surface expression of the HLA-A2: Tax$_{11-19}$ complex.

Analysis of HTLV-1 proviral DNA load, and HTLV-1 tax mRNA load in lymphocytes: Analysis of HTLV-1 proviral DNA load is performed via PCR, essentially as previously described (Thorstensson R. et al., Transfusion 42:780-91; Coste J., 2000. Transfus Clin Biol. 7 Suppl 1:11s-17s; Nakamura S. and Nakayama T., 1997. Nippon Rinsho. 55:833-8; Kazanji M. et al., 2000. J. Virol. 74:4860-7). Analysis of HTLV-1 tax mRNA load is performed via RT-PCR essentially as previously described (Kazanji M., 2000. AIDS Res Hum Retroviruses 16:1741-6; Higashiyama Y. et al. 1994. Clin Exp Immunol. 96:193-201; Kazanji M. et al., 2000. J Virol. 74:4860-7).

Determination of HAM/TSP disease severity: Disease severity in HAM/TSP patients is measured according to expanded disability status scale, essentially as previously described (EDSS; Kurtzke J., 1983. Neurology 33:1444-1452).

Results:

Profiles of HLA-A2:Tax$_{11-19}$ complex surface expression on CD4+, CD4+CD25+ and CD8+ T-cell subsets isolated from peripheral blood and CSF of HAM/TSP patients are determined with high sensitivity via flow cytometry. CD4+, CD8+, and CD4+CD25+cells are found to specifically display HLA-A2:Tax$_{11-19}$ complex surface expression. The highest levels of surface complex expression are detected in CD4+CD25+cells, in accordance with such T-cells being the major reservoir of HTLV-1 provirus. Correlations are analyzed and determined between levels of HLA-A2:Tax$_{11-19}$ complex expression on CD8+, CD4+, and CD4+CD25+cells with HTLV-1 proviral DNA load, HTLV-1 tax mRNA load, and HTLV-1 Tax-specific CD8+ T-cell frequencies. Correlation of surface expression levels of the complex on the various cell T-cell subsets with disease severity is analyzed and determined. Levels of HLA-A2:Tax$_{11-19}$ complex surface expression on CD4+CD25+T-lymphocytes are found to correlate with disease severity.

Conclusion: The anti-APM:antigen complex antibodies of the present invention can be used for enabling optimal prediction, diagnosis, staging, monitoring and prognosis of a pathogen-associated disease such as an HTLV-1 associated disease, thereby overcoming numerous limitations of the prior art. In particular, the anti-HLA-A2:Tax$_{11-19}$ complex antibodies of the present invention can be used for enabling optimal prediction, diagnosis, staging, monitoring and prognosis of HAM/TSP in humans, thereby overcoming numerous limitations of the prior art. It will be appreciated that such antibodies enable optimal elucidation of the pathogenesis of HTLV-1 associated diseases, enable optimal development of therapy for such diseases, and can be employed as therapeutic agents to treat such diseases according to the presently disclosed teachings.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by its accession number was specifically and individually indicated to be incorporated herein by reference. In addition, citation or identification of any reference in this application shall not be construed as an admission that such reference is available as prior art to the present invention.

What is claimed is:

1. A method of killing or damaging a target human cell expressing or displaying a complex composed of a human antigen-presenting molecule and an antigen derived from a pathogen, the method comprising exposing the target cell to a composition-of-matter comprising an antibody or antibody fragment including an antigen-binding region which includes amino acid sequences as set forth in SEQ ID NOs:20 (CDR1), 21 (CDR2) and 22 (CDR3) in a heavy chain of the antibody, and amino acid sequences as set forth in SEQ ID NOs:23 (CDR1), 24 (CDR2) and 25 (CDR3) in a light chain of the antibody, said amino acid sequences being in a context of framework sequences, and a domain allowing said antibody or antibody fragment to kill the target human cell, thereby killing or damaging the target human cell expressing or displaying the complex composed of the human antigen-presenting molecule and the antigen derived from the pathogen.

2. The method of claim 1, wherein said domain comprises an antibody constant region or a toxin.

* * * * *